United States Patent [19]
Kazazian, Jr. et al.

[11] Patent Number: 6,150,160
[45] Date of Patent: Nov. 21, 2000

[54] COMPOSITIONS AND METHODS OF USE OF MAMMALIAN RETROTRANSPOSONS

[75] Inventors: Haig H. Kazazian, Jr.; Jef D. Boeke, both of Baltimore, Md.; John V. Moran, Exton; Beth A. Dombroski, Springfield, both of Pa.

[73] Assignees: The John Hopkins University, Baltimore, Md.; The Trustees of the University of Pennsylvania, Philadelphia, Pa.

[21] Appl. No.: 08/847,844

[22] Filed: Apr. 28, 1997

Related U.S. Application Data

[63] Continuation-in-part of application No. 08/749,805, Nov. 15, 1996, abandoned
[60] Provisional application No. 60/006,831, Nov. 16, 1995.
[51] Int. Cl.$^7$ .......................... C07H 21/04; C07H 21/02; C12N 15/63
[52] U.S. Cl. ................ 435/320.1; 536/23.5; 536/24.1; 536/23.1; 435/455
[58] Field of Search .............................. 435/320.1, 455; 514/44; 536/23.1, 23.5, 24.1

[56] References Cited

PUBLICATIONS

Palmiter et al., 1986, Ann. Rev. Genet. 20:465–499.
Qiagen, *Cat. No. 30210*, Chatsworth, CA.
Rose et al., 1990, *Methods in Yeast Genetics: A Laboratory Course Manual*, Cold Spring Harbor, NY—too voluminous to submit.
Sambrook et al., 1989, *Molecular Cloning: A Laboratory Manual*, Cold Spring Harbor, New York—too voluminous to submit.
Sassaman, 1996, *Characterization of five novel human L1 elements capable of retrotransposition, Doctoral Dissertation*, Johns Hopkins University, Baltimore, MD.
Scott et al., 1987, *Genomics* 1:113–125.
Sinden et al., 1981, *Proc. Natl. Acad. Sci. USA* 78:224–228.
Sinden et al., 1980, *Cell* 21:773–783.
Skowronski et al., 1988, *Mol. Cell Biol.* 8:1385–1397.
Smit et al., 1996, *Current Opinion in Genetics and Development*—too voluminous to submit.
Suck et al., 1988, *Nature* 332:464–468.
Swergold, 1990, *Mol. Cell. Biol.* 10:6718–6729.
Tchenio et al., 1993, *EMBO J.* 12:1487–1497.
Temin et al., 1985, *Mol. Biol. Evol.* 2:455–468.
Teng et al., 1996, *Nature* 383:641–644.
Trelogan et al., 1995, "Tightly regulated, developmentally specific expression of the first open reading frame from Line–1 during mouse embryogenesis", *Proc. Natl. Acad. Sci. USA* 92:1520–1524.
Tsao et al., 1989, *Cell* 56:111–118.
Usdin et al., 1989, *J. Biol. Chem.* 264:15681–15687.
Ward et al., 1990, *Nucl. Acids. Res.* 18:5319.
Weiner et al., 1986, *Ann. Rev. Biochem.* 55:631–661.
Adams et al., 1980, *Nucl. Acids Res.* 8:6113–6128.

Altschul et al., 1990, *J. Mol. Biol.* 215:403–410.
Barzilay et al., 1995, *Nucl. Acids Res.* 23:1544–1550.
Barzilay et al., 1995, *Nature Structural Biol.* 2:561–568.
Boeke et al., 1985, *Cell* 40:491–500.
Boeke et al., 1991, *Curr. Opin. Cell. Biol.* 3:502–507.
Braiterman, et al., 1994, *Gene* 139:19–26.
Bucheton et al., 1984, *Cell* 38:153–163.
Burkhoff et al., 1987, *Cell* 48:935–943.
Burton et al., 1986, *J. Mol. Biol.* 187:291–304.
Chee, 1996, Science 274:610–614.
Conway et al., 1985, *Proc. Natl. Acad. Sci. USA* 82:3949–3953.
Cooley et al., 1988, *Science*, 239:1121–1128.
Curcio et al., 1991, *Proc. Natl. Acad. Sci.* USA 88:936–940.
Demers et al., 1986, *Mol. Biol. Eval.* 3:179–190.
Derr et al., 1991, *Cell* 67:355–364.
Dombroski et al., 1993, *Proc. Natl. Acad. Sci. USA.* 90:6513–6517.
Dombroski et al., 1991, *Science* 254:1805–1808.
Dombroski et al., 1994, *Mol. Cell. Biol.* 14:4485–4492.
Drolet et al., 1994, *J. Biol. Chem.* 269:2068–2074.
Fanning et al., 1987, *Biochim. Biophys. Acta* 910:203–212.
Fanning et al., 1987, *Nucl. Acids Res.* 15:2251–2260.
Freeman et al., 1994, *BioTechniques* 17:47–52.
Garfinkel et al., 1985, *Cell* 42: 507–517.
Goff et al., 1981, *J. Virol.* 38:239–248.
Heidmann et al., 1988, *Proc. Natl. Acad. Sci. USA* 85:2219–2223.
Hohjoh et al., 1996, *EMBO J.* 15:630–639.
Hohjoh et al., 1990, *Nucl. Acids Res.* 18:4099–4104.
Holmes et al., 1992, *J. Biol. Chem.* 267:19765–19768.
Holmes et al., 1994, "A new retrotrnasposable human L1 element from the LRE2 locus on chromosome 1q produces a chimaeric insertion", *Nature Genetics* 7:143–148.
Holmes, 1994, *Thesis Dissertation*, Johns Hopkins University Press.
Hutchison et al., 1989, *Lines and related retrotransposons: long interspersed sequences in the eukaryotic genome in Mobile DNA* eds., Berg et al., pp. 593–617, ASM Press, Washington, DC.
Jensen et al., 1991, *EMBO J.* 10:1927–1937.
Johnson et al. 1988, J. Biol. Chem. 263:18017–18022.
Kazazian et al., 1988, *Nature* 332:164–166.
Kinsey, 1990, *Genetics* 126:317–326.
Kitchin et al., 1986, *J. Biol. Chem.* 261:11302–11309.
Kolosha et al., 1995, "Polymorphic Sequences Encoding the First Open Reading Frame Protein from Line–1 Ribonucleoprotein Particles", *The Journal of Biological Chemistry* 270:2868–2873.

(List continued on next page.)

*Primary Examiner*—Jasemine Chambers
*Assistant Examiner*—Anne-Marie Baker
*Attorney, Agent, or Firm*—Akin, Gump, Strauss, Hauer & Feld, L.L.P.

[57] ABSTRACT

The invention relates to an isolated DNAc molecule comprising a promoter P and an L1 cassette sequence comprising a core L1 retrotransposon element and methods of use thereof.

3 Claims, 33 Drawing Sheets

OTHER PUBLICATIONS

Kunkel, et al., 1991, *Methods in Enzymology* 204:125–139.

Lehman, 1974, *Science* 186:790–797.

Liebold et al., 1990, *Proc. Natl. Acad. Sci. USA* 87:6990–6994.

Lilley, 1981, *Nucl. Acids Res.* 9:1271–1288.

Liu et al., 1987, *Proc. Natl. Acad. Sci. USA* 84:7024–7027.

Luan et al., 1995, *Mol. Cell. Biol.* 15:3882–3891.

Luan et al., 1993, *Cell* 72:595–605.

Maestre et al., 1995, *EMBO J.* 14:6333–6338.

Maniatis et al., 1992, *Molecular cloning: A Laboratory Manual*, Cold Spring Harbor, New York, pp. 1–545—too voluminous to submit.

Martin, 1991, *Mol. Cell Biol.* 11:4804–4807.

Martin et al., 1995, *J. Mol. Biol.* 247:49–59.

Martin, 1995, "Characterization of a Line–1 cDNA that originated from RNA present in ribonucleoprotein particles: implications for the structure of an active mouse Line–1", *Gene* 153:261–266.

Martin, 1991, *Curr. Opin. Genet. Dev.* 1:505–508.

Mathias et al., 1991, *Science* 254:1808–1810.

Miki et al., 1992, *Cancer Research* 52:643–645.

Minakarni et al., 1992, *Nucl. Acids Res.* 12:3139–3145.

Mol et al., 1995, *Nature* 374:381–386.

Moran et al., 1996, *Cell* 87:917–927.

Morse et al., 1988, *Nature* 333:87–90.

Narita et al., 1993, *J. Clinical Invest.* 91:1862–1867.

Oefner et al., 1986, *J. Mol. Biol.* 192:605–632.

Pettijohn et al., 1980, *Proc. Natl. Acad. Sci. USA* 77:1331–1335.

Weiss, 1976, *J. Biol. chem.* 251:1896–1901.

Wilson, 1996, *Molecular Medicine* 334:1185–1187.

Woods–Samuels et al., 1989, *Genomics* 4:290–296.

Yates et al., 1985, *Nature* 313:812–815.

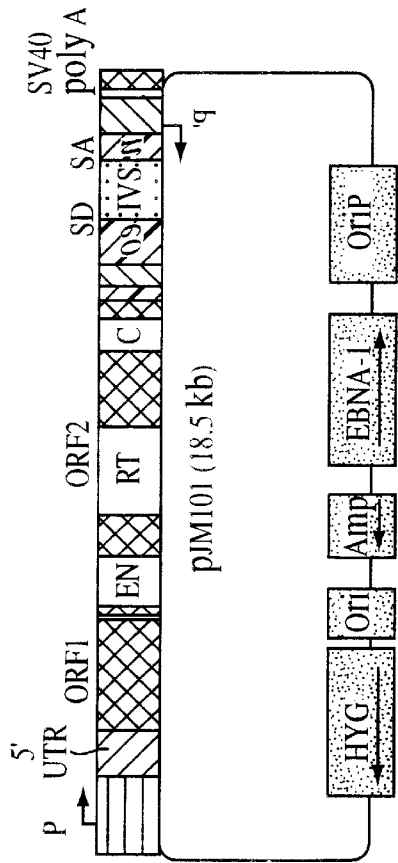
Fig. 2A
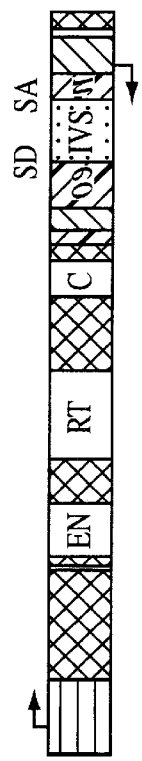
Fig. 2Bi
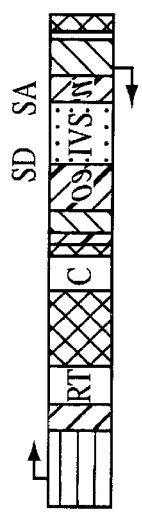
Fig. 2Bii
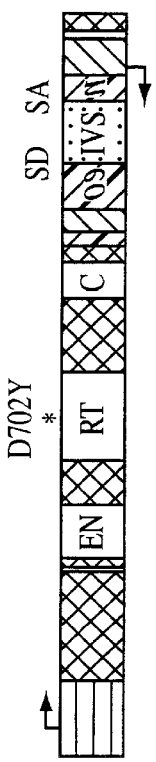
Fig. 2Biii

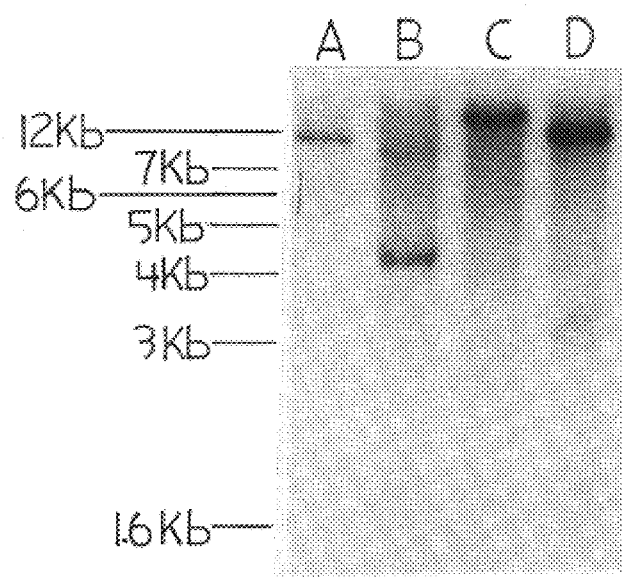
FIG.4A
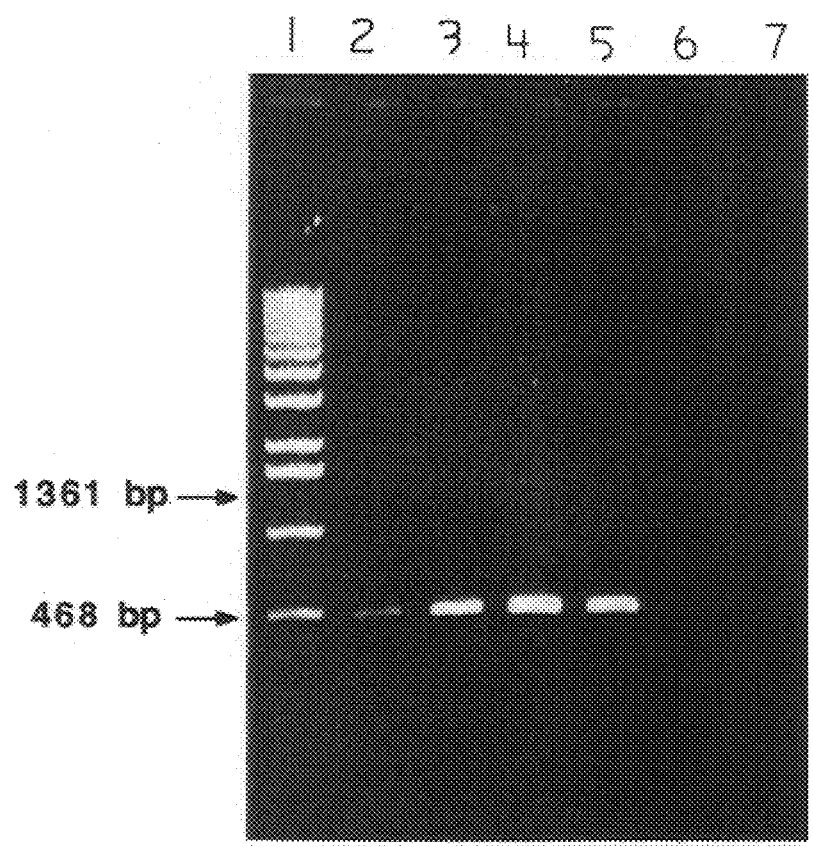
FIG.4Biii

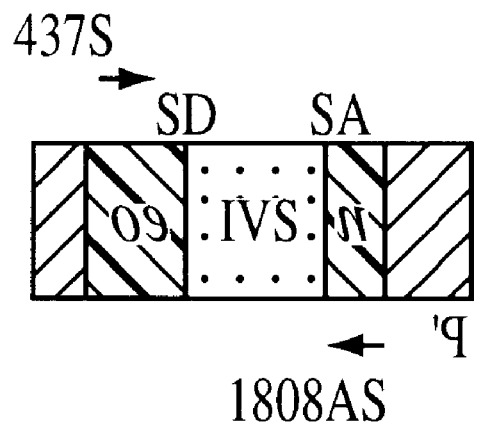
Fig. 4Bi
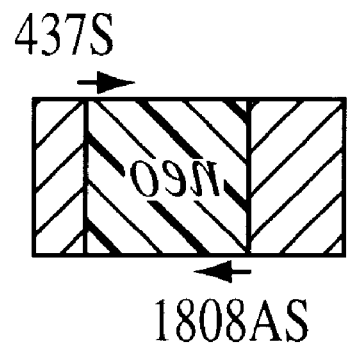
Fig. 4Bii

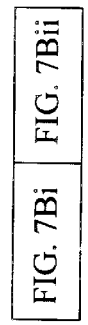

|  |  |  |  |  |  |
|---|---|---|---|---|---|
| TAD | .....MVQLKILYWNVGKS | (13) | YDIVAIQEPG | (22) | KGRAVIYVNK (25) PTTVYSIYSPILT |
| L1Tc (35) | DIEQNPGPIAVLQMNVSCL | (12) | ADIIAIQETW | (23) | GGGVAVLVRK (31) DLIVASAYMRPPP |
| R1Bm | ..MDIRPRLPIGQINLGGA | (15) | LDIVLVQEQY | (13) | KAGVYIRNRV (22) DLYMVSAYFQYSD |
| FDm | ....IMATLFIATWNANGV | (15) | IDVMLLSETH | (23) | HGGTAILIRN (32) LLTLAAVYCPPRF |
| GDm | ....MQISLNIVFWNANGL | (15) | IDILLVSESH | (24) | RGGAAMLIKS (27) DITVGAVYPRHEF |
| JOCK | ...MTQPTLKIGLWNARGL | (15) | IDVMLTTETH | (24) | RGGSAVIIKS (27) TVTVAAVYLPPAE |
| IDm | .....MSLTVIQWNLKGY | (15) | PHIISLQETH | (23) | FGGVRILVHK (24) KLNIFSTYISPTK |
| L1Hs | .MTGSNSHITILTLNINGL | (17) | PSVCCIQETH | (25) | KAGVAILVSD (27) ELTILNIYAPNTG |
| Tx1 | ....MALSISTLNTNGC | (17) | YSVSFLQETH | (25) | SCGVVTLFSD (27) TYNLMNVYAPTTG |
| Cin4 (10) | GYYPMNTNCCIFSWNVRGL | (17) | ATSVCLQETK | (27) | GASGGILIAC (29) VWDLTAVYGPQQE |
| Dre (04) | NKTIKKNTIRIGVWNVQGS | (17) | LDAALLTETN | (27) | QGVSQIIINT (23) QIKCTTIYAPAKS |
| APHs (53) | SPSGKPATLKICSWNVDGL | (16) | PDILCLQETK | (28) | GYSGVGLLSR (27) SFVLVTAYVPNAG |

Retrotransposons     12-17     13-27     22-31     6-23

AP endonucleases     15-17     23-28     27     27-28

DNase I ........MLKIAAFNIRTF (20) YDIVLIQEVR     (120)
L1Hs mutants           ↓            ↓
                 N14A         E43A

```
(23) NLVAVGDLNLHHPDWD  (29) GE.PTRLGNATRGERDGTIDHAWLS  (16) GSDHCPQEIWVQV
(17) PLLLCGDFNMHHPQWE  (25) GE.ITTARGTRER...SCIDLTWSK  (13) LSDHYVLTFTLHQ
(19) RVVTCADTNAHSPLWH  (35) GHLPTFSTANGE....SYVDVTLST  (14) SSDHRLIVFGVGG
(16) HFIAAGDYNAKHTHWG  (26) PGSPTYWPSDLN.KLPDLIDFAVTK (15) SSDHSPVLIHLRR
(16) RFIAAGDFNAKHSWWG  (24) TGEPTHWPSDPS.KQPDLLDIAICK (15) VSDHSAVNLLLNI
(16) KFIAGGDYNAKHAWWG  (24) TGEPTFYSYNPL.LTPSALDFFITC (15) SSDHLPILAVLHA
(16) PSLITGDFNGWHPSWG  (24) DKSPTHFSTH...NTYSHIDLTLCS (16) GSDHFPIITTLFP
(18) HTLIMGDFNTPLSTLD  (34) TE.YTF..FSAPHHTYSKIDHIVGS (16) LSDHSAIKLELRI
(21) ALIIGGDFNYTLDARD  (34) VA.FTYVRVRDGHVSQSRIDRIYIS (16) FSDHNCVSLRMSI
(19) EWLILGDFNMIRRVGE  (30) KK.FT.WSNEQDDPTMSRIDRLMAT (16) TSDHSPLLMQGHS
(17) SDIITGDFNVDCSVDN  (19) NG.ITFPR.....NKSTIDRVFVS  (17) KSDHNMVIIELKI
(27) PLVLCGDLNVAHEEID  (45) TF.WTYMMNARSKNVGWRLDYFLLS (17) GSDHCPITLYLAL 21-35                              13-18
                       44-50                              17-21

DVMLMGDFNADCSYVT (31) ..................CAYDRIVVA (31) ISDHYPVEVTLT
     ↓                                   ↓                  ↓
    D145A                               D205G              H230A
```

FIG. 7Bii

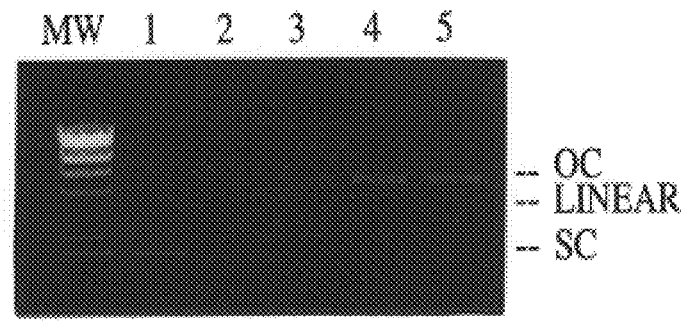
Fig. 11B
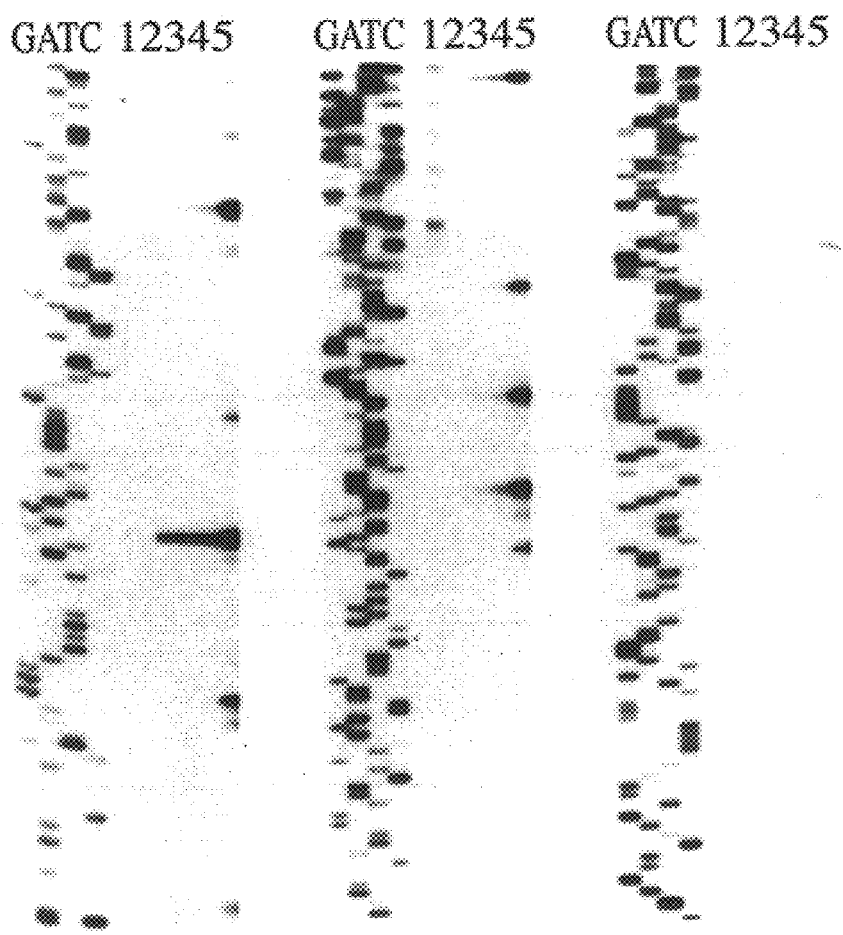
Fig. 11Ci   Fig. 11Cii   Fig. 11Ciii

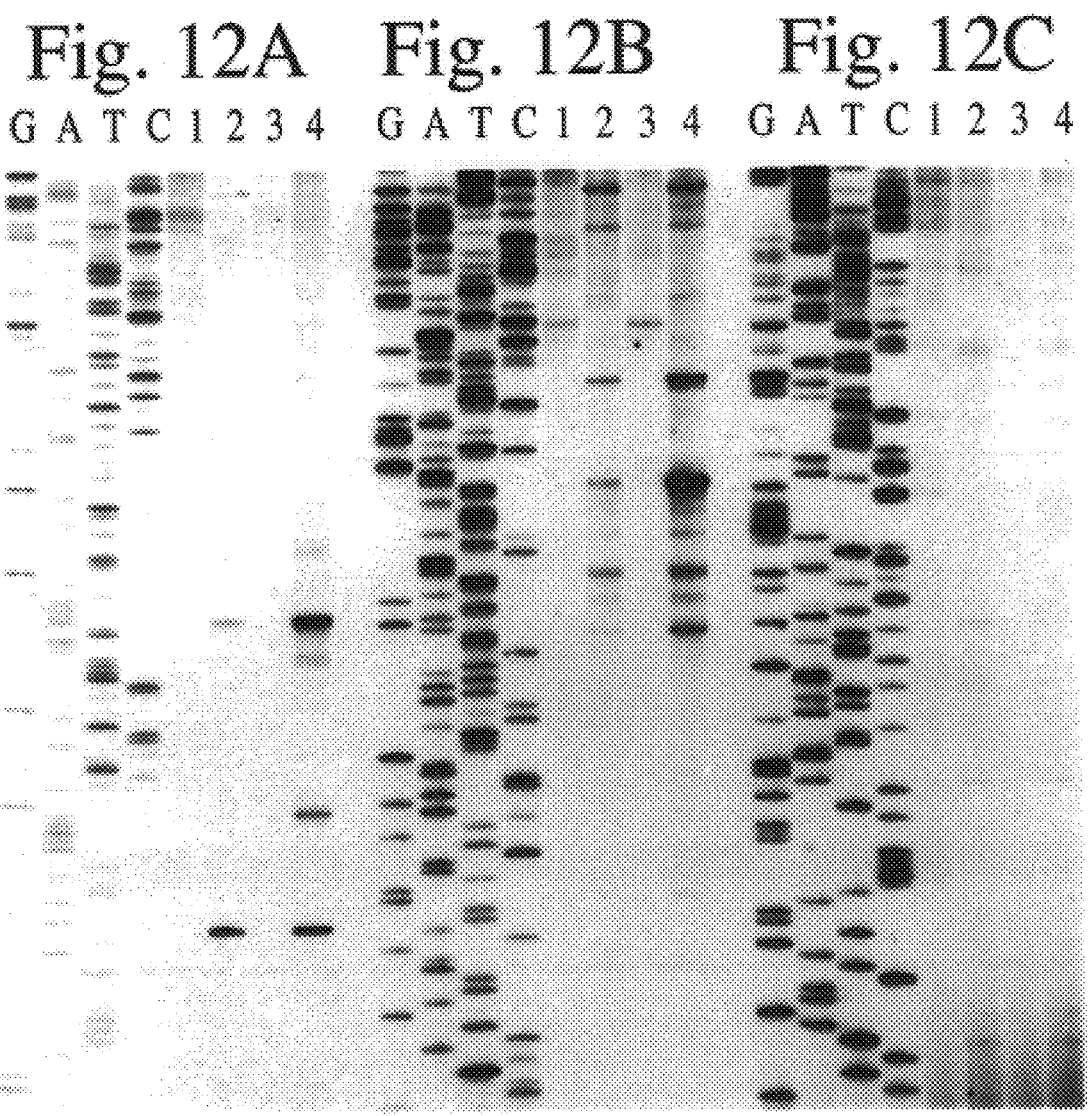

FIG. 14Bii

```
AGGATCTcaagaag
TCCT AGA gttcttc
     ↑

AAGTTTTaaatcaa
TTC AAAA tttagtt
     ↑

GAAGTTTtaaatca
CTT CAAA atttagt
     ↑

TCCTTTTaaattaa
AGGAAAA tttaatt
     ↑

AGATAATcaaaaaag
TCTATT A gttttttc
     ↑

TCAATCTaaagtat
AGTT AGA tttcata
     ↑
```

FIG. 14Bi

```
ATAATCTcatgacc
TATT AGA gtactgg
      ↑

CATTTTaatttaa
GT AAAAA ttaaatt
      ↑

TCATTTTaattta
AGT AAAA attaaat
      ↑

AAAATCCttaacg
TTTT AGG gaattgc
      ↑

AAGATCCttttga
TTCT AGG aaaact
      ↑

GAGTTTTcgttcca
CTC AAAA gcaaggt
      ↑
```

```
CTTTTaaaaaaattgttttgaat
GAAAAttttaacaaactta  ←
```

JH-27

```
CATCTCTTTGTTaaagacaaacaaaac
GTAGAGAAACaaatttctgtttgttttg  ←
```

JH-28

```
ATTAATgtttcctttctttt
TAATTAcaaaggaagaaaa  ←
```

DYSTROPHIN

```
GCAGTTaaatcatctgctgct
CGTCAAtttagtagacgacga  ←
```

APC

```
GGAATTaagaataatg
CCTTAAttcttattac  ←
```

FIG. 14D

```
A    TTTTTTaaTGTCAACTC
     AAAAAA ttACAGTTGAG
           ↑

B    TCTATTaaaaaggaaaaa (+207 bp)
     AGAT AA ttttt cttttt
         ↑

D    AAGAATaaattttcttttt (+21 bp)
     TTCTT A tttaaaagaaaa
          ↑
```

FIG. 14E

```
L1.2     AGTGGTgaaagtgggcattct
(LRE-1)  TCACC A ctttcacccgtaaga
              ↑

LRE-2    TGAGCTaagatcacaccactg
         ACTC GA ttctagtgtggtgac
              ↑
```

FIG. 14F

L1.1
```
GTGTTTtaacttagtaaca
CAC AAA atttgaatcattgt  ←
```

L1.3
```
TCTGATaagaataatagga
AGACTA A ttcttattatcct  ←
```

L1.4
```
GTATTTaaaaaa
CAT AAA tttttt  ←
```

CGL1.1
```
ATATATaagaggattaccag
TATATA A ttctcctaatggtc  ←
```

Z73497
```
ATACAcaaatttggacccaaagagag
TATGT G ttaaacctgggtttctctc  ←
```

FIG. 14G

```
L05637    TTTTTTaaaaaa
          AAAAAAtttttt
                ↑

Z70758    TGACTTagaagtccatgaatcca
          ACTGAAtcttcaggtacttaggt
              ↑

Z69721    TGCCTTaagaaggtcaaaggcag
          ACGGAAttcttcagtttcgtc
              ↑

Z69648    AAAACaaaaaa
          TTTTTGtttttt
               ↑

Z68163    AAAATTaaaattgtgat
          TTTTAAttttaactcta
              ↑

Z68339    GGGGTTaagattgaagaatg
          CCCCAAttctaacttcttac
              ↑

Z70042    GGATTCaaaaggagttattgat
          CCTAAGttttcctcaataacta
              ↑

Z68746    TCTTATaaaaagtaaact
          AGAATAttttcatttga
              ↑
```

| CONSTRUCT | | TRANSPOSITION FREQUENCY ($10^{-6}$ cell$^{-1}$) |
|---|---|---|
| WILDTYPE L1 | | 335 |
| D703Y | (RT$^-$) | 0.5 |
| N14 | (EN$^-$) | 3.4 |
| D145A | (EN$^-$) | 1.0 |
| D205G | (EN$^-$) | 0.7 |
| H230A | (EN$^-$) | 1.3 |

FIG. 15B

SEQUENCE LISTING (1) GENERAL INFORMATION:

(iii) NUMBER OF SEQUENCES: 137

(2) INFORMATION FOR SEQ ID NO:1:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Met Val Gln Leu Lys Ile Leu Tyr Trp Asn Val Gly Lys Ser
1               5                   10

(2) INFORMATION FOR SEQ ID NO:2:

```
     (i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:2:

Tyr Asp Ile Val Ala Ile Gln Glu Pro Gly
1               5                   10

(2) INFORMATION FOR SEQ ID NO:3:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:3:

Lys Gly Arg Ala Val Ile Tyr Val Asn Lys
1               5                   10

(2) INFORMATION FOR SEQ ID NO:4:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:4:

Pro Thr Thr Val Tyr Ser Ile Tyr Ser Pro Ile Leu Thr
1               5                   10

(2) INFORMATION FOR SEQ ID NO:5:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:5:

Asn Leu Val Ala Val Gly Asp Leu Asn Leu His His Pro Asp Trp Asp
1               5                   10                  15

(2) INFORMATION FOR SEQ ID NO:6:

(i) SEQUENCE CHARACTERISTICS:
         (A) LENGTH: 24 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:6:

Gly Glu Pro Thr Arg Leu Gly Asn Ala Thr Arg Gly Glu Arg Asp Gly
1               5                   10                  15

Thr Ile Asp His Ala Trp Leu Ser
```

20

(2) INFORMATION FOR SEQ ID NO:7:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Gly Ser Asp His Cys Pro Gln Glu Ile Trp Val Gln Val
1              5                    10

(2) INFORMATION FOR SEQ ID NO:8:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Asp Ile Glu Gln Asn Pro Gly Pro Ile Ala Val Leu Gln Met Asn Val
1              5                    10                  15

Ser Cys Leu (2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Ala Asp Ile Ile Ala Ile Gln Glu Thr Trp
1              5                    10

(2) INFORMATION FOR SEQ ID NO:10:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Gly Gly Gly Val Ala Val Leu Val Arg Lys
1              5                    10

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Asp Leu Ile Val Ala Ser Ala Tyr Met Arg Pro Pro Pro
1               5                  10

(2) INFORMATION FOR SEQ ID NO:12:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:12:

Pro Leu Leu Leu Cys Gly Asp Phe Asn Met His His Pro Gln Trp Glu
1               5                  10                  15

(2) INFORMATION FOR SEQ ID NO:13:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:13:

Gly Glu Ile Thr Thr Ala Arg Gly Thr Arg Glu Arg Ser Cys Ile Asp
1               5                  10                  15

Leu Thr Trp Ser Lys
            20

(2) INFORMATION FOR SEQ ID NO:14:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:14:

Leu Ser Asp His Tyr Val Leu Thr Phe Thr Leu His Gln
1               5                  10

(2) INFORMATION FOR SEQ ID NO:15:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:15:

Met Asp Ile Arg Pro Arg Leu Pro Ile Gly Gln Ile Asn Leu Gly Gly
1               5                  10                  15

Ala (2) INFORMATION FOR SEQ ID NO:16:

(i) SEQUENCE CHARACTERISTICS:
            (A) LENGTH: 10 amino acids (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:16:

Leu Asp Ile Val Leu Val Gln Glu Gln Tyr
1               5                   10

(2) INFORMATION FOR SEQ ID NO:17:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:17:

Lys Ala Gly Val Tyr Ile Arg Asn Arg Val
1               5                   10

(2) INFORMATION FOR SEQ ID NO:18:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:18:

Asp Leu Tyr Met Val Ser Ala Tyr Phe Gln Tyr Ser Asp
1               5                   10

(2) INFORMATION FOR SEQ ID NO:19:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:19:

Arg Val Val Ile Cys Ala Asp Thr Asn Ala His Ser Pro Leu Trp His
1               5                   10                  15

(2) INFORMATION FOR SEQ ID NO:20:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:20:

Gly His Leu Pro Thr Phe Ser Thr Ala Asn Gly Glu Ser Tyr Val Asp
1               5                   10                  15

Val Thr Leu Ser Thr
            20

(2) INFORMATION FOR SEQ ID NO:21:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

Ser Ser Asp His Arg Leu Ile Val Phe Gly Val Gly Gly
1               5                   10

(2) INFORMATION FOR SEQ ID NO:22:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

Ile Met Ala Thr Leu Phe Ile Ala Thr Trp Asn Ala Asn Gly Val
1               5                   10                  15

(2) INFORMATION FOR SEQ ID NO:23:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

Ile Asp Val Met Leu Leu Ser Glu Thr His
1               5                   10

(2) INFORMATION FOR SEQ ID NO:24:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

His Gly Gly Thr Ala Ile Leu Ile Arg Asn
1               5                   10

(2) INFORMATION FOR SEQ ID NO:25:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

Leu Leu Thr Leu Ala Ala Val Tyr Cys Pro Pro Arg Phe
1               5                   10

(2) INFORMATION FOR SEQ ID NO:26:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:26:

```
His Phe Ile Ala Ala Gly Asp Tyr Asn Ala Lys His Thr His Trp Gly
1               5                  10                  15
```

(2) INFORMATION FOR SEQ ID NO:27:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

```
Pro Gly Ser Pro Thr Tyr Trp Pro Ser Asp Leu Asn Lys Leu Pro Asp
1               5                  10                  15
Leu Ile Asp Phe Ala Val Thr Lys
            20
```

(2) INFORMATION FOR SEQ ID NO:28:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

```
Ser Ser Asp His Ser Pro Val Leu Ile His Leu Arg Arg
1               5                  10
```

(2) INFORMATION FOR SEQ ID NO:29:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

```
Met Gln Ile Ser Leu Asn Ile Val Phe Trp Asn Ala Asn Gly Leu
1               5                  10                  15
```

(2) INFORMATION FOR SEQ ID NO:30:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

```
Ile Asp Ile Leu Leu Val Ser Glu Ser His
1               5                  10
```

(2) INFORMATION FOR SEQ ID NO:31:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

```
Arg Gly Gly Ala Ala Met Leu Ile Lys Ser
1               5                  10
```

(2) INFORMATION FOR SEQ ID NO:32:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

```
Asp Ile Thr Val Gly Ala Val Tyr Pro Arg His Glu Phe
1               5                  10
```

(2) INFORMATION FOR SEQ ID NO:33:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

```
Arg Phe Ile Ala Ala Gly Asp Phe Asn Ala Lys His Ser Trp Trp Gly
1               5                  10                  15
```

(2) INFORMATION FOR SEQ ID NO:34:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

```
Thr Gly Glu Pro Thr His Trp Pro Ser Asp Pro Ser Lys Gln Pro Asp
1               5                  10                  15
Leu Leu Asp Ile Ala Ile Cys Lys
                20
```

(2) INFORMATION FOR SEQ ID NO:35:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Val Ser Asp His Ser Ala Val Asn Leu Leu Asn Ile
1               5                  10

(2) INFORMATION FOR SEQ ID NO:36:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:36:

Met Thr Gln Pro Thr Leu Lys Ile Gly Leu Trp Asn Ala Arg Gly Leu
1               5                  10                  15

(2) INFORMATION FOR SEQ ID NO:37:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:37:

Ile Asp Val Met Leu Thr Thr Glu Thr His
1               5                  10

(2) INFORMATION FOR SEQ ID NO:38:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:38:

Arg Gly Gly Ser Ala Val Ile Ile Lys Ser
1               5                  10

(2) INFORMATION FOR SEQ ID NO:39:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:39:

Thr Val Thr Val Ala Ala Val Tyr Leu Pro Pro Ala Glu
1               5                  10

(2) INFORMATION FOR SEQ ID NO:40:

(i) SEQUENCE CHARACTERISTICS:
            (A) LENGTH: 16 amino acids
            (B) TYPE: amino acid
            (C) STRANDEDNESS: single (D) TOPOLOGY: linear (ii) MOLECULE TYPE: protein (xi) SEQUENCE DESCRIPTION: SEQ ID NO:40:

Lys Phe Ile Ala Gly Gly Asp Tyr Asn Ala Lys His Ala Trp Trp Gly
1               5                  10                  15

(2) INFORMATION FOR SEQ ID NO:41:

(i) SEQUENCE CHARACTERISTICS:
          (A) LENGTH: 24 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:41:

Thr Gly Glu Pro Thr Phe Tyr Ser Tyr Asn Pro Leu Leu Thr Pro Ser
1               5                  10                  15

Ala Leu Asp Phe Phe Ile Thr Cys
            20

(2) INFORMATION FOR SEQ ID NO:42:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:42:

Ser Ser Asp His Leu Pro Ile Leu Ala Val Leu His Ala
1               5                  10

(2) INFORMATION FOR SEQ ID NO:43:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:43:

Met Ser Leu Thr Val Ile Gln Trp Asn Leu Lys Gly Tyr
1               5                  10

(2) INFORMATION FOR SEQ ID NO:44:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:44:

Pro His Ile Ile Ser Leu Gln Glu Thr His
1               5                  10

(2) INFORMATION FOR SEQ ID NO:45:

```
    (i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

Phe Gly Gly Val Arg Ile Leu Val His Lys
1               5                   10

(2) INFORMATION FOR SEQ ID NO:46:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:46:

Lys Leu Asn Ile Phe Ser Thr Tyr Ile Ser Pro Thr Lys
1               5                   10

(2) INFORMATION FOR SEQ ID NO:47:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

Pro Ser Leu Ile Thr Gly Asp Phe Asn Gly Trp His Pro Ser Trp Gly
1               5                   10                  15

(2) INFORMATION FOR SEQ ID NO:48:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

Asp Lys Ser Pro Thr His Phe Ser Thr His Asn Thr Tyr Ser His Ile
1               5                   10                  15

Asp Leu Thr Leu Cys Ser
                20

(2) INFORMATION FOR SEQ ID NO:49:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

Gly Ser Asp His Phe Pro Ile Ile Thr Thr Leu Phe Pro
1               5                   10
```

(2) INFORMATION FOR SEQ ID NO:50:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

```
Met Thr Gly Ser Asn Ser His Ile Thr Ile Leu Thr Leu Asn Ile Asn
1               5                   10                  15
Gly Leu
```

(2) INFORMATION FOR SEQ ID NO:51:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:51:

```
Pro Ser Val Cys Cys Ile Gln Glu Thr His
1               5                   10
```

(2) INFORMATION FOR SEQ ID NO:52:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:52:

```
Lys Ala Gly Val Ala Ile Leu Val Ser Asp
1               5                   10
```

(2) INFORMATION FOR SEQ ID NO:53:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

```
Glu Leu Thr Ile Leu Asn Ile Tyr Ala Pro Asn Thr Gly
1               5                   10
```

(2) INFORMATION FOR SEQ ID NO:54:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:54:

```
His Thr Leu Ile Met Gly Asp Phe Asn Thr Pro Leu Ser Thr Leu Asp
1               5                   10                  15
```

(2) INFORMATION FOR SEQ ID NO:55:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:55:

```
Thr Glu Tyr Thr Phe Phe Ser Ala Pro His His Thr Tyr Ser Lys Ile
1               5                   10                  15
Asp His Ile Val Gly Ser
            20
```

(2) INFORMATION FOR SEQ ID NO:56:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:56:

```
Leu Ser Asp His Ser Ala Ile Lys Leu Glu Leu Arg Ile
1               5                   10
```

(2) INFORMATION FOR SEQ ID NO:57:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:57:

```
Met Ala Leu Ser Ile Ser Thr Leu Asn Thr Asn Gly Cys
1               5                   10
```

(2) INFORMATION FOR SEQ ID NO:58:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:58:

```
Tyr Ser Val Ser Phe Leu Gln Glu Thr His
1               5                   10
```

(2) INFORMATION FOR SEQ ID NO:59:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

Ser Cys Gly Val Val Thr Leu Phe Ser Asp
1               5                   10

(2) INFORMATION FOR SEQ ID NO:60:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:60:

Thr Tyr Asn Leu Met Asn Val Tyr Ala Pro Thr Thr Gly
1               5                   10

(2) INFORMATION FOR SEQ ID NO:61:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:61:

Ala Leu Ile Ile Gly Gly Asp Phe Asn Tyr Thr Leu Asp Ala Arg Asp
1               5                   10                  15

(2) INFORMATION FOR SEQ ID NO:62:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:62:

Val Ala Phe Thr Tyr Val Arg Val Arg Asp Gly His Val Ser Gln Ser
1               5                   10                  15
Arg Ile Asp Arg Ile Tyr Ile Ser
            20

(2) INFORMATION FOR SEQ ID NO:63:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:63:

Phe Ser Asp His Asn Cys Val Ser Leu Arg Met Ser Ile
1               5                   10

(2) INFORMATION FOR SEQ ID NO:64:

(i) SEQUENCE CHARACTERISTICS:

(A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:64:

Gly Tyr Tyr Pro Met Asn Thr Asn Cys Cys Ile Phe Ser Trp Asn Val
1               5                  10                  15

Arg Gly Leu (2) INFORMATION FOR SEQ ID NO:65:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:65:

Ala Thr Ser Val Cys Leu Gln Glu Thr Lys
1               5                  10

(2) INFORMATION FOR SEQ ID NO:66:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:66:

Gly Ala Ser Gly Gly Ile Leu Ile Ala Cys
1               5                  10

(2) INFORMATION FOR SEQ ID NO:67:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:67:

Val Trp Asp Leu Thr Ala Val Tyr Gly Pro Gln Gln Glu
1               5                  10

(2) INFORMATION FOR SEQ ID NO:68:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:68:

Glu Trp Leu Ile Leu Gly Asp Phe Asn Met Ile Arg Arg Val Gly Glu
1               5                  10                  15

(2) INFORMATION FOR SEQ ID NO:69:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:69:

Lys Lys Phe Thr Trp Ser Asn Glu Gln Asp Asp Pro Thr Met Ser Arg
1               5                   10                  15

Ile Asp Arg Leu Met Ala Thr
            20

(2) INFORMATION FOR SEQ ID NO:70:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:70:

Thr Ser Asp His Ser Pro Leu Leu Met Gln Gly His Ser
1               5                   10

(2) INFORMATION FOR SEQ ID NO:71:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:71:

Asn Lys Thr Ile Lys Lys Asn Thr Ile Arg Ile Gly Val Trp Asn Val
1               5                   10                  15

Gln Gly Ser (2) INFORMATION FOR SEQ ID NO:72:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:72:

Leu Asp Ala Ala Leu Leu Thr Glu Thr Asn
1               5                   10

(2) INFORMATION FOR SEQ ID NO:73:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:73:

Gln Gly Val Ser Gln Ile Ile Ile Asn Thr
1               5                   10

(2) INFORMATION FOR SEQ ID NO:74:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:74:

Gln Ile Lys Cys Thr Thr Ile Tyr Ala Pro Ala Lys Ser
1               5                   10

(2) INFORMATION FOR SEQ ID NO:75:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:75:

Ser Asp Ile Ile Thr Gly Asp Phe Asn Val Asp Cys Ser Val Asp Asn
1               5                   10                  15

(2) INFORMATION FOR SEQ ID NO:76:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:76:

Asn Gly Ile Thr Phe Pro Arg Asn Lys Ser Thr Ile Asp Arg Val Phe
1               5                   10                  15

Val Ser (2) INFORMATION FOR SEQ ID NO:77:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:77:

Lys Ser Asp His Asn Met Val Ile Ile Glu Leu Lys Ile
1               5                   10

(2) INFORMATION FOR SEQ ID NO:78:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:78:

Ser Pro Ser Gly Lys Pro Ala Thr Leu Lys Ile Cys Ser Trp Asn Val
1               5                   10                  15

Asp Gly Leu (2) INFORMATION FOR SEQ ID NO:79:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:79:

Pro Asp Ile Leu Cys Leu Gln Glu Thr Lys
1               5                   10

(2) INFORMATION FOR SEQ ID NO:80:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:80:

Gly Tyr Ser Gly Val Gly Leu Leu Ser Arg
1               5                   10

(2) INFORMATION FOR SEQ ID NO:81:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:81:

Ser Phe Val Leu Val Thr Ala Tyr Val Pro Asn Ala Gly
1               5                   10

(2) INFORMATION FOR SEQ ID NO:82:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:82:

Pro Leu Val Leu Cys Gly Asp Leu Asn Val Ala His Glu Glu Ile Asp
1               5                   10                  15

(2) INFORMATION FOR SEQ ID NO:83:

(i) SEQUENCE CHARACTERISTICS:
            (A) LENGTH: 24 amino acids

```
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:83:

Thr Phe Trp Thr Tyr Met Met Asn Ala Arg Ser Lys Asn Val Gly Trp
1               5                   10                  15

Arg Leu Asp Tyr Phe Leu Leu Ser
            20

(2) INFORMATION FOR SEQ ID NO:84:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:84:

Gly Ser Asp His Cys Pro Ile Thr Leu Tyr Leu Ala Leu
1               5                   10

(2) INFORMATION FOR SEQ ID NO:85:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:85:

Met Leu Lys Ile Ala Ala Phe Asn Ile Arg Thr Phe
1               5                   10

(2) INFORMATION FOR SEQ ID NO:86:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:86:

Tyr Asp Ile Val Leu Ile Gln Glu Val Arg
1               5                   10

(2) INFORMATION FOR SEQ ID NO:87:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:87:

Asp Val Met Leu Met Gly Asp Phe Asn Ala Asp Cys Ser Tyr Val Thr
1               5                   10                  15
```

(2) INFORMATION FOR SEQ ID NO:88:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:88:

```
Cys Ala Tyr Asp Arg Ile Val Val Ala
1               5
```

(2) INFORMATION FOR SEQ ID NO:89:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:89:

```
Ile Ser Asp His Tyr Pro Val Glu Val Thr Leu Thr
1               5                   10
```

(2) INFORMATION FOR SEQ ID NO:90:

(i) SEQUENCE CHARACTERISTICS:
        (A) LENGTH: 164 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:90:

```
AAAAAAGGA TCTCAAGAAG ATCCTTTGAT CTTTTCTACG GGGTCTGACG CTCAGTGGAA      60

CGAAAACTCA CGTTAAGGGA TTTTGGTCAT GAGATTATCA AAAGGATCT TCACCTAGAT     120

CCTTTTAAAT TAAAAATGAA GTTTTAAATC AATCTAAAGT ATAT                     164
```

(2) INFORMATION FOR SEQ ID NO:91:

(i) SEQUENCE CHARACTERISTICS:
        (A) LENGTH: 220 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:91:

```
GAGGCCTAAA ATTCCAACCG AAAATCGCGA GGTTACTTTT TTGGAGCCCG AAAACCACCC      60

AAAATCAAGG AAAAATGGCC AAAAAATGCC AAAAAATAGC GAAAATACCC CGAAAATTGG    120

CAAAAATTAA CAAAAAATAG CGAATTTCCC TGAATTTTAG GCGAAAAAAC CCCCGAAAAT    180

GGCCAAAAAC GCACTGAAAA TCAAAATCTG AACGTCTACG                         220
```

(2) INFORMATION FOR SEQ ID NO:92:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:92:

CTTTTTAAAA AAATTGTTT                                                    19

(2) INFORMATION FOR SEQ ID NO:93:

(i) SEQUENCE CHARACTERISTICS:
              (A) LENGTH: 13 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:93:

TTTTTTTAAC AAA                                                          13

(2) INFORMATION FOR SEQ ID NO:94:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: RNA (genomic)

(xi) SEQUENCE DESCRIPTION: SEQ ID NO:94:

AAAAAAAAAA AAAAAAAAAA AA                                                22

(2) INFORMATION FOR SEQ ID NO:95:

(i) SEQUENCE CHARACTERISTICS:
              (A) LENGTH: 14 base pairs
              (B) TYPE: nucleic acid
              (C) STRANDEDNESS: double
              (D) TOPOLOGY: linear (ii) MOLECULE TYPE: DNA (genomic)

(xi) SEQUENCE DESCRIPTION: SEQ ID NO:95:

ATAATCTCAT GACC                                                         14

(2) INFORMATION FOR SEQ ID NO:96:

(i) SEQUENCE CHARACTERISTICS:
              (A) LENGTH: 14 base pairs
              (B) TYPE: nucleic acid
              (C) STRANDEDNESS: double
              (D) TOPOLOGY: linear (ii) MOLECULE TYPE: DNA (genomic)

(xi) SEQUENCE DESCRIPTION: SEQ ID NO:96:

CATTTTTAAT TTAA                                                         14

(2) INFORMATION FOR SEQ ID NO:97:

(i) SEQUENCE CHARACTERISTICS:
              (A) LENGTH: 14 base pairs
              (B) TYPE: nucleic acid
              (C) STRANDEDNESS: double
              (D) TOPOLOGY: linear (ii) MOLECULE TYPE: DNA (genomic)

(xi) SEQUENCE DESCRIPTION: SEQ ID NO:97:

TCATTTTTAA TTTA                                       14

(2) INFORMATION FOR SEQ ID NO:98:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:98:

AAAATCCCTT AACG                                       14

(2) INFORMATION FOR SEQ ID NO:99:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:99:

AAGATCCTTT TTGA                                       14

(2) INFORMATION FOR SEQ ID NO:100:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:100:

GAGTTTTCGT TCCA                                       14

(2) INFORMATION FOR SEQ ID NO:101:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:101:

AGGATCTCAA GAAG                                       14

(2) INFORMATION FOR SEQ ID NO:102:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:102:

AAGTTTTAAA TCAA                                       14

(2) INFORMATION FOR SEQ ID NO:103:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:103:

GAAGTTTTAA ATCA                                                         14

(2) INFORMATION FOR SEQ ID NO:104:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:104:

TCCTTTTAAA TTAA                                                         14

(2) INFORMATION FOR SEQ ID NO:105:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:105:

AGATAATCAA AAAAG                                                        15

(2) INFORMATION FOR SEQ ID NO:106:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:106:

TCAATCTAAA GTAT                                                         14

(2) INFORMATION FOR SEQ ID NO:107:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:107:

CTTTTTAAAA AAATTGTTTG AAT                                               23

(2) INFORMATION FOR SEQ ID NO:108:

(i) SEQUENCE CHARACTERISTICS:
        (A) LENGTH: 27 base pairs (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:108:

CATCTCTTTG TTAAAGACAA ACAAAAC                                          27

(2) INFORMATION FOR SEQ ID NO:109:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:109:

ATTAATGTTT CCTTCTTTT                                                   19

(2) INFORMATION FOR SEQ ID NO:110:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:110:

GCAGTTAAAT CATCTGCTGC T                                                21

(2) INFORMATION FOR SEQ ID NO:111:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:111:

GGAATTAAGA ATAATG                                                      16

(2) INFORMATION FOR SEQ ID NO:112:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:112:

TTTTTTAATG TCAACTC                                                     17

(2) INFORMATION FOR SEQ ID NO:113:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:113:

TCTATTAAAA AGGAAAAA                                                         18

(2) INFORMATION FOR SEQ ID NO:114:

(i) SEQUENCE CHARACTERISTICS:
            (A) LENGTH: 19 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:114:

AAGAATAAAT TTTCTTTTT                                                        19

(2) INFORMATION FOR SEQ ID NO:115:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:115:

AGTGGTGAAA GTGGGCATTC T                                                     21

(2) INFORMATION FOR SEQ ID NO:116:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:116:

TGAGCTAAGA TCACACCACT G                                                     21

(2) INFORMATION FOR SEQ ID NO:117:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:117:

GTGTTTTAAA CTTAGTAACA                                                       20

(2) INFORMATION FOR SEQ ID NO:118:

(i) SEQUENCE CHARACTERISTICS:
            (A) LENGTH: 19 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:118:

```
TCTGATAAGA ATAATAGGA                                                    19

(2) INFORMATION FOR SEQ ID NO:119:

(i) SEQUENCE CHARACTERISTICS:
         (A) LENGTH: 12 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:119:

GTATTTAAAA AA                                                           12

(2) INFORMATION FOR SEQ ID NO:120:

(i) SEQUENCE CHARACTERISTICS:
         (A) LENGTH: 20 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:120:

ATATATAAGA GGATTACCAG                                                   20

(2) INFORMATION FOR SEQ ID NO:121:

(i) SEQUENCE CHARACTERISTICS:
         (A) LENGTH: 26 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:121:

ATACACAAAT TTGGACCCAA AGAGAG                                            26

(2) INFORMATION FOR SEQ ID NO:122:

(i) SEQUENCE CHARACTERISTICS:
         (A) LENGTH: 12 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:122:

TTTTTTAAAA AA                                                           12

(2) INFORMATION FOR SEQ ID NO:123:

(i) SEQUENCE CHARACTERISTICS:
         (A) LENGTH: 23 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:123:

TGACTTAGAA GTCCATGAAT CCA                                               23

(2) INFORMATION FOR SEQ ID NO:124:
```

(i) SEQUENCE CHARACTERISTICS:
    (A) LENGTH: 23 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:124:

TGCCTTAAGA AGGTCAAAGG CAG                                      23

(2) INFORMATION FOR SEQ ID NO:125:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:125:

AAAAACAAAA AA                                                  12

(2) INFORMATION FOR SEQ ID NO:126:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:126:

AAAATTAAAA ATTGTGAT                                            18

(2) INFORMATION FOR SEQ ID NO:127:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:127:

GGGGTTAAGA TTGAAGAATG                                          20

(2) INFORMATION FOR SEQ ID NO:128:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:128:

GGATTCAAAA GGAGTTATTG AT                                       22

(2) INFORMATION FOR SEQ ID NO:129:

(i) SEQUENCE CHARACTERISTICS:
        (A) LENGTH: 18 base pairs
        (B) TYPE: nucleic acid

```
        (C) STRANDEDNESS: double
        (D) TOPOLOGY: linear (ii) MOLECULE TYPE: DNA (genomic)

(xi) SEQUENCE DESCRIPTION: SEQ ID NO:129:

TCTTATAAAA AGTAAACT                                                    18

(2) INFORMATION FOR SEQ ID NO:130:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:130:

Ala Cys Asp Glu Phe Gly
1               5

(2) INFORMATION FOR SEQ ID NO:131:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:131:

Ala Cys Asp His Ile Lys
1               5

(2) INFORMATION FOR SEQ ID NO:132:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:132:

CCTCATGACA GGATCAAATT CACAC                                            25

(2) INFORMATION FOR SEQ ID NO:133:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:133:

GCCCATGGCA ATCCTGAGTT CTAGTTTG                                         28

(2) INFORMATION FOR SEQ ID NO:134:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

```
       (ii) MOLECULE TYPE: DNA (genomic)

(xi) SEQUENCE DESCRIPTION: SEQ ID NO:134:

TCTTTTCTAC GGGGTCTG                                                    18

(2) INFORMATION FOR SEQ ID NO:135:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:135:

CAGGCAACTA TGGATGAA                                                    18

(2) INFORMATION FOR SEQ ID NO:136:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:136:

AATACGACTC ACTATAG                                                     17

(2) INFORMATION FOR SEQ ID NO:137:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:137:

AGCTATTTAG GTGACACTAT AG                                               22
```

COMPOSITIONS AND METHODS OF USE OF MAMMALIAN RETROTRANSPOSONS

CROSS REFERENCE TO RELATED APPLICATIONS

This application is a continuation-in-part application of copending application No. 08/749,805, filed on Nov. 15, 1996, now abandoned which claims priority under 35 U.S.C. §119(e) to U.S. Provisional Application No. 60/006,831, filed on Nov. 16, 1995.

GOVERNMENT SUPPORT

This invention was supported in part by funds from the U.S. Government (NIH Grant Nos. GM45398, GM36481 and CA16519) and the U.S. Government may therefore have certain rights in the invention.

BACKGROUND OF THE INVENTION

Retrotransposons are naturally occuring DNA elements which are found in cells from almost all species of animals, plants and bacteria which have been examined to date. They are characterized in that they are capable of being expressed in cells, can be reverse transcribed into an extrachromosomal element and can reintegrate into another site on the same genome from which they originated.

Retrotransposons may be grouped into two classes, the retrovirus-like LTR retrotransposons, and the poly A elements such as human L1 elements, Neurospora TAD elements (Kinsey, 1990, *Genetics* 126:317–326), I factors from Drosophila (Bucheton et al., 1984, *Cell* 38:153–163), and R2Bm from *Bombyx mori* (Luan et al., 1993, *Cell* 72: 595–605). These two types of retrotransposon are structurally different and also retrotranspose using radically different mechanisms.

Unlike the LTR retrotransposons, poly A elements (also called non-LTR elements) lack LTRs and instead end with poly A or A-rich sequences. The LTR retrotransposition mechanism is relatively well-understood; in contrast, the mechanism of retrotransposition by poly A retrotransposons has just begun to be elucidated (Luan and Eickbush, 1995, *Mol. Cell. Biol.* 15:3882–3891; Luan et al., 1993, *Cell* 72:595–605). Poly A retrotransposons can be subdivided into sequence-specific and non-sequence-specific types. L1 is of the latter type being found to be inserted in a scattered manner in all human, mouse and other mammalian chromosomes.

The L1 element (also known as a LINE) has been extremely successful at colonizing the human genome. Early approximations estimated that L1s are present at 100,000 copies in the human genome and comprise 5% of nuclear DNA (Fanning and Singer, 1987, *Biochim Biophys Acta* 910:203–121). However, recent studies suggest that as many as 850,000 L1s may exist in the human genome (Smit et al., 1996, *Current Opinion in Genetics and Development*). Most of these copies are truncated at the 5' end and are presumed to be defective. Similar to full-length elements, the 5' truncated copies are often flanked by short target site duplications (TSDs). These features suggest that specific nucleotide sequences at the L1 5' end are not required for insertion in cis, and emphasize that transactions involving the 3' poly A terminus may be critical.

A 6.1 kb full-length L1 consensus sequence reveals the following conserved organization: A 5' untranslated leader region (UTR) with an internal promoter; two non-overlapping reading frames (ORF1 and ORF2); a 200 bp 3' UTR and a 3' poly A tail. ORF1 encodes a 40 kd protein and may serve a packaging function for the RNA (Martin, 1991, *Mol. Cell Biol.*11:4804–4807; Hohjoh et al., 1996, *EMBO J.* 15:630–639), while ORF2 encodes a reverse transcriptase (Mathias et al., 1991, *Science* 254:1808–1810). ORF1 and possibly ORF2 proteins associate with L1 RNA, forming a ribonucleoprotein particle. Reverse transcription by ORF2 protein must occur, resulting in L1 cDNAs, which are integrated into the genome (Martin, 1991, *Curr. Opin. Genet. Dev.* 1:505–508). Additionally, L1 elements are usually flanked by TSD's ranging from 7 to 20 bp. The full L1 and other poly A retrotransposons lack recognizable homologs of retroviral integrase, protease and RNase H. This group of elements employs a fundamentally different mechanism for transposition than the LTR-retrotransposons.

Some human L1 elements can retrotranspose (express, cleave their target site, and reverse transcribe their own RNA using the cleaved target site as a primer) into new sites in the human genome, leading to genetic disorders. Germ line L1 insertions into the factor VIII and dystrophin gene give rise to hemophilia A and muscular dystrophy, respectively (Kazazian et al., 1988, *Nature* 332:164–166; Narita et al., 1993, *J. Clinical Invest.* 91:1862–1867; Holmes et al., 1994, *Nature Genetics* 7:143–148), while somatic cell L1 insertions into the c-myc and APC tumor suppressor gene are implicated in rare cases of breast and colon cancer, respectively (Morse et al., *Nature* 333:87–90; Miki et al., 1992, *Cancer Research* 52:643–645). Thus, L1 is a potential mutagen and L1 retrotransposition is mutagenic.

BRIEF SUMMARY OF THE INVENTION

The invention relates to an isolated DNAc molecule comprising a promoter P and an L1 cassette sequence comprising a core L1 retrotransposon element.

In one embodiment, the core L1 retrotransposon element of the isolated DNAc molecule of the invention comprises a 5' UTR, ORF1, ORF2 comprising EN and RT domains, a 3' UTR, a poly A signal, and a vector sequence comprising at least one origin of DNA replication and a DNA sequence encoding at least one selectable marker protein.

In another embodiment, the promoter P in the isolated DNAc molecule of the invention is an RNA pol III promoter or an RNA pol II promoter, the RNA pol II promoter being selected from the group consisting of a constitutive promoter, an inducible promoter, a tissue-specific promoter and a viral promoter.

In yet another embodiment, the origin of DNA replication in the isolated DNAc molecule is a eukaryotic origin of DNA replication. The eukaryotic origin of DNA replication is selected from the group consisting of a viral origin of DNA replication, a yeast origin of DNA replication and a mammalian artificial chromosome.

The isolated DNAc molecule of the invention further comprises a prokaryotic origin of DNA replication. The prokaryotic origin of DNA replication is selected from the group consisting of a ColEI and a pA15 origin of DNA replication.

The selectable marker protein in the isolated DNAc molecule of the invention is a first marker protein selected from the group consisting of neomycin resistance protein, green fluorescent protein, β-galactosidase, and a prokaryotic antibiotic resistance protein.

In yet another embodiment, the isolated DNAc molecule of the invention further comprises a fragment of non-L1 DNA and a promoter P' for expression of the non-L1 DNA, wherein the non-L1 DNA and promoter P' are positioned within the 3' UTR or between the 3' UTR and the poly A signal. The promoter P' is an RNA pol III promoter or an RNA pol II promoter, the RNA pol II promoter being selected from the group consisting of a constitutive promoter, an inducible promoter, a tissue-specific promoter and a viral promoter.

In another embodiment, the non-L1 DNA comprises DNA encoding a second marker protein. The second marker protein is selected from the group consisting of neomycin resistance protein, green fluorescent protein, β-galactosidase, herpes simplex virus thymidine kinase and a eukaryotic cell surface protein.

In yet another embodiment of the invention, the non-L1 DNA in the isolated DNAc molecule comprises DNA encoding a protein capable of correcting a genetic defect in a cell. The protein is selected from the group consisting of cystic fibrosis transmembrane conductance regulator, β-globin, an enzyme, a tumor suppressor protein and a cytokine.

In another embodiment of the invention, the non-L1 DNA in the isolated DNAc molecule comprises tag DNA.

In another aspect of the invention, the invention relates to an isolated DNAc molecule comprising a promoter P and an L1 cassette sequence comprising a core L1 retrotransposon element, the core L1 retrotransposon element comprising a 5' UTR, ORF1, ORF2 comprising EN and RT domains, a 3' UTR, a poly A signal, a fragment of non-L1 DNA, a promoter P' for expression of the non-L1 DNA and a vector sequence comprising two origins of DNA replication and a DNA sequence encoding at least one selectable marker protein, wherein the promoter P comprises the cytomegalovirus immediate early promoter, wherein the non-L1 DNA comprises the neomycin resistance gene, and wherein one of the origins of DNA replication comprises the Epstein Barr virus origin of DNA replication and another of the origins of DNA replication comprises the ColE1 origin of DNA replication.

The invention also relates to a method of generating a cell mutant comprising transfecting a cell with an isolated DNAc molecule comprising a promoter P and an L1 cassette sequence comprising a core L1 retrotransposon element to effect integration of the core L1 retrotransposon element sequence into the genome of the cell thereby generating the cell mutant.

In addition, the invention includes a method of generating a library of cell mutants comprising transfecting a population of cells with an isolated DNAc molecule comprising a promoter P and an L1 cassette sequence comprising a core L1 retrotransposon element to effect random integration of the core L1 retrotransposon element independently into the genome of at least two of the cells in the cell population thereby generating a library of cell mutants. In one embodiment of this method of the invention, the core L1 retrotransposon element comprises non-L1 DNA suitable for PCR.

Also included in the invention is a method of isolating a host cell DNA fragment from a cell comprising transfecting the cell with an isolated DNAc molecule comprising a promoter P and an L1 cassette sequence comprising a core L1 retrotransposon element comprising non-L1 DNA, to effect random integration of the core L1 retrotransposon element into the genome of the cell, performing PCR on integrated non-L1 DNA to amplify DNA flanking the non-L1 DNA, which flanking DNA comprises a host cell DNA fragment, and, isolating the host cell DNA fragment so amplified.

The invention additionally includes a method of delivering a gene to a cell comprising transfecting the cell with an isolated DNAc molecule comprising a promoter P and an L1 cassette sequence comprising a core L1 retrotransposon element comprising non-L1 DNA and a promoter P' for expression of the non-L1 DNA, wherein the non-L1 DNA comprises a gene.

In one embodiment of this aspect of the invention, the non-L1 DNA encodes a protein capable of correcting a genetic defect in a cell and expression of the protein in the cell corrects the genetic defect. Further, in another embodiment, the cell is obtained from an animal prior to transfection and is returned to the animal following transfection.

In another aspect of the invention, there is provided a method of delivering a gene to a cell in an animal comprising administering to the animal an isolated DNAc molecule comprising a promoter P and an L1 cassette sequence comprising a core L1 retrotransposon element comprising non-L1 DNA and a promoter P' for expression of the non-L1 DNA, wherein the non-L1 DNA comprises a gene.

In one embodiment of this aspect of the invention, the non-L1 DNA encodes a protein capable of correcting a genetic defect in the animal and expression of the protein in the cell corrects the genetic defect in the animal. Further, in another embodiment, the protein is selected from the group consisting of cystic fibrosis transmembrane conductance regulator, β-globin, a blood clotting protein, an enzyme, a tumor suppressor protein and a cytokine.

Also included in the invention is a method of assessing the mutagenic potential of an animal comprising obtaining a population of cells from the animal, transfecting the cells with an isolated DNAc molecule comprising a promoter P and an L1 cassette sequence comprising a core L1 retrotransposon element comprising non-L1 DNA comprising a marker gene, and assessing the frequency of retrotransposition in the cells as a measure of the mutagenic potential of the animal, the frequency of retrotransposition being directly proportional to the mutagenic potential in the animal.

The invention also includes a method of identifying an anti-mutagenic compound comprising transfecting a population of cells, in the presence or absence of a test compound, with an isolated DNAc molecule comprising a promoter P and an L1 cassette sequence comprising a core L1 retrotransposon element comprising non-L1 DNA, and assessing the frequency of retrotransposition in the cells, wherein a lower frequency of retrotransposition in the cells in the presence of the test compound, compared with the frequency of retrotransposition in the absence of the test compound, is an indication that the test compound is an anti-mutagenic compound.

BRIEF DESCRIPTION OF THE DRAWINGS

FIG. 2A is a diagram depicting cloning of L1.2mneoI. L1.2mneoI cloned into pCEP4 to create pJM101. pCEP4 contains an origin of replication (Ori) and a selectable marker (Amp) for prokaryotic cells and an origin of replication and transacting factor (Ori/EBNA1) and a selectable marker (Hyg) for eukaryotic cells. The direction of transcription of each gene is denoted by arrows. The features of L1.2mneoI are described in the description of FIG. 1.

FIG. 2B, comprising FIGS. 2Bi, 2Bii, and 2Biii, is a trio of diagrams depicting mutant constructs of L1.2mneoI. pJM102 (FIG. 2Bi) lacks the 910 bp 5' UTR of L1.2; pJM103 (FIG. 2Bii) has a 3.8 kb deletion wherein most of the 5' UTR, all of ORF1 and the first 2.1 kb of ORF2 are deleted; pJM105 (FIG. 2Biii) contains a missense mutation (D702Y) in ORF2. Each of the mutants have the pCEP4 sequences as the vector portion.

FIG. 4A is an image of a Southern blot of G418$^R$ clones following retrotransposition with L1.2mneoI. Genomic DNA was isolated from four independent G418$^R$ clones (lanes A–D). Approximately 20 μg of each DNA was restricted with EcoRI and was subjected to Southern blot analysis using a 0.46 kb neo gene as a probe. The size of the molecular weight standards used is indicated on the figure.

FIG. 4B, comprising 4Bi, 4Bii, and 4Biii, is an image of a gel (FIG. 4Biii) depicting precise splicing of the intron present in the original retrotransposon construct and an image of the structure of the products. 500 ng of genomic DNA from clones A–D was used as individual templates in PCR reactions using the primers neo437S and neo1808AS. One fifth volume of the products was separated on a 1.0% agarose gel containing ethidium bromide. A 468 bp DNA fragment (FIG. 4Bii) diagnostic for the loss of the intron was detected in each clone (lanes 2, 3, 4 and 5). In addition, a small amount of a 1361 bp DNA fragment (FIG. 4Bi) diagnostic for the original vector was observed in lanes 2, 3 and 4. Lane 6 contains DNA from HeLa cells and lane 7 is a DNA negative control. Lane 1 contains a 1 kb molecular weight size ladder (Gibco/BRL).

FIG. 8, comprising

FIG. 11, comprising FIGS. 11A–11D, is a series of gels and a sequence depicting cleavage hotspots in pBS plasmid. In the gel depicted in FIG. 11A, L1 ENp double-strand break hotspot is shown. Linear pBS DNA products were electroeluted, digested with restriction enzymes, and run on agarose gels. The gel shown in FIG. 11B depicts the L1 ENp cleavage reaction. Lane 1, supercoiled DNA substrate; lanes 2–5, 13 ng, 26 ng, 65 ng and 130 ng of L1 ENp added to 3.2 μg DNA, respectively; 5% of these samples were run on the gel. In the gels depicted in FIGS. 11Ci, 11Cii, and 11Ciii, primer extension on uncleaved substrate and L1 ENp products was performed on the products shown in (B). A sequence ladder generated with the kinased primer JB1132 (FIG. 11Ci), JB1133 (FIG 11Cii), or T7 (FIG. 11Ciii) was included for each reaction. Primers JB1132 and JB1133 are specific for each strand flanking the cleavage hotspot region of pBS. In the sequence listed in FIG. 11D), cleavage hotspots in pBS are shown. Major cleavage sites are denoted by large vertical arrows; minor cleavage sites are denoted by smaller vertical arrows; horizontal arrows indicate inverted repeats heavy arrows, pBR322 minor; thin arrows, pBR322 sub-minor; Lilley, 1981, *Nucl. Acids Res.* 9:1271–1288). [SEQ ID NO:90]

FIG. 12, comprising FIGS. 12A (JB1132), 12B (JB1133), and 12C (T7) is an image of a gel depicting cleavage specificity of the enzyme, which cleavage does not require supercoiling. DNAs were treated with L1 ENp and used as templates for primer extension experiments as in FIG. 11. Lanes 1, supercoiled DNA, no L1 ENp; lanes 2, supercoiled DNA+20 ng L1 ENp; lanes 3, relaxed closed circular DNA, no L1 ENp; lanes 4, relaxed closed circular DNA+80 ng L1 ENp. GATC lanes indicate sequencing reactions primed with the indicated kinased oligonucleotide.

FIG. 14, comprising FIGS. 14A–14G, is a diagram of a series of sequences depicting the similarity of in vitro cleavage sites for L1 ENp and the predicated sites of priming of reverse transcription. In the diagram FIG. 14A depicts, [SEQ ID NO:92–94], a model based on the JH-25 sequence for concerted target DNA nicking and reverse transcription of the 3' poly A end of L1 RNA is shown. The specificity of L1 ENp for $(PY)_n \downarrow (Pu)_n$ generates a polypyrimidine 3' terminus that can in principle base pair to the 3' poly A of L1 RNA. Such complementarity might stabilize a reverse transcription priming complex (B–G). Comparison of L1 ENp cleavage sites determined in vitro (shown in B) [SEQ ID NO:95–106] to various in vivo inferred priming sites involved in L1 retrotransposition is also shown. Note that the nucleotide 3' to the cleavage site is always a purine, is usually an A, and is usually part of an oligopurine run (boxed residues). In many cases, there is a symmetrically placed oligopyrimidine tract 5' to the cleavage site or inferred priming site (underlined residues). For parts (FIGS. 14C–14G) letters in lower case represent the TSD. Note that the runs of As at the 5' end of many of the TSDs represent an area of microhomology with the 3' poly A tract of the L1 insertion. These are assumed to represent part of the TSD here. In FIGS. 14Bi, and 14Bii (in vitro L1 ENp cleavage sites), pBS targets are shown. The top strand (FIG. Bi) is arbitrarily defined as the strand cleaved first. Bottom strands are shown in FIG. 14Bii. In FIG. 14C, [SEQ ID NO:107–111], new mutations caused by L1 insertion are shown. These include three hemophilia A mutations (Kazazian et al., 1988, *Nature* 332:164–166; Woods-Samuels et al., 1989, *Genomics* 4:290–296) and a dystrophin mutation (Holmes et al., 1994, *Nature Genet.* 7:143–148), and a somatic insertion into the APC tumor suppressor gene associated with cancer (Miki et al., 1992, *Cancer Res.* 52:643–645). In FIG. 14D, [SEQ ID NO:112–114], new L1-neo transposition events that occur in HeLa cells and described herein are shown. In FIG. 14E, [SEQ ID NO:115–116], active transposon copies discovered as progenitor elements for the JH-27 insertion (L1.2) and the dystrophin insertion (LRE2) are shown. In FIG. 14F, [SEQ ID NO:117–121], other full length elements cloned intentionally in searches to find active elements L1.1–L1.4 (Dombroski et al., 1991, *Science* 254:1805–1808; Dombrowski et al., 1993, *Proc. Natl. Acad. Sci. U.S.A.* 90:6513–6517), CGL1.1 (Hohjoh et al., 1990, *Nucl. Acids Res.* 18:4099–4104) or discovered by searching for element copies in GenBank (Z73497) are shown. In FIG. 14G, [SEQ ID NO:122–129], GenBank was searched using BLASTN with the 3' UTR sequence of L1.2 and the top 34 hits were studied. Approximately half of the 5' truncated elements had a precise TSD. These are all listed on this Figure, identified by the appropriate GenBank accession number.

FIG. 15, comprising FIGS. 15A and 15B is a diagram and a table showing that the L1 En domain is required for transposition in HeLa cells. In FIG. 15A, a diagram of the L1.2mneoI retrotransposition assay is shown. A neo marker gene with a "backward" intron (mneoI) is inserted upstream of L1 3' UTR such that neo and L1 are convergently transcribed. L1 transcription from the CMV promoter leads to the splicing of the intron and reconstruction of the neo coding region. Reverse transcription and integration leads to expression of neo from its SV40 promoter, pCMV, cytomegalovirus early promoter; S.D., splicing donor; S.A., splicing acceptor; wavy line, RNA; V, intron sequence. In FIG. 15B, L1 retrotransposition frequencies are tabulated. D703Y is the RT active site mutant; the other mutants are EN domain mutants.

DETAILED DESCRIPTION OF THE INVENTION

The invention is based on the discovery that novel human L1 elements are capable of retrotransposition in human cells as well as cells of other animal species. Such L1 elements have a variety of uses in human and animal genetics including, but not limited to, uses in diagnosis and treatment of genetic disorders and in cancer. The L1 elements of the invention are also useful for the treatment of various phenotypic effects of various diseases. For example, L1 elements may be used for transfer of DNA encoding anti-tumorigenic gene products into cancer cells. Other uses of the L1 elements of the invention will become apparent to the skilled artisan upon a reading of the present specification.

Figures 1A, 1B:
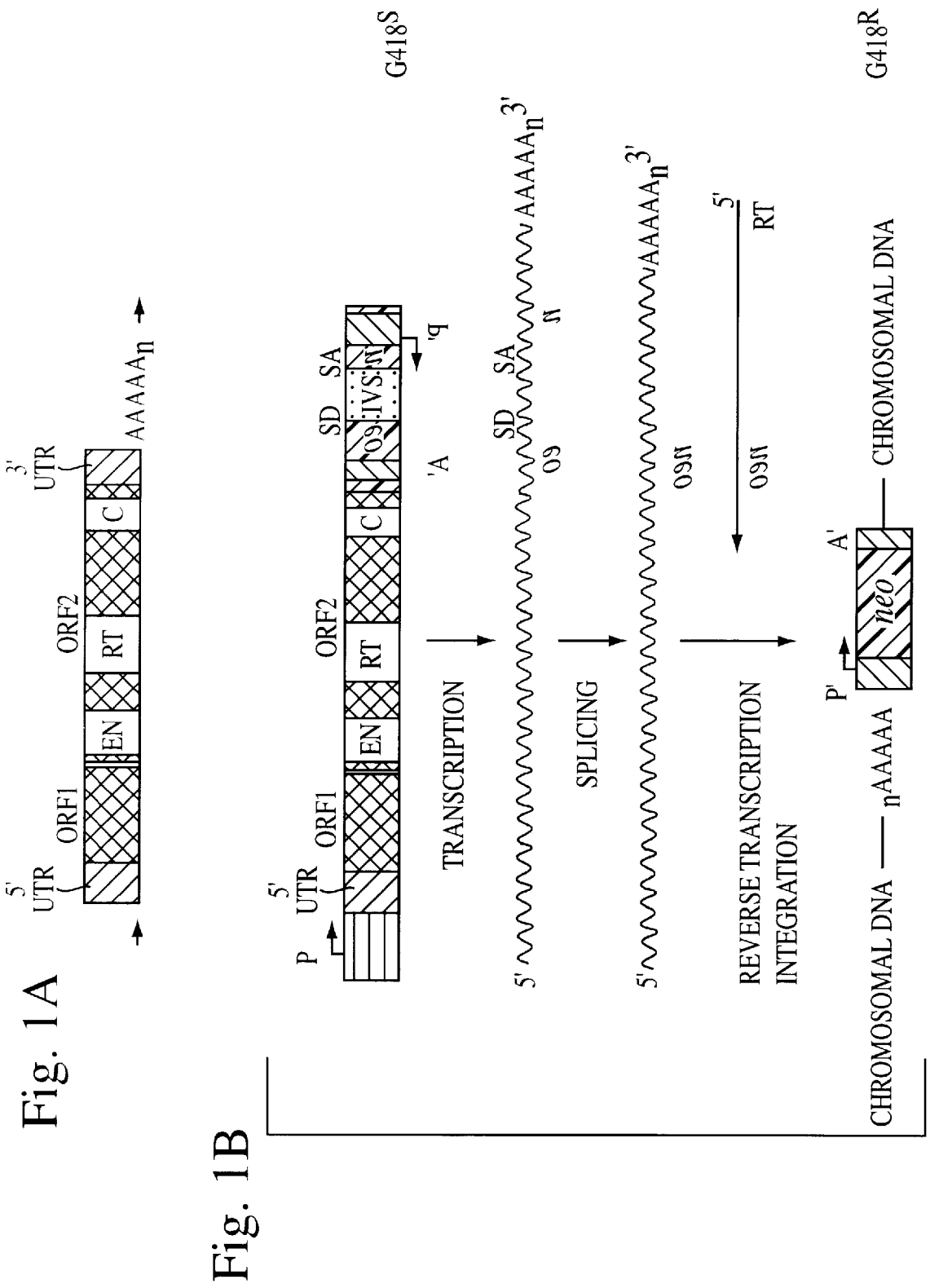
FIG. 1A is a diagram depicting the organization of a 6.0 kb human L1 element. ORF1 and ORF2 are indicated by cross-hatched rectangles; the 5' and 3' untranslated regions are indicated by downwardly-hatched rectangles and the untranslated region between ORF1 and ORF2 is indicated by a non-filled stripe. The approximate position of the endonuclease (EN), reverse transcriptase (RT), cysteine-rich C. motif and poly A tail (AAAAA)n are indicated. Arrows indicate the target site duplications which flank the element.
FIG. 1B is a diagram of an overview of a retrotransposition assay. The element L1.2 was tagged with an indicator gene (mneoI) containing an antisense copy of the neo gene disrupted by intron 2 of the γ-globin gene in the sense orientation. The splice donor (SD) and splice acceptor (SA) sites of the intron are indicated on the figure. The neo gene is also flanked by a heterologous promoter (P') and a polyadenylation signal (A') denoted by the upwardly-hatched regions. Transcripts originating from the promoter driving L1.2mneoI expression (P) can splice the intron, but continue to contain an antisense copy of the neo gene. G418-resistant (G418$^R$) colonies should arise only when this transcript is reverse transcribed, integrated into chromosomal DNA, and expressed from its own promoter, P'.

In general, a human L1 element comprises a 5' UTR with an internal promoter, two non-overlapping reading frames (ORF1 and ORF2), a 200 bp 3' UTR and a 3' poly A tail (FIG. 1A). As described herein, the L1 retrotransposon of the present invention also comprises an endonuclease domain at the L1 ORF2 N-terminus. The finding that L1 encodes an endonuclease demonstrates that the element is capable of autonomous retrotransposition. In addition, the data provided herein establish that L1 is a modular protein that contains non-overlapping functional domains which mediate its reverse transcription and integration. As such, it is now possible to either alter the sequence specificity of the L1 endonuclease itself or replace the L1 endonuclease with another site-specific endonuclease.

It has been found, according to the present invention, that two L1 elements (L1.2 and LRE2) are capable of actively retrotransposing in cultured animal cells. These elements were isolated following the procedures described in Dombroski et al. (1991, Science 254:1805–1808) and Holmes et al. (1994, Nature Genetics 7:143–148) and are the progenitors of disease-producing insertions in humans. Other active L1 elements are also described herein. As will be described in detail herein, when either of these elements is stably expressed from an episome in HeLa cells, both retrotranspose into a variety of chromosomal locations at high frequency. The retrotransposed products resemble endogenous L1 insertions since they are variably truncated, end in poly A tracts and are flanked by target site duplications or short deletions. Point mutations in conserved domains of the L1.2 encoded proteins reduce retrotransposition by 100–1000 fold. Unexpectedly, the L1.2 retrotransposon also retrotransposes in a mouse cell line, establishing that such elements are capable of crossing species barriers and providing evidence that these retrotransposons may be used for random insertional mutagenesis.

According to the present invention, the L1 retrotransposon may be manipulated using recombinant DNA technology to comprise and/or be contiguous with, other DNA elements which render the retrotransposon suitable for insertion of substantial lengths (up to 1 kb, or greater than 1 kb) of heterologous or homologous DNA into the genome of a cell. The L1 retrotransposon of the present invention may also be manipulated using the same type of technology such that insertion of the DNA into the genome of a cell is site-directed; in other words, the site into which such DNA is inserted is known. Alternatively, the L1 retrotransposon may be manipulated such that the insertion site of the DNA is random. The retrotransposon may also be manipulated to effect insertion of a desired DNA sequence into regions of DNA which are normally transcriptionally silent, wherein the DNA sequence is expressed in a manner such that it does not disrupt the normal expression of genes in the cell.

The key features which control insertion of heterologous or homologous DNA reside in the components of the L1 element itself and in the components of the episomal ("vector") sequences which flank the element. Such key features are now described in detail herein.

Essentially, to effect random insertion of a DNA sequence into a cell genome, an isolated DNA molecule is added to the cell, which DNA comprises an L1 element which is flanked by other elements, or has inserted into it other elements, each of which elements are useful for the generation and propagation of the L1 element in both prokaryotic and eukaryotic cells. The DNA molecule is generally added to the cell in the form of a plasmid DNA, which plasmid may be maintained in the cell into which it is placed as an episome. However, while an episomal DNA molecule is exemplified in the discussion which follows, the invention should not be construed to be limited to L1 elements which are contained within an episome. Rather, the invention should be construed to include any and all types of DNA or RNA molecules or virus particles containing nucleic acids which may be added to a cell to effect retrotransposition in that cell. Thus, in addition to episomes, the invention should be construed to include viral vectors, simple plasmids and cosmids. In addition, the invention should be construed to include naked DNA and DNA in the form of concatamers as well as placing L1 element DNA on mammalian artificial chromosomes.

For the purposes of clarity and to distinguish it from other DNAs which are discussed herein, the DNA molecule of the invention which is just described is hereinafter referred to as "DNAc" which denotes a complete DNA molecule comprising an L1 element which is flanked by, or has inserted therein, other elements which are useful for the generation and propagation of the L1 element in a cell.

Each of the required elements in such a DNAc molecule are now described using an episome as a model DNAc molecule for transfection into cells to effect retrotransposition of an L1 element in the cells, bearing in mind that the invention is not limited to episomes.

Referring to FIG. 1, the DNAc molecule comprising an L1 element useful for random insertion of a heterologous or homologous DNA sequence into a cell genome comprises a promoter sequence (P) positioned just upstream of the 5' UTR region, which promoter can be either an RNA polymerase II or an RNA polymerase III promoter. Examples of RNA polymerase II promoters which are useful include, but are not limited to, housekeeping promoters such as actin, PGK, DNA polII or a ubiquitin promoter; tissue specific promoters, for example, the albumin, globin, ovalbumin promoter sequences, skin specific promoters such as K12 or K14, inducible promoters, for example, steroid inducible promoters, tetracycline inducible promoters and the like, and viral promoters such as the SV40 early promoter, the Rous sarcoma virus (RSV) promoter and the cytomegalovirus immediate early promoter (CMV) as well as other retroviral LTRs. Examples of RNA polymerase III promoters which are useful include, but are not limited to, an L1 element promoter, tRNA promoters and the 5S RNA promoter. When tissue specific expression is desired, expression of the L1 element will be effected by a tissue specific RNA pol II promoter sequence. When general cellular expression of the L1 element is desired, then a constitutive RNA pol II promoter will be used, or even an RNA pol III promoter will be used. The type of promoter which provides optimal expression of the desired DNA will depend on the desired result and will be apparent to the artisan practicing the invention.

The isolated DNA molecule comprising an L1 element useful for random insertion of a heterologous or homologous DNA sequence into a cell genome also comprises an L1 cassette comprising a core L1 retrotransposon element comprising the following elements: A 5' UTR, ORF1, ORF2 (including EN and RT domains), a 3' UTR and a poly A signal. Heterologous DNA, and/or marker DNA may be positioned within the 3' UTR sequence or between the 3' UTR and the poly A signal. In addition, a second promoter sequence (P') is located within the vicinity of the 3' UTR, which promoter sequence drives expression of the heterologous/marker DNA.

Examples of core L1 retrotransposon elements include, but are not limited to, L1.2, LRE2, L1.3, L1.4, L1.19, L1.20 and L1.39. Also included are mouse L1 elements which include, but are not limited to, L1 spa and L1 orleans reeler. These latter two elements are responsible for the spastic mouse and the reeler mouse, respectively.

The P' promoter may be an RNA pol II or an RNA pol III promoter. Examples of P' RNA pol II promoters include, but are not limited to, housekeeping promoters, such as an actin promoter, DNA pol II promoter, PGK or a ubiquitin promoter, tissue specific promoters, for example, the albumin, globin, ovalbumin promoter sequences, skin specific promoters such as K12 or K14, inducible promoters, for example, steroid inducible promoters, tetracycline inducible promoters and the like, and viral promoters such as the SV40 early promoter, the Rous sarcoma virus (RSV) promoter and the cytomegalovirus immediate early promoter (CMV), ppol III promoter, PGK and retroviral LTR. Examples of RNA polymerase III promoters which are useful include, but are not limited to, an L1 element promoter, tRNA promoters and the 5S RNA promoter. When tissue specific expression is desired, expression of the L1 element will be effected by a tissue specific RNA pol II promoter sequence. When general cellular expression of the L1 element is desired, then a constitutive RNA pol II promoter will be used, or even an RNA pol III promoter will be used. The type of promoter which provides optimal expression of the desired DNA will depend on the desired result and will be apparent to the artisan practicing the invention.

Also included in an L1 retrotransposon cassette useful for random insertion of DNA is the heterologous or homologous DNA (non-L1 DNA) which is to be inserted into the cell genome. This DNA is positioned within the 3' UTR sequences, or between the 3' UTR and the poly A signal, and is oriented such that expression of the DNA is under the control of promoter P'. The type of DNA to be inserted includes, but is not limited to, DNA which functions as a marker for identification of the site of insertion, for example, the neomycin (neo) resistance gene or other drug resistance genes (e.g., zeo, hygro, gpt), the green fluorescence protein (GFP) gene, lacZ, the herpes simplex virus (HSV) thymidine kinase gene, and even cell surface receptor genes such as, but not limited to, T cell receptor genes.

Also included is DNA (usually cDNA or minigenes) which is useful for correction of a genetic defect in the cell into which the insertion is made. DNAs which can be used to effect correction of such genetic defects may be derived from, or comprise wild type forms of genes which are mutated in the cell, thereby giving rise to the genetic defect. Such DNAs include, any known or unknown DNA which can be used to correct a genetic defect in cells having such a defect. Examples of such DNA include cDNAs encoding the cystic fibrosis transmembrane conductance regulator (CFTR), cDNA encoding β-globin, cDNA encoding blood clotting proteins, cDNA encoding enzymes such as, but not limited to adenosine deaminase, hypoxanthine guanine phosphoribosyl transferase (HGPRT) and the like, cDNAs which play a role in cancer, such as, but not limited to, tumor suppressor genes, p53, p21, p16, retinoblastoma, Wilm's tumor, and the like, and also cytokines, interleukins and genes which encode therapeutic peptides, and the like.

Genetic defects which may be corrected using the retrotransposition of the invention include, but are not limited to, cystic fibrosis, mutations in the dystrophin gene, genetic defects associated with blood clotting and any other either known or as yet unknown genetic defect (e.g., lysosomal storage diseases and other metabolic diseases).

Further included in the invention are DNAs which are useful for the generation of mutations in a cell, which mutations are useful for assessing the frequency with which selected cells undergo insertional mutagenesis for the generation of transgenic animals and the like. Engineered L1 elements can also be used as transposon mutagens. Sequences can be introduced into the L1 that increases its mutagenic potential or facilitates the cloning of the interrupted gene. DNA sequences useful for this application of the invention include marker DNAs, such as GFP, that are specifically engineered to integrate into genomic DNA at sites which are near to the endogenous genes of the host organism. Other potentially useful DNAs for delivery are regulatory DNA elements, such as promoter sequences, enhancer sequences, retroviral LTR elements and repressors and silencers. In addition, genes which are developmentally regulated are useful in the invention.

The length of the DNA which is to be inserted into the genome of a cell may vary from a few base pairs (for example 10 or less base pairs) to about 10,000 base pairs of DNA. Typically, the length of the DNA to be inserted into a cell genome will vary from about 50 base pairs to about 10,000 base pairs; more typically, the length will vary from about 500 to about 5000 base pairs; even more typically, the length will vary from about 750 to about 2,500 base pairs. Preferably, the length of the DNA to be inserted into the genome of a cell will be about 1000 base pairs.

According to the data presented in Example 1, about 1000 bp is the preferred size of the DNA to be inserted into cell DNA if L1.2 is used as the delivery vehicle (Experimental Details section) because of the truncation process which occurs during retrotransposition. However, it may be possible to control truncation of DNA during retrotransposition by using reverse transcriptase domains that are altered to facilitate increased processivity of the enzyme, thereby facilitating insertion of longer lengths of DNA into the cell genome. An example of such an RT domain is found in a naturally occurring L1 element, L1.3. Using L1.3 it is possible to insert DNAs of at least 6000 bp in size. In addition, it will be appreciated that it may be possible to restrict the length of the DNA inserted into the host genome, by positioning hairpin structures in the DNA to be inserted at the 3' site where the DNA is to be restricted. Insertion of ribozyme sequences into a length of heterologous DNA may also be used to effect cleavage of the RNA and hence, restriction of the DNA length. Finally, the sequences to be inserted may be placed under the control of tissue-specific elements, such that the entire inserted DNA is only functional in those cells in which the tissue-specific element is active.

The engineered L1s can be introduced into cells using a variety of vectors. One such vector sequence is that used in Moran et al. (1996, Cell 87:917–927) which is described in the Experimental Details section. However, other vector sequences can be used. Thus, the vector sequence of the DNA molecule may comprise DNA sequences derived from a virus, such as, but not limited to, Epstein Barr virus (EBV) comprising oriP and EBNA1 or a polyoma-based virus comprising the polyomavirus origin of DNA replication and a polyomavirus enhancer sequence. Other viral vectors useful in the invention include adeno-associated virus, lentivirus, parvovirus, herpes simplex virus, retroviruses, poxviruses, and the like. These sequences comprise a eukaryotic origin of DNA replication to facilitate replication of the DNA molecule in a eukaryotic cell. Note, however, that certain delivery vehicles, such as adeno-associated virus, may be replication deficient, but are still useful because they provide efficient delivery vehicles for introduction of the DNA into the desired target cell. It is not necessary that the vector sequences be limited to naturally occurring eukaryotic viral elements. Mammalian artificial chromosomes are also contemplated in the invention.

Also included in the delivery vector is a prokaryotic origin of DNA replication may also be added to the construct along with an antibiotic resistance gene. Such sequences facilitate replication of the DNAc molecule of the invention in prokaryotic cells, thereby facilitating the generation of large quantities of DNA for insertion to the desired eukaryotic cell genome. A prokaryotic origin of DNA replication is also added along with an antibiotic resistance gene to facilitate growth of the construct in prokaryotic cells. Examples of prokaryotic origins of DNA replication suitable for use in the DNAc molecule of the invention include, but are not limited to, the ColEI and pA15 origins of DNA replication. Note that these origins of replication (ori's) are on the vector and not on the DNA to be inserted. The DNA to be inserted can also be accompanied by an ori and this modification is outlined below.

The nature of the eukaryotic DNA replication origin sequences to be used will depend upon the application contemplated for the retrotransposon. For example, it may be necessary in some instances to include an origin of DNA replication which facilitates replication of the DNA molecule in a low copy number. Alternatively, a high copy number of the DNA molecule in cells may be required in which case an origin of DNA replication capable of yielding a high copy number of DNA molecules is preferable. Similarly, it may be necessary to direct replication of the DNA molecule to the nucleus of the cell, and it may be necessary that such replication be episomal in nature. Origins of replication which are useful for the generation of either low copy number or high copy number, include, as examples, oriP driven by the EBNA1 protein or a papillomavirus origin of DNA replication which generate approximately 10–20 copies of DNA per cell (high copy number) and mammalian artificial chromosomes which generate 1–2 copies per cell (low copy number).

Further included in the vector sequence of the DNAc molecule are one or more selectable marker genes for detection of either prokaryotic or eukaryotic cells into which the DNAc molecule has been successfully transfected. Examples of suitable prokaryotic marker genes include, but are not limited to, the ampicillin resistance gene, the kanamycin resistance gene, the gene encoding resistance to chloramphenicol, the lacZ gene and the like. Examples of suitable eukaryotic marker genes include, but are not limited to, the hygromycin resistance gene, the green fluorescent protein (GFP) gene, the neomycin resistance gene, the zeomycin gene, modified cell surface receptors, the extracellular portion of the IgG receptor, composite markers such as β-geo (a lac/neo fusion) and the like.

Different features of the DNAc molecule may be altered depending on the desired application. For example, to effect site-specific insertion, as opposed to random insertion, of DNA into a host cell genome, a specific DNA binding domain may be positioned between the 5' end of ORF2 and the endonuclease domain. The specific domain may include, but is not limited to, a p53 binding domain, a zinc finger binding domain, type II endonuclease binding domain, a homeobox binding domain, and the like. The use of these domains will facilitate specific insertion of L1 retrotransposons next to genes whose expression is governed by these binding domains. Such a strategy is therefore useful for the isolation of new genes whose expression is governed by any one of the binding domains used.

To isolate specific genes from a host chromosome, the marker gene in the 3' UTR region or between the 3' UTR and SV40 polyA signal is altered as follows. The DNA to be inserted may be accompanied by a prokaryotic origin of replication and the promoter for the marker gene can be replaced by a promoter that functions in both eukaryotic and procaryotic cells. Therefore, one can easily identify and clone host genomic DNA flanking mutagenic insertions. Cloned versions of these DNAs can then be propagated in bacteria, essentially effecting a one-step cloning approach. For example, genomic DNA isolated from cultured animal cells containing retrotransposed copies of the neo gene can be restricted with an enzyme that does not cut within the L1 element or the indicator gene. The DNA is ligated under dilute conditions to promote unimolecular self-closing and the products are used to transform E. coli. The kanamycin resistant E. coli clones obtained contain the retrotransposed L1/neo insertion as well as genomic sequences flanking the insertion. Similarly, the DNA to be inserted can be accompanied by other eukaryotic ori's (e.g. yeast 2 micron or ARS/CEN) to facilitate cloning of the DNA flanking the newly generated L1 insertion in other eukaryotic model organisms.

The marker gene in the 3' UTR may also be modified such that genes of the host are "tagged." The promoter and the initiation codon of the marker gene is eliminated and an intron acceptor splice site is added in place thereof such that the marker gene is now only expressed as a fusion protein with an endogenous host cell fusion protein. This type of construct is termed a "gene trap" and is useful for making insertional mutations which are specific for expressed genes. Gene trap vectors can also be modified using antisense technology to eliminate expression of the undisrupted wild type gene, thereby effecting a complete knockout of the gene. Three different constructs, each providing a different reading frame of the marker gene, can be positioned downstream of the acceptor site in the sense orientation to optimize detection of insertions. In a similar strategy, a promoterless indicator gene containing an initiation codon can be cloned into the 3' end of the L1 element. G418-resistant colonies will be obtained when the L1 retrotransposes near an active promoter. This construct is termed a "promoter trap" construct. Similarly, a minimal promoter can be used to create an "enhancer trap" construct.

To direct insertion of DNA into inactive regions of host cell DNA, it may be possible to alter the ORF2 protein such that it cleaves host cell DNA at innocuous sequences, for example, in ribosomal RNA gene sequences. Alternatively, it may be possible to replace the endonuclease domain of ORF2 with the domain of another enzyme which specifically cleaves DNA at innocuous sequences. Such enzymes include, but are not limited to, the rep gene of adeno-associated virus and certain group I intron-encoded, site-specific endonucleases, e.g,. The universal code equivalent of the yeast mitochondrial sce1 gene.

While any combination of the elements described herein may be suitable in the DNAc molecule of the invention, an example of such a DNAc molecule comprises a heterologous promoter P comprising the CMV immediate early promoter, an L1.2- or an LRE2-based cassette sequence having about 1 kb of heterologous DNA positioned therein comprising the neo gene encoding G418 resistance, and a P' promoter for expression of the neo gene, an EBV based vector comprising an EBV origin of DNA replication (oriP) and EBNA, a prokaryotic origin of DNA replication comprising colEI DNA replication origin, a eukaryotic selectable marker comprising the hygromycin resistance gene and a prokaryotic selectable marker comprising the ampicillin resistance gene.

In the DNA molecule exemplified herein, a neo gene is inserted into an L1.2-containing vector as an indicator of retrotransposition events (see FIG. 1B). Expression of the neo gene product in mammalian cells confers resistance to the normally toxic drug, G418 (neomycin sulfate). In these constructs, the neo gene is interrupted by a small artificial intron from the γ-globin gene (IVS-2) which is placed in the opposite transcriptional orientation (positioned in the antisense orientation) to the neo gene but in the same orientation as the transposable element. In this arrangement, G418-resistant ($G418^R$ or $neo^R$) cells will be recovered when the marked copy of L1.2 retrotransposes and the resulting neo gene is expressed from its own promoter, P' (see FIG. 1B for a schematic representation). The neo sequence cannot be expressed from the L1 element mRNA, even after splicing, because it is in the antisense orientation. This provides for selection of the relatively rare retrotransposition event.

Using the above-described constructs, a reporter system that selects for L1 retrotransposition into actively transcribed genes can be developed. Essentially, the development of this type of vector greatly facilitates the development of an efficient transposon mutagenesis system. This vector system is referred to herein as a "gene trap", or "promoter trap" or "enhancer trap" system.

To develop this system, the P' driving neo gene expression is removed and a splice acceptor signal is inserted at the start codon of the neo gene; the bacterial promoter and origin of replication is retained downstream of the indicator gene. When the L1 element retrotransposes into a desired region of the genome, the neo gene is spliced into mRNA. If the splicing event places the neo gene in-frame with the preceding exons, the neo mRNA is translated and $G418^R$ colonies will result. Three different constructs may be designed such that all three reading frames of marker DNA are read thereby ensuring expression of protein from any spliced mRNA. The presence of the bacterial promoter and origin of replication downstream of the indicator gene should not interfere with splicing, but will allow for the simple isolation of the retrotransposed genomic L1/neo insertions using methods similar to those described herein. This construct will yield valuable information about how often L1 retrotransposes into active gene, a fact which is useful for gene delivery experiments.

Other retrotransposition markers that allow for a more rapid evaluation of retrotransposition events and expression studies can also be developed. For example, in one embodiment lacZ interrupted by an antisense intron can be used. In conjunction with a "promoter trap" strategy as described, the use of an L1/lacZ marker construct in transgenic mice will yield information concerning where and when in development the retrotransposed L1 construct is expressed. Such trap assay reporter constructs are routinely used during P element mutagenesis in Drosophila (Cooley et al., 1988, Science 239:1121–1128). In another embodiment, GFP from jellyfish is interrupted with an antisense intron. GFP offers similar advantages to a lacZ reporter system, but also allows one to follow the expression of the marker gene in live cells.

As will be described in detail herein, the DNAc molecule of the present invention may be used for delivery of human cDNAs or human minigenes into cell lines. A strategy to carry out high frequency, insertional mutagenesis in mice is now described. This strategy is also applicable for high frequency, insertional mutagenesis in human cells.

An antisense GFP construct is generated which replaces the neo$^R$ marker gene in the 3' UTR of L1. As before, the initiation codon ATG of the GFP gene is replaced and a splice acceptor sequence is placed at the 5' end of the GFP gene. GFP expression will only occur when the gene product is expressed as an in-frame fusion protein. The N-terminus of this fusion protein is derived from the host gene into which the DNA inserted. A similar strategy can be used using lacZ or composite indicator genes such as (lacZ/neo or GFP/neo). Further, it is possible to make three independent constructs to insure that insertions can be identified in the three relevant reading frames. The L1 construct is driven by either a ubiquitously-expressed strong promoter such as CMV, for germ line expression, or by a tissue-specific or inducible promoter, such as an immunoglobin promoter/enhancer or the tet inducible promoter, for tissue-specific expression.

In the case of germ line expression, transgenic mice are generated by microinjection of mouse oocytes with different L1 constructs containing the GFP gene in the "gene trap" configuration in all three reading frames, driven by the CMV promoter, into the germ cells of the mice. Sperm are obtained from the male progeny, and GFP-positive sperm are sorted by fluorescence-activated cell sorting (FACS). Sperm having a high number of GFP insertions are collected and are injected into mouse eggs to fertilize them. Fertilized eggs are then implanted into pseudopregnant female mice. This approach will lead to the generation of high frequency mutation during embryonic development and post-natal life of the resulting conceptuses. Alternatively, transposon mutagenesis can be carried out in embryonic stem (ES) cells of mouse origin.

As discussed herein, promoter traps or enhancer traps in somatic cells may be used to provide mutations in a variety of genes, including, but not limited to, genes which provide susceptibility or resistance to tumor development in various cell types.

Since L1 is native to human cells, when the constructs are placed into human cells, they should not be rejected by the immune system as foreign. In addition, the mechanism of L1 retrointegration ensures that only one copy of the gene is integrated at any specific chromosomal location. Accordingly, there is a copy number control built into the system. In contrast, gene transfer procedures using ordinary plasmids offer little or no control regarding copy number and often result in complex arrays of DNA molecules tandemly integrated into the same genomic location.

In one embodiment, the neo reporter construct is replaced with a cDNA containing a human gene of interest with an antisense intron. This procedure is most useful when delivery of the gene can be readily selected for or screened by simple biochemical assays. A cDNA or minigene containing hypoxanthine guanine phosphoribosyl transferase gene (hgprt) is one example of a gene which can be selected for in human cells in culture. The hgprt gene containing an antisense intron can be placed in the 3' UTR of the L1 element. The most practical current approach to gene therapy is an ex vivo approach whereby cells are obtained from the individual, the gene of interest is inserted into these cells, and the cells are then reimplanted in the individual. It is likely that first attempts at gene therapy using the L1 constructs described herein would use this approach.

For genes of interest which do not impart a selective advantage on delivery, an L1 construct can be routinely engineered to deliver both the gene of interest and a selectable marker. To accomplish this, an inverse bicistronic reporter construct is inserted into the 3' UTR of L1. The first reading frame of the construct codes for the gene of interest. The second reading frame contains a standard neo reporter construct containing an antisense intron, but the neo gene lacks a promoter. An internal ribosome entry signal (IRES) from picornavirus is inserted between the two genes. IRES sequences allow for the translation of bicistronic messages in mammalian cells. The L1 construct containing the bicistronic construct is introduced into cells. G418$^R$ colonies containing the retrointegrated copies of the construct are then isolated following the procedures described herein. Cells so isolated will contain a copy of the gene of interest as well as a copy of the neo gene.

By "retrotransposition" as used herein, is meant the process of integration of a sequence into a genome, expression of that sequence in the genome, reverse transcription of the integrated sequence to generate an extrachromosomal copy of the sequence and reintegration of the sequence into the genome.

An "L1 cassette sequence" as used herein, refers to a sequence of DNA comprising an L1 element comprising a 5' UTR, ORF1 and ORF2, a 3' UTR and a poly A signal, wherein the 3' UTR has DNA positioned either therein or positioned between the 3' UTR and the poly A signal, which DNA is to be inserted into the genome of a cell.

A "vector sequence" as used herein, refers to a sequence of DNA comprising at least one origin of DNA replication and at least one selectable marker gene.

By "selectable marker gene" as used herein is meant a gene or other expression cassette which encodes a protein which facilitates identification of cells into which the selectable marker gene is inserted.

By "gene" as used herein, is meant an actual gene including both the exons and introns of the gene. By "minigene" as used herein, is meant a portion of a gene including all the exons but only one or a small number of introns or a small artificial intron. By "cDNA" as used herein, is meant a portion of a gene including only the exons of the gene.

By "heterologous DNA" as used herein, is meant DNA which is not naturally found in the cell into which it is inserted. For example, when mouse or bacterial DNA is inserted into the genome of a human cell, such DNA is referred to herein as "heterologous DNA." In contrast, the term "homologous DNA" as used herein, denotes DNA which is found naturally in the cell into which it is inserted. For example, the insertion of mouse DNA into the genome of a mouse cell constitutes insertion of "homologous DNA" into that cell. In the latter case, it is not necessary that the homologous DNA be inserted into a site in the cell genome in which it is naturally found; rather, homologous DNA may be inserted at sites other than where it is naturally found, thereby creating a genetic alteration (a mutation) in the inserted site.

By "non-L1 DNA" as used herein, is meant DNA which does not naturally occur in an L1 element.

It will be appreciated that the invention should not be construed to be limited in any way to the precise DNA sequences which are disclosed herein. Homologous DNA sequences having substantially the same function as the disclosed DNA sequences are also considered to be included in the invention.

As used herein, the term "homology" refers to the subunit sequence identity or similarity between two polymeric molecules e.g., between two nucleic acid molecules, e.g., between two DNA molecules, or two polypeptide molecules. When a subunit position in both of the two molecules is occupied by the same monomeric subunit, e.g., if a position in each of two polypeptide molecules is occupied by phenylalanine, then they are identical at that position. The homology between two sequences, most clearly defined as the % identity, is a direct function of the number of identical positions, e.g., if half (e.g., 5 positions in a polymer 10 subunits in length) of the positions in two polypeptide sequences are identical then the two sequences are 50% identical; if 70% of the positions, e.g., 7 out of 10, are matched or homologous, the two sequences share 70% identity. By way of example, the polypeptide sequences ACDEFG [SEQ ID NO:130] and ACDHIK share 50% identity and [SEQ ID NO:131] the nucleotide sequences CAATCG and CAAGAC share 50% identity.

An "isolated DNA," as used herein, refers to a DNA sequence which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid (e.g., RNA, DNA or protein) in its natural state.

"Complementary," as used herein, refers to the subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

"Positioned in an antisense orientation with respect to the direction of transcription of the DNA" as used herein, means that the transcription product of the DNA, the resulting mRNA, does not encode the polypeptide product specified by the "sense" strand of DNA. Rather, the mRNA comprises a sequence which is complementary to an mRNA which encodes the protein product.

As discussed herein, the invention provides DNA encoding a protein product which may be used in gene therapy to correct a genetic defect in a cell. It should be understood that such a protein may comprise native polypeptide sequences, or may comprise modifications which render the protein in general more suitable as a gene therapy agent and more stable in a cell.

As used herein, the term "isolated preparation of a polypeptide" describes a polypeptide which has been separated from components which naturally accompany it. Typically, a polypeptide is isolated when at least 10%, more preferably at least 20%, more preferably at least 50%, more preferably at least 60%, even more preferably at least 75%, more preferably at least 90%, and most preferably at least 99% of the total material (by volume, by wet or dry weight, or by mole per cent or mole fraction) of a sample is the polypeptide of interest. The degree of isolation of the polypeptide can be measured by any appropriate method, e.g., by column chromatography, polyacrylamide gel electrophoresis, or by HPLC analysis. For example, a polypeptide is isolated when it is essentially free of naturally associated components or when it is separated from the native compounds which accompany it in its natural state.

The present invention also provides for analogs of proteins or peptides encoded by a DNA sequence to be inserted into the genome of a cell. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups, but are not limited to these groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine. In the latter instance, this is most applicable if reconstituted nucleic acid/protein particles are used for delivery. It is essentially and in vitro modification followed by an in vivo delivery.

Also included are polypeptides which have been modified using ordinary molecular biological techniques so as to improve their resistance to proteolytic degradation or to optimize solubility properties or to render them more suitable as therapeutic agents. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In particular, it may be desirable to be able to insert the desired DNA into specific sites in a cell genome. Such sites include, but are not limited to, the DNA pol II gene or the loxP sites of defined knockout mice. The entire L1 can be flanked with loxP sites and integration of L1 can be effected into loxP sites engineered into known locations in the mouse genome through use of the cre recombinase. This will facilitate site-specific integration of the human L1 in mouse cells and will be useful for transposon mutagenesis experiments.

To effect retrotransposition in a cell and therefore insertion of a desired DNA into the genome of a cell, the isolated DNAc molecule of the invention comprising an L1 cassette, including the desired DNA, and a vector sequence is added to a population of cells in a composition suitable to effect uptake by the cells of the DNA. For example, for transfection of cells in vitro when the DNAc molecule is in plasmid form, the DNAc molecule may be added to the cells in any number of formulations, including, but not limited to, a calcium phosphate transfection mixture, a liposome transfection formulation, and the like. Such types of transfection procedures are well known in the art and are described, for example, in Sambrook et al. (1989, *Molecular Cloning: A Laboratory Manual,* Cold Spring Harbor, N.Y.). DNAc may also be added to cells in the form of a virus which has been manipulated using recombinant DNA technology to accommodate the DNAc molecule and which also is suitable for delivery of the DNAc molecule to the desired cells. Suitable viral vectors are described elsewhere herein.

Retrotransposition may be targeted to specific types of cells which are either meiotic or mitotic in nature. With respect to meiotic cells, it is contemplated that many genetic defects may be corrected by effecting insertion of a desired homologous or heterologous DNA sequence into an egg or sperm cell by retrotransposition, thereby correcting the genetic defect in that cell. This application of the invention has particular use in in vitro fertilization technology, wherein sperm or eggs obtained from an individual animal having a known genetic defect may have inserted therein a DNA capable of correcting the defect. An egg or sperm whose defect is so corrected may then be used to generate an embryo and subsequently an animal which does not contain the defect. This application would have particular use in the mouse, but is specifically not contemplated for human experimentation. For human application, somatic gene therapy is contemplated, but germ line therapy is not appropriate for ethical reasons.

With respect to mitotic cells, it is contemplated that many genetic defects in animals may be corrected by insertion of the appropriate DNA sequence into cells exhibiting a phenotype characteristic of the genetic defect. Specifically, an ex vivo approach, as described above, is contemplated. For example, gene therapy has been used in humans to provide a wild type copy of the gene encoding the cystic fibrosis transmembrane regulator (CFTR) to cells having a mutated CFTR gene (Wilson, 1996, *Molecular Medicine* 334:1185–1187).

The invention is useful for the correction of genetic defects in animals, preferably mammals and even more preferably, humans. To correct a genetic defect in an animal, a method of gene delivery is included in the invention which is based upon delivery of a desired gene, or a biologically active fragment thereof, by retrotransposition, to the cells of an animal having the genetic defect. To effect retrotransposition in a cell in vivo in an animal for treatment of the animal, the DNAc molecule of the invention is administered to the animal using technology known in the art and described, for example, in the following references (WO 94 28938 and U.S. Pat. No. 5,240,846), each of which is hereby incorporated herein by reference. Upon administration to the animal in the formulations described herein, the L1 cassette portion of the DNAc molecule which is taken up by the target cells subsequently undergoes retrotransposition.

By the term "correction of a genetic defect" as used herein, is meant expression of a wild type gene product in a cell in an amount to restore normal function to the cell, which function was considered to be abnormal due to the genetic defect. The term also applies to situations wherein the genetic defect in the animal is corrected by delivering a wild type copy of the defective gene to a cell type other than the actual cell expressing the defective protein. Expression of the wild type copy of the gene in the other cells, and secretion of the wild type protein expressed therein may also serve to correct a genetic defect in the animal.

The DNAc molecule may be administered as a naked molecule, it may be encapsulated in a protein or lipid formulation, a synthetic formulation or in any number of viral vectors, such as, for example, including, but are not limited to, adeno-associated virus, adenovirus, lentivirus, parvovirus, herpes simplex virus, retroviral LTRs, inverted terminal repeats, and other viral genome elements. The L1 may be packaged in any one of the viral vectors just described using technology which is commonly available in the art of viral vector-mediated gene delivery. Liposome encapsulation of the DNAc molecule of the invention will also serve to effect entry of the molecule into a cell. Liposome encapsulation formulations for DNA are well know in the art and may be purchased, with instructions for the use thereof, from a number of commercial suppliers.

Treatment regimes which are contemplated include a single dose or dosage which is administered hourly, daily, weekly or monthly, or yearly. Dosages may vary from 1 $\mu$g to 1000 mg/kg of body weight of the DNAc molecule of the invention, and will be in a form suitable for delivery of the compound to the animal. In a preferred approach the DNAc molecule is delivered to cells of interest ex vivo. As outlined above, cells to be corrected are harvested from the patient, the DNAc construct is transfected in the preferred vector or formulation, and the cells are reimplanted within the patient. The treatment regimens contemplated include the schedule and dosages outlined above.

The route of administration may also vary depending upon the disorder to be treated. The DNAc molecule is prepared for administration by being suspended or dissolved in a pharmaceutically acceptable carrier such as isotonic saline, isotonic salts solution or other formulations which will be apparent to those skilled in such administration. The compositions of the invention may be administered to an animal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema). Preferably, for treatment of patients having lung infection, the route of administration is intranasal delivery by aerosol or via the blood. The appropriate pharmaceutically acceptable carrier will be evident to those skilled in the art and will depend in large part upon the route of administration.

A method of identifying and cloning genes which may be heretofore unknown or unclonable is also contemplated by the invention. Such a method comprises adding to cells the DNAc molecule of the invention, wherein the DNAc molecule is designed to effect random insertion of a detectable sequence or a "tag" into a cellular genome. The DNA referred to as "tag" DNA is that which is inserted into the 3' UTR of the L1 cassette. Such tag DNAs include, but are not limited to, neo$^R$, the GFP gene, lacZ, and the like. Following retrotransposition of tag DNA into cells, cells having the tag sequence inserted in the genome therein are identified using any number of techniques which are well known in the art. For example, hybridization may be used wherein a probe comprising tag DNA is used to identify cells having tag DNA or RNA. Where the tag DNA is expressed as protein, any number of immunological techniques may be used to identify cells expressing tag protein. Such technology is well known in the art and is described, for example, in Sambrook et al. (supra). The DNA flanking tag DNA may be isolated and cloned using ordinary technology described in, for example, Sambrook (supra), thereby effecting isolation and characterization of genes and regions of DNA which may be heretofore unknown.

Also contemplated in the invention is a method of generating large numbers of individual clones of cells, i.e., a library of cells, each of which cells comprises a "knocked out" or mutated gene. To generate a library of cells comprising individual mutations, the L1-containing DNAc molecule of the invention, especially gene and promoter trap vectors, is added to cells in a manner to effect random insertion of a specific DNA sequence into the cellular DNA. The DNA sequence to be inserted into the cells, i.e., the DNA sequence positioned in the 3' UTR or between the 3' UTR and the poly A signal of the L1 element, i.e., the tag DNA, comprises a known sequence which is suitable for PCR. The cells are transfected with the DNAc molecule of the invention, transfected cells containing retrotransposon events are cloned from the mixture using ordinary cell culture cloning technology, and cell DNA is obtained from each clone. PCR or reverse transcriptase (RT) PCR is performed on cell DNA or RNA so obtained using a primer which hybridizes to the L1-containing tag DNA to effect synthesis of the specific region of cell DNA which directly flanks the site of insertion of the L1-containing DNA. The identity of the flanking DNA so obtained may be established by hybridization of that DNA to a library of known DNAs. This type of screening hybridization may even be accomplished using an array of different probes on a microchip (Chee, 1996, Science 274:610–614). In this manner, a bank of cell clones is produced, each of which clones comprises a specific mutation which results from the insertion of L1 containing DNA.

It is not necessary that each and every mutation be identified in each and every clone of cells obtained according to the method described herein. Rather, cell clones so obtained may be stored for an indefinite length of time. As new genes and new functional regions of DNA are discovered, the cell clones may be tested for the presence or absence of mutations in genomic sites corresponding to such genes and functional regions of DNA. Moreover, it will be appreciated that upon identification of a mutated region of DNA using the methods described herein, it is then possible to isolate not only the mutated DNA, but in addition, it is possible to isolate wild type DNA which corresponds to the mutated DNA. Thus, the generation of cell clones according to the method of the invention provides a means of isolation and identification of both wild type and mutant forms of genes, which genes may be heretofore known but not isolated, or may even be heretofore unknown.

By the term "suitable for PCR" as used herein, is meant DNA for which primers may be easily obtained in order that PCR may be performed on the DNA.

Cell clones obtained according to the method of the invention are useful for the isolation of specific cellular DNA which may have a variety of uses in research, diagnostic and therapeutic applications. In addition, cell clones are useful for the generation of transgenic animals, which animals have a variety of uses in research, diagnostic and therapeutic applications. Thus, a transposon mutagenesis system in cells using the DNAc molecule of the invention is useful for the development of transgenic breeder stocks, thereby providing animal models useful in the elucidation of animal and human gene function and evaluation of targets for gene therapy or classical drug intervention.

The generation of transgenic animals is well known in the art and is described, for example, in Palmiter et al., (1986, *Ann. Rev. Genet.* 20:465–499). Essentially, a transgenic animal is generated by introducing a chimeric gene into the male pronucleus of a fertilized embryo. The embryo is next implanted into a pseudopregnant mammal of the same species from which the egg was obtained, which mammal then gives birth to the transgenic mammal. A chimeric gene is one which comprises the desired DNA sequence to be inserted into the cells of the animal and additional sequences such as, promoters and the like, which render the chimeric gene suitable for introduction into the cells of the animal and therefore, for generation of the transgenic animal.

The invention further includes a method of assessing the mutagenic potential of an animal by assessing the frequency of retrotransposition in the cells of that animal. Since L1 elements are capable of random insertion into a cell genome, they are potentially mutagenic. Thus, retrotransposition may be used as a measure of mutagenic potential in an animal. To assess the mutagenic potential of an animal, for example, genetic variants of mice, cells are obtained from the animal and are transfected with the DNAc molecule of the invention having a marker gene inserted in the L1 cassette portion. The frequency of retrotransposition in cells so transfected is assessed as a measure of the mutagenic potential of the cells.

The invention also includes a method of identifying a compound having anti-mutagenic activity. By the term "anti-mutagenic compound" as used herein, is meant a compound which when added to a cell, effects a reduction in the mutation frequency in the genome of the cell. The identification of a compound having anti-mutagenic activity may be accomplished by adding to a population of cells the isolated DNAc of the invention comprising an L1 cassette having a marker gene inserted therein. The DNAc molecule is added to the cells in the presence or absence of a test anti-mutagenic compound and the frequency of retrotransposition is assessed, using the marker gene, as a measure of the mutagenic capability of the cell. The test compound is considered to have anti-mutagenic activity when the frequency of retrotransposition in the cells in the presence of the test compound is lower than the frequency of retrotransposition in cells in the absence of the test compound.

According to the present invention, it is also possible to tag genes having a specific function with a selectable marker. For example, the basic premise of the experiment is to tag genes encoding proteins which function on the cell surface (receptors), mitochondria, peroxisomes, lysosomes, etc. using the "gene trap" construct to generate fusion proteins. Then one can identify the presence of the 'marker' fusion protein in the specific cell compartment. In one approach, the "marker" gene can be GFP and the specific site of expression of the fusion protein can be detected by fluorescence. In another approach, the "marker" gene can be a cell surface receptor and the fusion protein can be detected by use of an antibody to the "marker" protein. In the latter case, fluorescence activated cell sorting will be useful in detection of a small number of cells responding to the antibody among a large number of negative cells. In this way, localization of the 'marker' fusion protein to the cell surface will identify other potentially unknown receptor molecules. Proteins so expressed are useful targets for the identification of compounds which bind the protein and therefore are useful for the design of compounds capable of interacting with the protein in a drug design method. Thus, this technique provides a way to screen insertion libraries for genes of interest depending upon the cellular location of the engineered tag, and to provide a rational method for drug design.

EXPERIMENTAL DETAILS

According to the present invention, a retrotransposition assay in cultured human cells has been developed for the elucidation of the L1 sequence elements required for efficient retrotransposition. This assay can be used for the determination of retrotransposition rates of other newly isolated putative active elements. This assay is also a necessary component in the design, evaluation, development and optimization of retrotransposition based gene delivery vectors as discussed herein.

These data which are presented in the experimental details section establish that L1.2 is capable of autonomous, high frequency retrotransposition in cultured human cells. The experiments demonstrate that the only other known transpositionally active human L1 element, LRE2, is also capable of high frequency retrotranspositions in this assay. These results are unexpected, since data from a Ty1-based yeast heterologous assay system suggest that the protein encoded by the second ORF of LRE2 contains little reverse transcriptase (RT) activity. The finding that LRE2 retrotransposes as well as L1.2 in HeLa cells indicates that RT is not rate limiting for L1 retrotransposition as once believed. The assay of the present invention thus provides a more accurate assessment of L1 retrotransposition than prior art methods such as the Ty1-based yeast assay. Also unexpected in the present discovery is the fact that retrotransposition of human L1 elements is not restricted to human cells, in that, the data presented herein also establish that retrotransposition of L1 elements occurs in mouse cells.

Also included in the experiments described herein is a method for identification of heretofore unknown L1 elements in cells.

It should be appreciated that the invention should not be construed to be limited to the examples which are now described; rather, the invention should be construed to include any and all applications provided herein and all equivalent variations within the skill of the ordinary artisan.

EXAMPLE 1

High Frequency Retrotransposition in Cultured Animal Cells

The materials and methods used in the experiments presented in Example 1 are now described.

Oligonucleotides and Plasmids

L1.2A (Dombroski et al., 1991, *Science* 254:1805–1808) was engineered to contain a unique NotI restriction site up stream of its 5' UTR or immediately upstream of ORF1. The BamHI site at position 4836 of L1.2 was then destroyed by site-directed mutagenesis thereby changing the sequence 5' GGATCC to 5' GGACCC and leaving a unique BamHI site flanking the 3' end of the element (in the polylinker of pBLS KS−). A unique SmaI site was introduced into the L1.2 3' UTR at position 5980 by site-directed mutagenesis thereby changing the sequence 5' CCTGCA to 5'-CCCGGG. A blunted-ended 2.1 kb EcoRI-BamHI fragment containing the neo indicator cassette (Holnes, Thesis Dissertation, Johns Hopkins University Press, 1994) was cloned into the SmaI site, resulting in plasmids that contained a tagged L1.2 element that either had (pJCC9) or lacked (pJCC8) the L1.2 5' UTR. Subcloning of the 8.1 kb NotI-BamHI fragment from pJCC9 or the 7.2 kb NotI-BamHI fragment from pJCC8 into pCEP4 (In Vitrogen) created pJM101 and pJM102, respectively. A 0.75 kb BglII restriction fragment was deleted from pCEP4 creating pCEP4ΔCMV. Subcloning of the 8.1 kb NotI-BamHI fragment from pJCC9 or the 7.2 kb NotI-BamHI fragment from pJCC8 into pCEP4ΔCMV created pJM101ΔCMV and pJM102ΔCMV, respectively. Deletion of a 3.8 kb AflII fragment from pJM101 yielded pJM103. Replacement of the 5.9 kb fragment in pJM101 with a 5.9 kb AccI fragment from LRE2 (Holmes et al., 1994, Nature Genetics 7:143–148) created pJM104. Deletion of the 145 bp downstream of the stop codon in pJM102 created pTN101.

All of the ORF1 and ORF2 mutations were generated by site-directed mutagenesis (Kunkel, et al., 1991, *Methods in Enzymology* 204:125–139) and relevant restriction fragments containing the mutation were sequenced in their entirety. Each mutant was subcloned into pJCC8, and the 7.2 kb NotI-BamHI fragment of each mutant was cloned into pCEP4.

DNA Preparation and Sequencing

Plasmid DNAs were purified on Qiagen maxi or mini prep columns. DNAs for transfection experiments were checked for superhelicity by electrophoresis on 0.6% agarose/ ethidium bromide gels. Only highly supercoiled preparations of DNA (>90%) were used in transfection experiments. Genomic DNA obtained from tissue culture cells was isolated using established methods (Sambrook et al., 1989, supra). DNA sequencing was done using an ABI DNA sequencer (ABI 377).

Growth of Cells

HeLa cells and mouse LTK- cells were grown at 37° C. in an atmosphere containing 7% carbon dioxide and 100% humidity in DMEM-high glucose medium lacking pyruvate (Gibco/BRL). DMEM was supplemented with 10% fetal bovine calf serum (FCS), 0.4 mM glutamine, and 20 U/ml penicillin/streptomycin (DMEM-complete). Cells were passaged by standard methods.

Transfection of Cells and Assay Conditions

HeLa cells (2–4×10$^5$ cells/well) were seeded in six well dishes and grown to 70% confluency in DMEM-complete. Cells were transfected using the lipofectamine transfection reagent (Gibco/BRL). Each transfection consisted of 1 ml of Opti-mem (Gibco/BRL) containing 1 μg of DNA and 7 μl of lipofectamine reagent. Five hours after transfection, 1 nil of DMEM-complete containing 20% FCS was added to each set of cells. After 16 hours, the medium was replaced with 2 mls of DMEM-complete. Three days after transfection, Hyg$^R$ cells were selected by growth in DMEM-complete containing 200 μg/ml hygromycin (DMEM-Hyg). After 12–14 days, the Hyg$^R$ cells were trypsinized, pooled and expanded in DMEM-Hyg for 7 days. Hyg$^R$ cells were trypsinized, counted with a hemocytometer, and dilutions were plated in DMEM-complete containing 300–400 μg/ml G418 (DMEM-0418). After 10–14 days, the G418$^R$ cells were fixed to plates and stained with 0.4% Giemsa for visualization. The number of G418$^R$ colonies was scored and the retrotransposition frequency was determined as described herein. Modifications of this assay are also described herein. As a transfection control, β galactosidase activity from a CMV-lacZ reporter was assayed 3 days post-transfection (Swergold, 1990, Mol. Cell. Biol. 10:6718–6729). The typical transfection efficiency was 5–10%.

PCR Analysis

PCR reactions were carried out in 50 μl volumes. Each reaction contained 10 units of Taq polymerase, 0.2 mM dNTPs, and 200 ng of each primer in the buffer supplied by the vendor (Perkin-Elmer). In general, reactions were carried out at an annealing temperature 5° C. below the Tm of the primer. One-fifth of the reaction volume was separated on 1.0% agarose gels containing ethidium bromide.

Southern Blot Hybridization Analysis

DNA samples were restricted with the appropriate restriction enzymes (New England Bio Labs) and samples were fractionated on 0.7%–1.0% agarose gels containing ethidium bromide. Southern blots were performed as described in Sambrook et al., 1989, supra). DNA probes to the neo gene were labeled using the multiprime DNA labeling system (Amersham) to high specific activity with ($\alpha^{32}$P-dCTP (Amersham).

Library Construction and Screening

EcoRl restriction fragments containing the L1.2mneoI insertions were isolated from agarose gels using GeneClean (Bio 101 Inc.), were checked for the spliced neo gene by PCR (as in FIG. 4B), and were cloned into the following phage: $\lambda$gt10 (Promega; insertion B), $\lambda$-II (Stratagene; insertions C and D), or $\lambda$zap II (Stratagene; insertion A). Phage were packaged using either Promega Packagene or Stratagene Gigapack III packaging extracts and plated at a density of 10,000–30,000 phage/plate. Approximately 200–800,000 clones from each library were screened with a 0.46 kb neo gene (Sambrook et al., 1989). Secondary and tertiary screens were used to further purify positive clones.

Characterization of Empty Genomic Sites in HeLa DNA

The empty sites for insertions A–D were amplified by PCR using oligonucleotide primers that flanked the insertion site. The sequence flanking each empty site was checked for repetitive sequences using the BLAST algorithm (BCM search launcher) to scan the sequences in GenBank and an EST database (Altschul, et al., 1990, *J Mol. Biol.* 215:403–410). Sequences in non-repetitive DNA flanking each insertion were used to design oligonucleotide probes. Those probes were used in PCR reactions with HeLa cell genomic DNA. In every case, a single band of the predicted size was amplified.

Genomic localization of the L1.2mneoI retrotransposition Events

Insertions were mapped using PCR on 100 ng of genomic DNA from a monochromosomal human-rodent somatic cell hybrid panel purchased from the Coriell Cell Repositories. For each retrotransposition event, primers were chosen in the vicinity of the insertion site from presumptive single copy sequences after database searches.

The results of the experiments presented in Example 1 are now described.

A System to Detect L1 retrotransposition

To determine if L1.2 could retrotranspose, in cultured cells, a reporter cassette (mneoI) designed to detect rare retrotransposition events (Freeman et al., 1994, *BioTechniques* 17:47–52) was cloned into the 3' UTR of L1.2 to create L1.2mneoI (FIG. 1B). The reporter cassette comprises an antisense copy of a selectable marker (neo), a heterologous promoter (P') and a poly Adenylation signal (A'). The neo gene is disrupted by an intron (IVS 2 of the $\gamma$-globin gene) in the opposite transcriptional orientation (FIG. 1B). This arrangement ensures that G418-resistant cells (G418$^R$) will only arise when a transcript initiated from the promoter driving L1.2 mneoI expression (P) is spliced, reverse transcribed, reintegrated into chromosomal DNA, and expressed from promoter P'. In contrast, transcripts originating from P' cannot be spliced, the neo gene product cannot be synthesized, and the cells will remain sensitive to G418. Similar cassettes have been used previously to document the formation of processed pseudogenes in yeast and mammalian cells, and to demonstrate retrotransposition of yeast, Drosophila, and mouse retroelements (Boeke et al., 1985, *Curr. Opin. Cell. Biol.* 3:502–507; Heidmann et al., 1988, *Proc. Natl. Acad. Sci. U.S.A.* 85:2219–2223; Curcio et al., 1991, *Proc. Natl. Acad. Sci. U.S.A.* 88:936–940; Derr et al., 1991, *Cell* 67:355–364; Jensen et al., 1991, *EMBO J.* 10:1927–1937; Tchenio et al., 1993, *EMBO J.* 12:1487–1497; Maestre et al., 1995, *EMBO J.* 14:6333–6338).

To achieve high-level expression of L1.2mneoI, and to avoid the variable expression phenotypes that typically plague studies using stably transfected cell lines, L1.2mneoI was subcloned into the pCEP4 expression vector to create pJM101 (FIG. 2A). The plasmid pCEP4 was chosen because it replicates as a moderate copy number, extrachromosomal nuclear episome in primate cell lines (Yates et al., 1985, Nature 313:812–815) and contains a hygromycin gene (hyg) for the selection of transfected cells. In pJM101, the expression of L1.2mneoI was controlled by the cytomegalovirus immediate early (CMV) promoter. Polyadenylation of L1.2mneoI could occur at either the native L1.2 poly A site or at the SV40 poly A site present in pCEP4 (FIG. 2A.).

To avoid complications due to the expression of endogenous L1 elements, L1.2mneoI was tested for retrotransposition in a cultured human cell line, HeLa, that does not express endogenous L1s at high levels (Swergold, 1990, *Mol. Cell. Biol.* 10:6718–6729; Liebold et al., 1990, *Proc. Natl. Acad Sci. U.S.A.* 87:6990–6994). Moreover, RL1-defective mutant alleles of L1.2mneoI were constructed to test whether G418$^R$ foci could result through complementation by other cellular reverse transcriptases.

L1.2mneoI (pJM101) and three mutant constructs were tested initially for their ability to retrotranspose (FIG. 2B). The first mutant (pJM102) lacks the internal promoter sequences present in the 910 bp 5' UTR of L1.2. The second mutant (pJM103) contains a 3.8 kb deletion of L1.2 sequence that eliminates most of the 5' UTR, all of ORF1, and the first 2.1 kb of ORF2. The third mutant (pJM105) contains a missense mutation (D702Y) in the RT domain of the ORF2 protein (Mathias et al., 1991, *Science* 254:1808–1810).

Figure 3A:
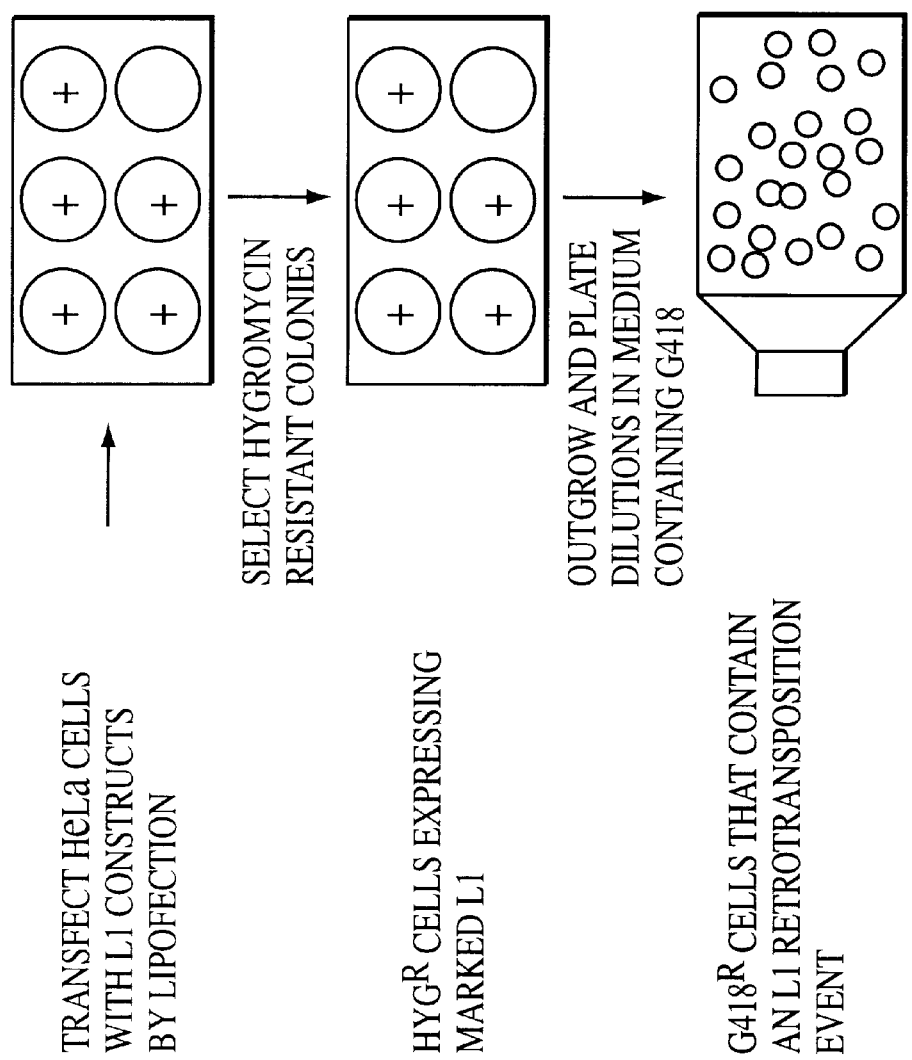
FIG. 3A is a diagram outlining the L1.2mneoI retrotransposon assay. HeLa cells were transfected with the desired constructs using lipofectamine. Hygromycin-resistant (hyg$^R$) cells expressing the wild type and mutant constructs of L1.2mneoI were harvested 12–14 days later.
Figure 3B:
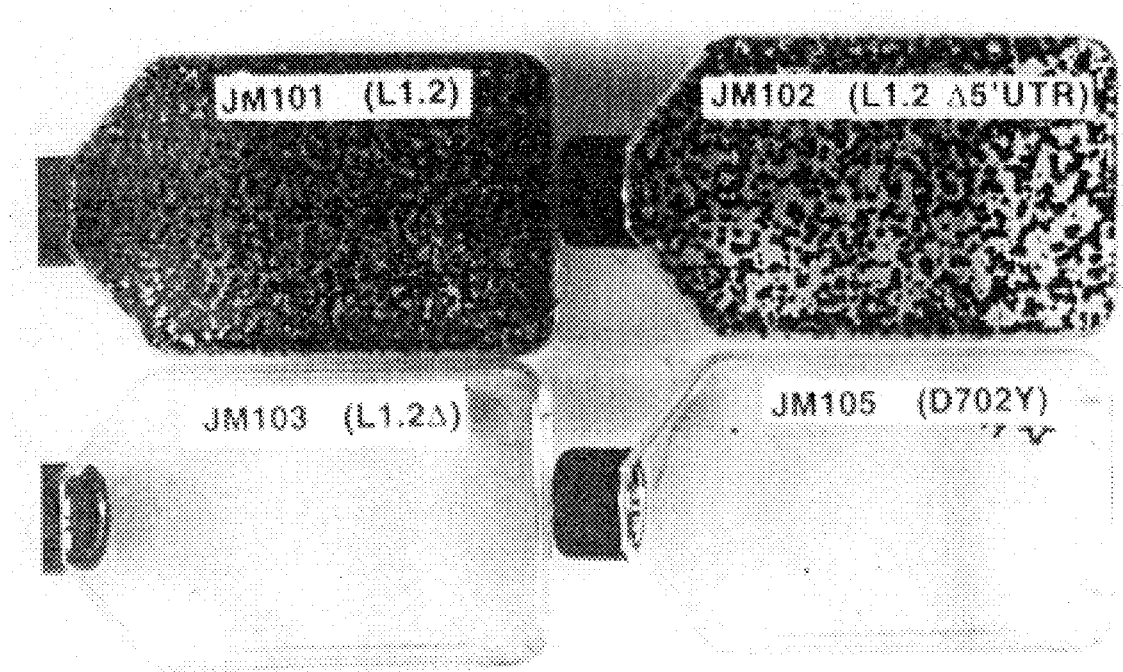
FIG. 3B is an image of the results of the retrotransposition assay. G418$^R$ foci were fixed to flasks and stained with Giemsa for visualization. Flasks containing cells transfected with pJM101, pJM102, pJM103 and pJM105 are shown.

The wild type and mutant constructs and the pCEP4 vector were transfected into HeLa cells and were tested for their ability to retrotranspose using the selection scheme outlined in FIG. 3A. Several thousand independent hygromycin-resistant cells (at least 5000–10000 cells per transfection) expressing the constructs were harvested 12–14 days after transfection, pooled, and expanded in growth medium supplemented with hygromycin. Serial dilutions of the Hyg$^R$ cells were plated in medium containing G418 and after 14 days the resistant cells were fixed and stained (FIG. 3B). The retrotransposition frequency was then scored as the number of G418$^R$ colonies per 10$^6$Hyg$^R$ cells plated (Table 1).

Apparent retrotransposition (FIG. 3B; Table 1) was readily observed in cultures expressing pJM101 (about 740 events in 10$^6$ cells) or pJM102 (about 335 events in 10$^6$ cells), but not in HeLa cell lines that expressed the deletion (pJM103) or RT-defective mutant (pJM105) (<1 event in 10$^6$ cells). Moreover, G418$^R$ foci were never obtained from cells expressing pCEP4. These data indicate that L1.2mneoI autonomously retrotransposes in HeLa cells and that the events depend upon the RT encoded by ORF2.

TABLE 1

Retrotransposition frequencies of different L1.2mneoI constructs in HeLa and LTK-cells. Individual constructs tested are listed in column 1. The letter N = the number of independent transfections for each construct. ND = No $G418^R$ colonies recovered. The retrotransposition frequencies of each of the constructs used in this study (column 3), the experimental range (column 4), and the percent wild-type activity (column 5) are reported. The retrotranspositional activity was normalized to the frequency observed for JM101.

| CONSTRUCT | N | RETROTRANSPOSITION FREQUENCY X $(10^{-6})$ | EXPERIMENTAL RANGE X $(10^{-6})$ | PERCENT WILD TYPE ACTIVITY |
|---|---|---|---|---|
| pJM101 (L1.2) | 19 | 740 | 390–1090 | 100% |
| pJM102 (L1.2Δ5'UTR) | 21 | 335 | 110–560 | 45% |
| pJM103 (L1.2Δ) | 6 | <0.2 | <0.2 | <0.03% |
| pJM104 (LRE2) | 3 | 1140 | 980–1300 | 154% |
| pJM105 (D702Y) | 20 | 0.5 | 0.2–0.8 | 0.07% |
| pJM101ΔCMV | 4 | 443 | 360–550 | 60% |
| pJM102ΔCMV | 2 | N.D. | N.D. | N.D. |
| pCEP4 | 4 | N.D. | N.D. | N.D. |
| MOUSE-L-CELLS | | | | |
| pJM101 | 2 | 343 | 240–446 | 46% |
| pJM102 | 2 | 75 | 59–90 | 10% |
| pJM105 | 3 | N.D. | N.D. | N.D. |

L1.2mneoI Retrotransposes into Genomic DNA

To determine whether L1.2mneoI integrated into chromosomal DNA or episomal DNA, genomic DNA was isolated and pooled from approximately 10–20 $G418^R$ foci derived from either pJM101 or pJM102. The DNA was digested with BamHI, and Southern blot analysis was performed using a neo probe. About 8–12 bands of differing intensity were present in DNAs of $G418^R$ cells, but not in HeLa cell DNA. The presence of multiple bands suggested that L1.2mneoI integrated into multiple chromosomal locations. This analysis was repeated on 17 individual $G418^R$ foci isolated from a single experiment and 15 of 17 foci contained distinct fragment sizes indicating that the vast majority, or all, of the $G418^R$ foci result from independent retrotransposition events.

To facilitate cloning of the L1.2mneoI retrotransposition events, the assay depicted in FIG. 2B was modified wherein $G418^R$ foci were directly selected three days after transfection. By eliminating the hygromycin selection step, $G418^R$ cells that contain a retrotransposition event were enriched in the population of cells compared with cells that either lacked or contained reduced amounts of the original vector. Confirming the previous results, $G418^R$ foci were obtained from HeLa cells expressing pJM101 and pJM102, but not from cells expressing pJM103 or pJM105.

DNA was isolated from four independent $G418^R$ clones derived from HeLa lines that transiently expressed pJM102. The DNA was digested with EcoRI and Southern analysis was performed using a neo probe. One major restriction fragment was observed in the DNA samples from each clone (FIG. 4A). The fragment sizes ranged from 4.1 kb (clone B) to >12 kb (clone D), differed from the predicted size of the vector fragment (~10 kb), and were not detected using pCEP4 vector sequences as a probe. PCR analysis of these DNAs confirmed the loss of the γ-globin intron (FIG. 4B). Together, these data indicate that L1.2mneoI retrotransposes into numerous sites in chromosomal DNA.

Retrotransposed Copies of L1.2mneoI are 5' Truncated and End in a Poly A Tail

To determine the genomic structure of the retrotransposed copies of L1.2mneoI, the insertions from events A-D (FIG. 4A) were cloned and 5' junction sequences were identified.

Figure 5:
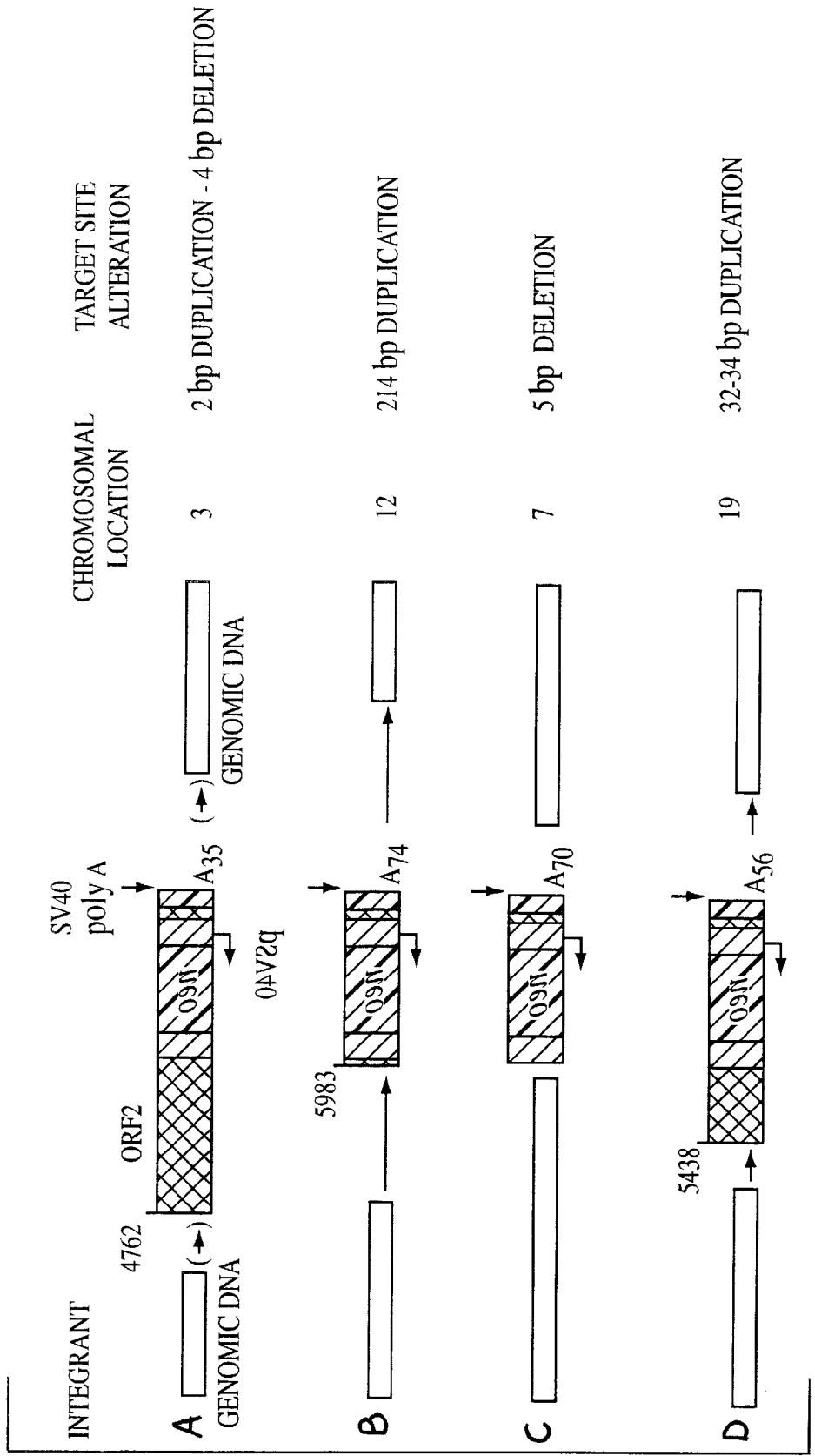
FIG. 5 is a diagram depicting the genomic structures of the insertions A–D. Each insertion was compared to its corresponding 'empty site' which was independently cloned from HeLa cell genomic DNA. Truncated portions of L1.2mneoI are shown and the nucleotide position of the truncation in L1.2 is noted. Cross-hatched rectangles are L1.2 sequences and evenly hatched rectangles are the SV40 promoter and SV40 poly A signal at the two ends of the antisense neo gene. Unevenly-hatched rectangles are transduced sequences between the 3' end of L1.2 and the poly A site derived from the pCEP4 vector. Open rectangles represent genomic DNAs. Rightward arrows indicate target site duplications. The length of the poly A tracts and the sizes of the target site duplications and/or deletions are indicated. The arrow flanking insertion A is marked parenthetically because the target site could be a 1–2 bp duplication, a blunt insertion or up to a 4 bp deletion.

Each retrotransposed L1.2mneoI insertion: (1) contained the entire neo coding sequence as well as the SV40 promoter (P'); (2) was inserted into distinct genomic locations; and 3) was variably 5' truncated (FIG. 5). Insertion A is 2.88 kb and ends at position 4762 of L1.2; insertion B is 1.62 kb and ends at position 5983 of L1.2; insertion C is 1.59 kb and is truncated 7 bp after the neo poly Adenylation site; insertion D is 2.15 kb and ends at position 5438 of L1.2 (FIG. 5).

The 3' junction sequence of each insertion was obtained. Surprisingly, none of the insertions utilized the native L1 poly A site present in the 3' UTR of L1.2mneoI. Instead, each terminated with a variable length, perfect poly A tail added precisely to the SV40 late poly A cleavage site (Conway et al., 1985, Proc. Natl. Acad. Sci. U.S.A. 82:3949–3953 ) in pCEP4,138 bp downstream of the L1.2 3' UTR (FIG. 5). The sizes of the poly A tails were as follows: insertion A, 35–37 bp; insertion B, 74 bp; insertion C, 70 bp; and insertion D, 56 bp.

New Copies of L1.2mneoI Arise by de novo retrotransposition

To determine whether L1.2mneoI authentically retrotransposes into HeLa genomic DNA or integrates by gene converting pre-existing L1 elements, the following experiments were performed. Since each insertion contained SV40 sequences at its 3' terminus Gust prior to the poly A, tract), and 2 of the insertions have neo sequences at their 5' terminus, gene conversion was unlikely. To confirm that this was the case, each of the 'empty sites' present in HeLa genomic DNA was cloned, sequenced and the sequence was compared to the sequence flanking the insertions (FIG. 5). In every case, the empty site lacked endogenous L1 sequence at or immediately flanking the insertion site and was present on only one chromosome (see below).

Each L1.2mneoI retrotransposition resulted in an alteration of the target site sequence (FIG. 5). Insertion B was flanked by an unusually long target site duplication of 214 bp, while insertion D was flanked by a target site duplication of 32–34 bp residing in a T-rich stretch of DNA. In contrast, insertion C resulted in a short target site deletion of 5 bp. Since insertion A retrotransposed into a stretch of 6A residues, its target site could not be unambiguously determined. The insertion is flanked by two As at its 5' end and contains a poly A tail at its 3' end. For this reason, it was not possible to differentiate between: (1) a short duplication of 1 or 2 bp; (2) a small deletion of the target site of up to 4 bp; and (3) blunt-ended insertion that did not result in either a duplication or deletion of the target sequence. Although the variation in the structure of the target sites is greater than that seen with genomic L1s, the absence of L1 sequences at or near the target sites and the alterations created upon insertion clearly rules out integration via a gene conversion mechanism.

Retrotransposed Copies of L1.2mneoI Insert into Different Chromosomes

To determine whether L1.2mneoI retrotransposed into various chromosomes, primers were synthesized which are specific for genomic sequences flanking each of the insertions. The chromosomal locations of the flanking sequences were then mapped by PCR of DNA obtained from a monochromosomal rodent/human hybrid cell panel (Coriell Cell Repositories). In each case, a single band of the predicted size was seen in only one of the hybrid samples. Insertion A mapped to chromosome 3, insertion B mapped to chromosome 12, insertion C mapped to chromosome 7, and insertion D mapped to chromosome 19 (FIG. 5).

L1.2mneoI Retrotransposition Requires the ORF1 Protein

Figure 6:
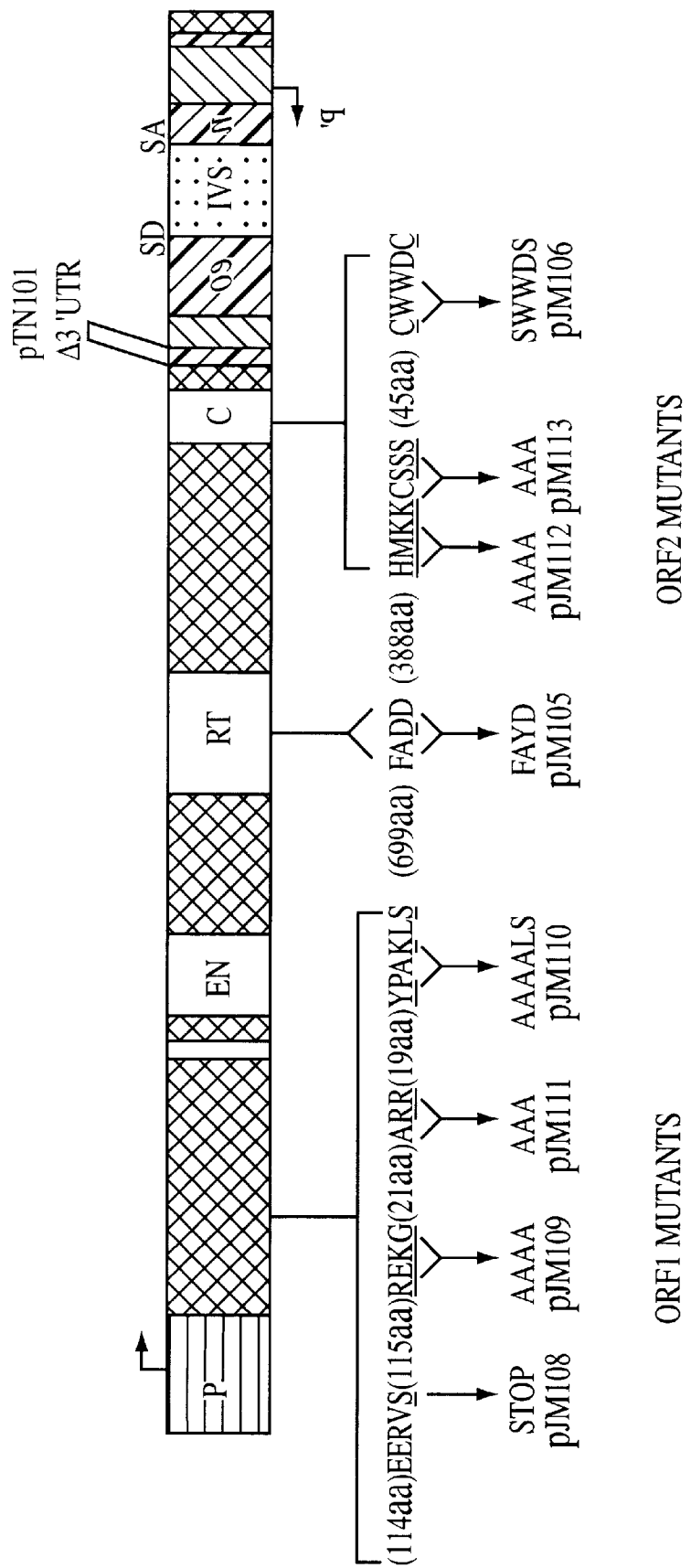
FIG. 6 is a diagram depicting mutant constructs of L1.2mneoI transfected into HeLa cells. The approximate positions of ORF1, ORF2 and Δ3' UTR mutants are indicated. Each mutant was constructed in the pJM102 backbone and lacks the 5' UTR sequence of L1.2. Wild type amino acids which were mutated are underlined and the resulting mutant sequence is shown below the underline.

L1.2 ORF 1 encodes a 40 kD nucleic acid binding protein (Holmes et al., 1992, *J. Biol. Chem.* 267:19765–19768; Hohjoh et al., 1996, *EMBO J.* 15:630–639). To determine whether this protein is critical for retrotransposition, a nonsense mutation was introduced into ORF1 and the mutant construct was assayed. pJM108 (S119X) has a stop codon at nucleotide 1265 of ORF1 which truncates the protein by 219 amino acids (FIG. 6). This mutation abolishes the ability of L1.2mneoI to retrotranspose in HeLa cells (Table 2).

To identify functionally important amino acids in the ORF1 protein, the amino acid sequence of L1.2 ORF1 was compared to the ORF1 sequences of mouse, rat, and rabbit L1s (Burton et al., 1986, *J. Mol. Biol.* 187:291–304; Demers et al., 1986, *Mol. Biol. Evol.* 3:179–190; Hohjoh et al, 1996, *EMBO J.* 15:630–639). This analysis revealed three conserved blocks of amino acids near the C-terminus of the ORF1 protein (ARR at residues 260–262, REKG at residues 235–238 and YPAKLS at residues 282–287). The conserved amino acids were each change to alanine to create pJM109, pJM110, and pJM111 (FIG. 6). Each mutant retrotransposed at less than 1% the frequency of the wild-type construct (Table 2), indicating that ORF1 is required for retrotransposition.

A Cysteine-Rich Motif in the C-Terminal End of ORF2 is Critical for Retrotransposition To define other regions of ORF2 critical for retrotransposition, mutations in the cysteine-rich region of ORF2 were generated. This region is highly conserved (Fanning et al., 1987, *Nucl. Acids Res.* 15:2251–2260). Two cysteine residues were changed to serine residues (CxxxC at residues 1143 and 1147 to SxxxS) to create pJM106. Two other conserved blocks of amino acids were also each changed to alanine: (HMKK at residues 1091–1094 to AAAA and SSS at residues 1096–1098 to AAA) to create plasmids pJM112 and pJM113 (FIG. 6). Each mutation significantly reduced the retrotransposition frequency (Table 2). However, a detectable number of events (about 1% wild-type levels) from pJM106 and pJM 112 was reproducibly recovered (Table 2).

The 3' UTR of L1.2mneoI is not Required for High Frequency Retrotransposition

The 3' UTR of R2Bm is critical for reverse transcription in vitro and presumably retrotransposition in vivo (Luan et al., 1993, *Cell* 72:595–605; Luan et al., 1995, *Mol. Cell. Biol.* 15:3882–3891). However, the observation that the native L1 poly A signal is bypassed in favor of the SV40 poly A signal in the pCEP4 vector suggested that the 3' UTR of L1.2 may be dispensable for retrotransposition. To ascertain the importance of the 3' UTR, 145 bp was deleted including a conserved polypurine tract (Usdin et al., 1989, *J Biol. Chem.* 264:15681–15687) from the 3'UTR of pJM102 to create pTN101 (FIG. 6). Interestingly, this deletion had little effect on the retrotransposition frequency of L1.2 (Table 2) indicating that the polypurine tract present in the L1 3' UTR is not required for retrotransposition in our assay.

TABLE 2

Retrotransposition frequencies of ORF1 and ORF2 mutants of L1.2mneoI constructs in HeLa cells. Individual constructs tested are listed in column 1. The letter N = the number of independent transfections for each construct. The percent wild-type activity is shown in column 3. The activity was normalized to the value reported for JM102 since all of the mutants were constructed in the pJM102 backbone.

| CONSTRUCT | N | PERCENT WILD-TYPE ACTIVITY |
|---|---|---|
| pJM102 | 21 | 100% |
| ORF1 MUTANTS | | |
| pJM108 (S119X) | 6 | <0.06% |
| pJM109 (REKG-AAAA) | 3 | 0.4% |
| pJM110 (YPAKLS-AAAALA) | 3 | 0.1% |
| pJM111 (ARR-AAA) | 3 | <0.06% |
| ORF2 MUTANTS | | |
| pJM105 (D702Y) | 20 | 0.15% |
| pJM106 (CxxxC-SxxxS) | 9 | 0.24% |
| pJM112 (HMKK-AAAA) | 3 | 1.0% |
| pJM113 (SSS-AAA) | 3 | 0.2% |
| 3' UTR MUTANT | | |
| pTN101 | 4 | 90% |

The L1 Promoter is Sufficient for Retrotransposition in HeLa Cells

The L1 5' UTR contains a promoter (Swergold, 1990, *Mol. Cell. Biol.* 10:6718–1729; Minakarni et al., 1992, *Nucl. Acids Res.* 12:3139–3145). To determine whether the L1 promoter was sufficient for retrotransposition, the CMV promoter was deleted from pJM101 to create pJM101ΔCMV. The retrotransposition frequency of pJM101ΔCMV was about 60% of that of pJM101 (Table 1). A construct lacking both the CMV promoter and the 5' UTR (pJM102ΔCMV) was unable to retrotranspose (Table 1), confirming that the promoter activity in pJM101ΔCMV resides in the 5' UTR and not elsewhere in the vector, LRE2 Retrotransposes at a High Frequency in HeLa cells LRE2 is another potentially active L1 element. To determine whether this element could retrotranspose in HeLa cells, the following experiment were performed. LRE2 contains two intact reading frames, the encoded proteins of which differ from L1.2 at 17 amino acids residues, but none of these differences occur in conserved functional domains (Holmes et al., 1994, *Nature Genetics* 7:143–148). LRE2 was tagged with the indicator cassette, cloned into pCEP4 (pJM104), and assayed for retrotransposition. LRE2 retrotransposes at a higher frequency than L1.2 (about 1140 events in $10^6$ cells as compared to 740 events in $10^6$ cells; Table 1) despite its lower RT activity. These data establish that at least two retrotranspositionally active L1 elements reside in the human genome.

A Human L1 Element Retrotransposes in a Mouse Fibroblast Cell Line

The observation that retrotransposition events in HeLa cells occur at numerous, distinct chromosomal locations led to the investigation of whether L1 elements can be used for transposon mutagenesis. In a first step toward developing this technology, it was necessary to determine whether L1.2mneoI is capable of retrotransposition in a cultured mouse fibroblast cell line (L-cells). The plasmids pJM101, pJM102, pJM103, pJM105 and pCEP4 were transfected into mouse LTK- cells and were tested for retrotransposition using the selection scheme described in FIG. 3A. A high-frequency of G418$^R$ foci were obtained from cell-lines expressing the wild-type constructs, but not from cell lines expressing the mutants (Table 1). Southern analysis and PCR were used to confirm that L1.2mneoI integrated into different chromosomal locations of the LTK- genome and lacked the intron present in the original construct. Since the human L1s retrotranspose in mouse cells, these data suggest that cellular factors involved in the retrotransposition process are evolutionarily conserved.

EXAMPLE 2

Human L1 Retrotransposon Encodes A Conserved Endonuclease Required For Retrotransposition It has been discovered in the present invention and is exemplified in Example 2, that an endonuclease domain important to retrotransposition by L1, has been identified at the L1 ORF2 terminus that is highly conserved among poly A retrotransposons and resembles the apurinic/apyrimic (AP) endonucleases.

The materials and methods used in Example 2 are now described.

PCR Amplification of the L1 EN Domain (plasmids and strains)

The L1 EN domain was PCR amplified with primers JB1073 5'-CCTCATGACAGGATCAAATTCACAC-3' (SEQ ID NO: 132-11) and JB1083 5'-GCCCATGGCAATCCTGAGTTCTAGTTTG-3' (SEQ ID NO: 133-12) from the pL1.2 A DNA plasmid and was cloned into the pCR(II) vector (Invitrogen, San Diego) to yield the plasmid pQF218. Five different point mutations (FIG. 7) in the L1 EN domain were introduced using site-directed mutagenesis. Each mutation was PCR amplified with primers JB1073, JB1083, and cloned into the pCR(II) vector. All PCR products were verified by DNA sequencing. For expression of L1 ENp and mutant proteins in *E. coli*, the BspHI -NcoI fragments from pQF218 and its mutant derivatives were cloned into the NcoI site of pET15b (Novagen, Madison, Wis.) and the resulting constructs were transformed into strain BL21(DE3) for protein production.

Expression and Purification of L1 ENp

Induction and purification of His$_6$-tagged protein was performed in accordance with the protocol described by Qiagen (Cat. No. 30201 Chatsworth, Calif.). Cells were grown at 37° C. in LB containing 50 mg/ml ampicillin to an $A_{600}$ of 0.8. IPTG was added to a final concentration of 1 mM for another 3 hours. Cells were then pelleted and stored at −20° C. Cells from a 10 ml culture were thawed at 0° C. for 30 minutes, resuspended in 0.3 ml buffer (50 mM sodium phosphate, pH 8.0, 300 mM NaCl), and disrupted by sonication for 30 seconds. The clarified supernatant (12,000 rpm, 20 minutes) was mixed with 0.1 ml pre-equilibrated Ni-agarose (Qiagen, Chatsworth, Calif.) at 4° C. for 1 hour. The Ni-agarose was centrifuged, and washed twice with 0.5 ml sonication buffer, twice with 0.5 ml washing buffer (50 mM sodium phosphate, 300 mM NaCl, 10% glycerol, pH 6.0), twice with 0.5 ml washing buffer containing 0.7 M NaCl, and twice with 0.5 ml washing buffer containing 30 mM imidazole. Finally the protein was eluted with 0.25 ml washing buffer containing 100 mM imidazole and 0.25 ml washing buffer containing 150 mM imidazole. Most protein was eluted in the 100 mM imidazole fraction. Either eluted fraction was directly used in the endonuclease nicking assay.

Nicking Assay

Supercoiled pBS DNA substrate (Bluescript KS-, Stratagene) was prepared by double-banding in cesium chloride/ethidium bromide as described in Maniatis et al. (1982, Molecular cloning: A Laboratory Manual, Cold Spring Harbor, N.Y., pp. 1–545). Partially depurinated DNA (AP-DNA) preparations of pBS was prepared by incubation of purified supercoiled DNA in 8 mM Tris-HCl, pH 7.5, 0.8 mM EDTA, 20 mM sodium citrate, pH 5.0, and 0.2 M NaCl for 20 minutes at 70° C., followed by chilling on ice in accordance with procedures described by Johnson et al. (1988, J. Biol. Chem. 263:18017–18022. The extent of AP-DNA generated was determined by the minimum amount of depurination leading to quantitative conversion of supercoiled DNA to nicked circles upon treatment with Exo III.

The L1 EN reaction mix contained 50 mM Hepes-KOH, pH 7.6, 50 mM KCl, 5 mM MgCl$_2$, 100 μg BSA, 0.2 μg supercoiled DNA and 20 ng purified protein in a total reaction volume of 25 μl at 37° C. for 20 minutes or as indicated. The reaction was stopped by addition of 25 mM EDTA or heating to 69° C. for 10 minutes. Half the reaction mixture was loaded on a 1% agarose gel in TTE buffer containing 0.5 μg/ml ethidium bromide. For the ligation experiment, after the supercoiled DNA was incubated with L1 ENp, it was heated at 69° C. for 10 minutes to inactivate the residual L1 ENp activity. T4 DNA ligase and 1 mM ATP were added and incubated at 16° C. overnight. Subsequently, the T4 DNA ligase was heat inactivated, and L1 EN was added to the reaction as indicated.

The AP-endonuclease activity of Exo III was assayed as follows: the reaction mix contained 50 mM Tris-HCl, pH 8.0, 5 mM CaCl$_2$, 1 mM β-mercaptoethanol, 0.2 μg AP-DNA, and 1 μl Exo III (100 U/μl, NEB) in 25 μl. The reaction was incubated at 37° C. for 20 minutes.

Determination of Specificity of Cleavage Sites

L1 ENp-digested supercoiled DNA was run on gels and liner products were electroeluted and digested with various restriction enzymes. Primer extension using Taq polymerase was performed on nicked and linear DNA generated from L1 ENp cleavage using kinased primers JB1132 5'-TCTTTTCTACGGGGTCTG-3' (SEQ ID NO: 134-13), JB1133 5'-CAGGCAACTATGGATGAA-3' (SEQ ID NO: 134-14) and the T7 primer, 5'-AATACGACTCACTATAG-3' (SEQ ID NO: 135-15). The reaction mix was loaded side by side with a sequencing reaction on supercoiled DNA carried out using the same $^{32}$P-labeled primers; cleavage sites were determined by comparison to these standards. For the K-DNA, primer SP6 5'AGCTATTTAGGTGACACTATAG-3' (SEQ ID NO: 137-16) was used.

Tissue Culture Analysis of Transposition

Wild-type and mutant derivatives of the pL1.2 mneoI plasmid were introduced into HeLa cells by lipofection and hygromycin resistant cell populations were obtained as described herein. The e.o.p (efficiency of plating) of these cells on G418-containing medium was then measured to obtain the reported transposition frequencies.

The results of the experiments presented in Example 2 are now described.

Poly A Elements Encode an AP Endonuclease-Like Domain

A poly A element, L1Tc has been identified in *Trypanosoma cruzi* (Martin et al., 1995, *J Mol. Biol.* 247:49–59). This element encodes three ORFs: ORF1 resembles AP endonucleases. To determine whether this AP endonuclease homology is present in other poly A elements, the following experiments were performed.

Figure 7A:
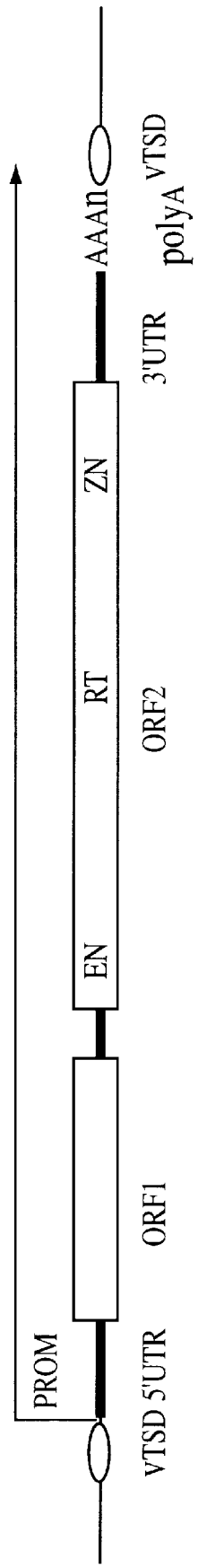
FIG. 7, comprising FIGS. 7A, 7Bi, and 7Bii, is a diagram depicting the sequence of various poly A elements and human AP endonuclease. The structure of the human L1 element is also shown wherein PROM denotes the L1 internal promoter; vTSD denotes the variable target site duplication; EN denotes the endonuclease domain; RT denotes the reverse transcriptase domain; and, ZN denotes the putative Zn-finger-like domain. The amino acid sequence alignment of poly A elements and human AP endonuclease are shown wherein the sequences are: TAD, from *Neurospora crassa*; L1Tc, from *T. cruzi*; R1Bm, from *B. mori*; FDM and GDM (F and G elements) from *D. melanogaster*; IDM (I-factor) from *D. Teissieri*; Jock,jockey from *D. melanogaster*; L1Hs, human L1; Tx1, from *Xenopus laevis*, Cin4, from *Zea mays*; and DRE, from *Dictyostelium discoideum*. APHs is the human AP endonuclease, DNase I from bovine pancreas. The EN domain was also identified in the following elements: CR1 (chicken), ingi (trypanosome), L1Md (mouse, and other mammalian L1s), Ta11 (Arabidopsis), TART (*D. melanogaster*), TRAS (*B. mori*), T1 (mosquito). Conserved (>2 identities) residues are shaded; residues conserved among all poly A elements and the human AP endonuclease are represented by a single circle; putative active site residues are indicated by a double circle. The numbers refer to the residues between two conserved blocks. Residues mutated in L1ENp are indicated by arrows and the names of each of the mutants are shown below each of the mutations. [SEQ ID NO:1–89, proceeding from left to right and top to bottom]

An amino acid sequence alignment of the AP endonuclease was generated using PILEUP (GCG,U. of Wisconsin) and was hand edited. Conserved residues and the putative catalytic active site residues were identified based on the structure of Exo III, the major AP endonuclease from *E. coli* (Mol et al., 1995, *Nature* 374:381–386). Next, an amino acid sequence alignment between an AP endonuclease and several poly A element ORFs was generated (FIG. 7). Several conserved AP endonuclease motifs were present in the poly A elements in the alignment. In particular, all conserved residues are equivalent to ExoIII residues in or near the active site (Mol. et al., supra). These motifs are only conserved in the non-sequence-specific poly A elements, but not in group II introns or LTR retrotransposons (Table 3) Spacing of the catalytic motifs was also conserved between the transposons and the AP endonucleases. This conserved domain of the poly A elements is hereinafter referred to as the "EN" domain.

TABLE 3

Many sequence-specific poly A elements lack the EN domain.

| ELEMENT | SPECIFIC FOR | ORFs | EN DOMAIN? |
|---|---|---|---|
| R2Bm | Sequence in rDNA array | 1 | – |
| CRE-1 | Sequence in mini-exon array | 1 | – |
| CRE-2 | Sequence in mini-exon array | 1 | – |
| SLACS | Sequence in mini-exon array | 1 | – |
| Group II intron | Intronless target site | 1 | – |
| R1Bm | Sequence in rDNA array | 2 | + |
| TART | Telomeres and heterochromatin | 2 | + |
| TRAS-1 | Telomeric repeat unit | 2 | + |
| DRE-1 | tRNA upstream regions | 2 | + |

The AP endonucleases are important enzymes having known roles in DNA repair in cells. They also exhibit 3' exonuclease, 3' phosphatase and RNaseH activities which are specified by a single site (Barzilay et al., 1995, *Nucl. Acids. Res.* 23:1544–1550; Weiss, 1976, *J. Biol. Chem.* 251:1896–1901). RNaseH or 3' to 5' exonuclease activities may play a role in retrotransposition. Several conserved AP endonuclease motifs are also shared with DNase, a non-specific nicking endonuclease, notably the proposed catalytic active site residues (FIG. 7). The overall fold in the DNaseI structure resembles ExoIII (Mol et al., 1995, supra), thus the EN domain may be a target site nickase.

EN Domain at L1 ORF2 N-terminus Encodes a Nicking Endonuclease

Figure 8A:
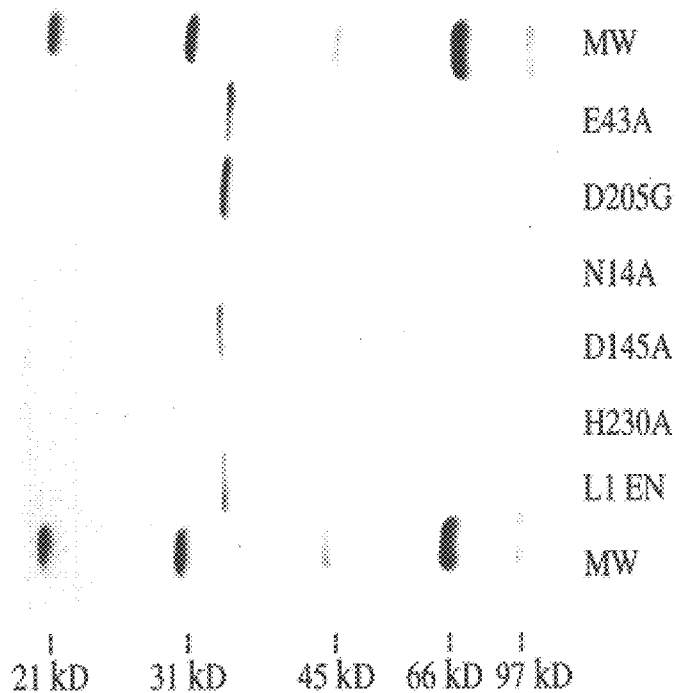
FIGS. 8A, 8B, and 8C, is an image of a series of gels depicting purification of and nicking activities of L1ENp and mutant proteins. In the gel depicted in FIG. 8A, purified proteins were separated on a 10% SDS-PAGE gel and were stained with Coomassie Blue. Approximately equal amounts of protein were loaded except in the case of H230A wherein 10-fold less protein was loaded. MW, molecular weight standards. In the gel depicted in FIG. 8B the nicking activities of the proteins were assessed. The lanes are numbered left to right and contain the following: 1) phage λ Hind III digest MW marker; 2) substrate pBS DNA, no protein added; 3) with 2.6 ng wild-type L1 ENp; 4) with 26 ng wild-type L1 ENp; 5) E43A mutant; 6) D205G; 7) N14A; 8) D145A; 9) H230A. The symbols used are as follows: sc is supercoiled plasmid; oc is open (nicked) circular plasmid; l is linear plasmid. In the gel depicted in FIG. 8C nicking was examined over time. Essentially, 50 fmol L1 ENp (or D205G mutant) was used to digest 500 fmol pBS and the extent of nicking was measured at the indicated times.

The EN domain at the L1 ORF2 N terminus identified above is highly conserved among poly A retrotransposons and resembles the apurinic/apyrimidinic (AP) endonucleases. The N-terminal 26 kD domain of L1 ORF2 (ending at residue 239) was expressed and purified to assess the functionality of the protein, referred to herein as L1 ENp. The protein was tagged with six histidine residues to facilitate purification thereof on Ni-agarose. A single protein band of 33 kDa of which 6 kDa comprise the histidine tag residues, was observed on SDS-PAGE (FIG. 8A, lane 7).

Figure 8B:
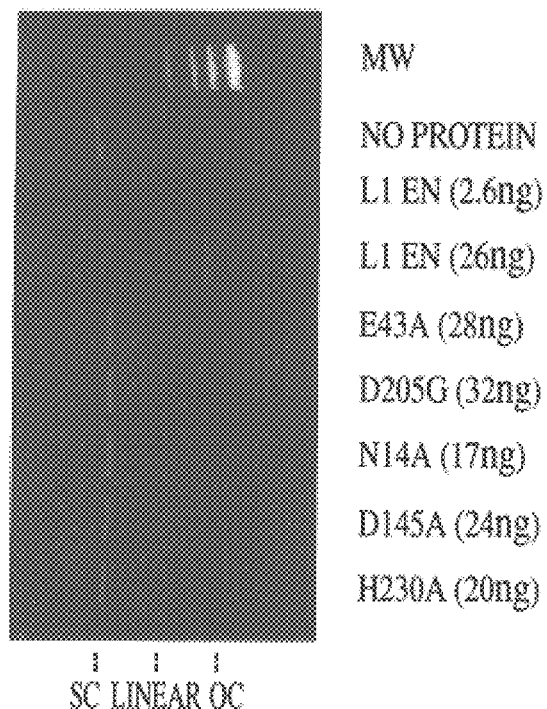
Figure 8C:
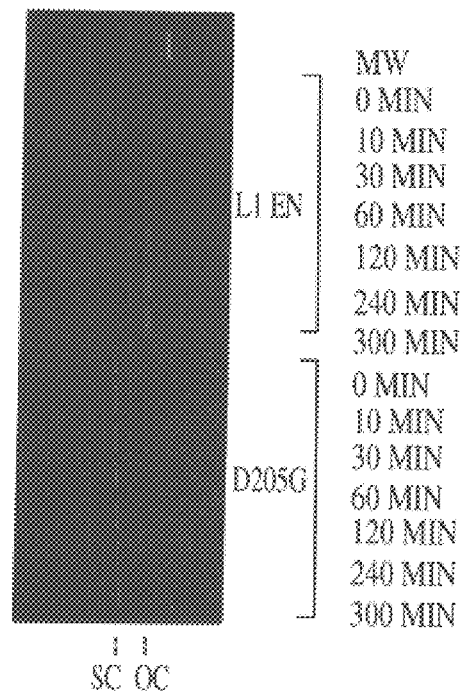

Endonuclease activity was assayed by measuring the ability of the protein to convert supercoiled plasmids into open circle DNA. L1 EN nicking activity depends on divalent cations, with Mg being greatly preferred over Mn. Thus, Mg was included in the assay. The nicking activity of this protein was further optimized with regard to buffer, pH and salt. It was found that when 2.6 ng (approximately 81 fmol) of purified L1 ENp was incubated with 0.2 μg supercoiled substrate DNA (approximately 100 fmol), 50% of the supercoiled DNA was converted to open circle DNA in 20 minutes (FIG. 8B, lane 3). When 26 ng L1 ENp was used, 100% of the supercoiled DNA was converted to a mixture of open circle DNA, as well as some linear plasmid DNA (FIG. 8B, lane 4).

The observed nicking activity was specific to the expression of L1 ENp since no activity was detected in preparations of mock-purified protein obtained from a vector containing strain. The specific activity of L1 ENp in the plasmid nicking assay is approximately 20,000-fold lower than that of DNase I on a molar basis. The calculated turnover number for L1 EN is approximately 2 phosphodiester bond cleavages per hour on a supercoiled pBS (Bluescript Ks, Stratagene, La Jolla, Calif.) substrate under optimal conditions. A time course experiment in which 1.7 ng (50 fmol) L1 EN digested 1 μg (500 fmol) DNA establishes that L1 ENp turns over and is therefore an enzyme.

Mutations in Conserved Residues of L1 EN Abolish Endonuclease Activity

Since many endonucleases are found in cell extracts, it was possible that the observed activity was derived from *E. coli* rather than the retrotransposon element. To establish that the endonuclease activity was encoded by the element, missense mutations were generated in the L1 ENp expression construct and the effect of the mutations on nicking activity was tested.

Certain residues are absolutely conserved among all poly A elements and AP endonucleases (FIG. 7). Three of these are believed to be especially critical for catalysis, including E43 (numbering refers to L1 ORF2), believed to bind the essential divalent cation and the D205 and H230 residues, believed to effect catalysis in both Exo III (Mol et al., 1995, *Nature* 374:381–386) and DNase I (Oefner et al., 1986, *J. Mol. Biol.* 192:605–632; Suck et al., 1988, *Nature* 332:464–468). Five conserved L1 residues including the above three were mutagenized. The five mutant proteins were tagged, expressed and purified in parallel with wild-type L1 ENp (FIG. 8A, lanes 2–6). All five mutants exhibit greatly reduced nicking activities relative to wild type L1 EN (FIG. 8B, lanes 5–9). The 43A mutant is slightly leaky (FIG. 8B, lane 5). Since this residue binds $Mg^{2+}$ in ExoIII (Mol et al., supra), human AP endonuclease (Barzilay et al., 1995, *Nature Structural Biol.* 2:61–568) and DNaseI (Oefner et al., supra; Suck et al., supra), the excess $Mg^{2+}$ provided in vitro may partially suppress this mutant. Nevertheless, the E43A mutant protein exhibited 20-fold less activity than wild type L1 ENp. Thus, L1 EN possesses nicking activity.

L1 ENp Leaves 5' $PO_4$ and 3' OH Residues

Figure 9:
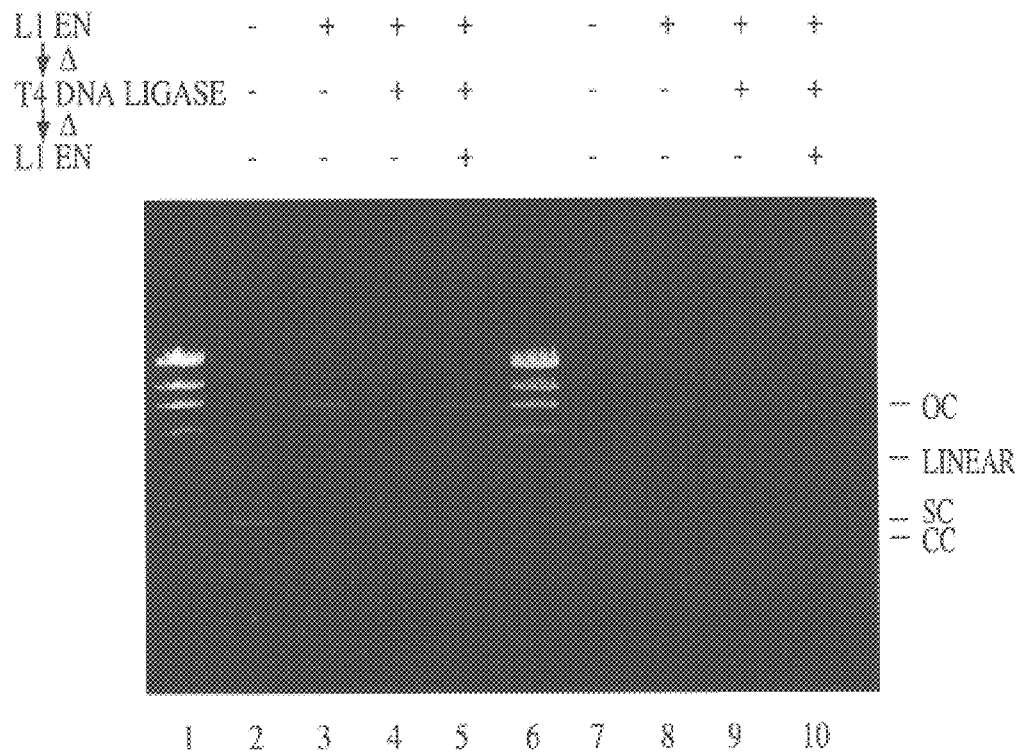
FIG. 9 is an image of a gel depicting the structure of the nicked DNA and preference of the enzyme for a supercoiled substrate. Supercoiled pBS DNA (0.2 μg) (lane 2) was incubated with L1 ENp to generate open circle DNA (lane 3). Subsequently L1 ENp was heat inactivated, and T4 DNA ligase was added (lane 4). After ligation, T4 DNA ligase was heat inactivated, and the product was again incubated with L1 ENp (lane 5). Lanes 7–10 are similar, except that 10-fold less L1 ENp was added initially. The symbol cc denotes closed relaxed circle DNA.

Nucleases can leave either 5'-$PO_4$/3'-OH or 5'-OH/3'-$PO_4$ termini. To examine the L1 ENp products, the ends made by L1 ENp were tested as substrates for T4 DNA ligase (Lehman, 1974, *Science* 186:790–797). Nicked circles generated by L1 ENp were incubated with T4 DNA ligase, and the ends were efficiently ligated (FIG. 9, lanes 2–5). Thus, L1 ENp, which generated 5'-$PO_4$/3'-OH termini, resembles class II AP endonucleases and DNase I, both of which leave 5'-$PO_4$. Further, the closed relaxed circle DNA product generated is itself a substrate for L1 EN (FIG. 9, lane 5). Thus L1 EN can cleave both supercoiled and relaxed DNAs.

L1 ENp is not Specific for AP DNA

Figure 10:
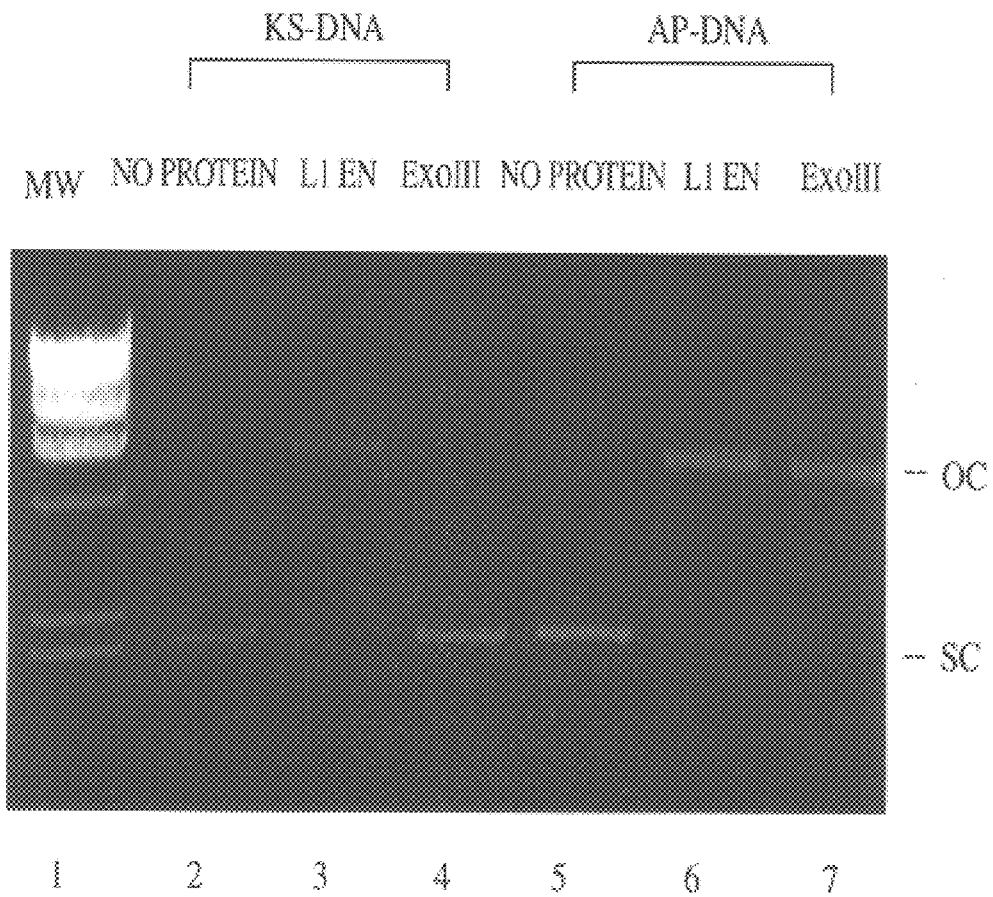
FIG. 10 is an image of a gel depicting the fact that L1 ENp cleaves native DNA and apurinic DNA equally well. The DNA substrate was either native DNA or apurinic DNA. KS-DNA, native pBS KS(−) DNA; AP-DNA, apurinic DNA; sc, supercoiled DNA; oc, open circle DNA, MW, λ HindIII digest.

Since L1 ENp cleaves native DNA (pBS plasmid DNA), and L1 ENp is closely related to AP endonucleases, experiments were performed to determine whether apurinic DNA was a preferred substrate for L1 ENp. Native pBS DNA and pBS containing 1–2 AP sites per plasmid (AP-DNA) were prepared. Native and AP-DNA were tested for cleavage by L1 ENp and Exo III. L1 ENp cleaved native DNA and AP-DNA equally (FIG. 10, lanes 3 and 6), whereas Exo III only cleaved AP-DNA (FIG. 10, lanes 4 and 7). Data obtained from titration experiments established that L1 ENp cleaved native and AP-DNA substrates with the same kinetics. Thus L1 ENp is not specific for AP-DNA.

L1 ENp Preferentially Cleaves Supercoiled DNA

Bacterial chromosomal DNA is supercoiled in vivo (Pettijohn et al., 1980, *Proc. Natl. Acad. Sci. U.S.A.* 77:1331–1335; Sinden et al., 1980, *Cell* 21:773–831), whereas virtually all supercoiling of eukaryotic DNA results from nucleosome wrapping (Sinden et al., 1981, *Proc. Natl. Acad. Sci. U.S.A.* 78:224–228). However, chromosomal DNA targets in eukaryotic cells are likely to be supercoiled transiently as the result of moving polymerases, and transient nucleosome removal (Drolet et al., 1994, *J Biol. Chem.* 269:2068–2074; Liu et al., 1987, *Proc. Natl. Acad. Sci. U.S.A.* 84:7024–27; Tsao et al., 1989, *Cell* 56:111–8). To determine whether supercoiled or closed relaxed circle DNAs were preferred targets for L1 ENp in vitro, the ligation experiments were repeated with a limiting amount of L1 ENp (FIG. 9, lanes 7–10) such that about half the supercoiled DNA was converted into open circle DNA (FIG. 9, lane 8). This material was then converted into closed relaxed circle DNA by treatment with T4 DNA ligase (FIG. 9, lane 9), generating an approximately 60/40 mixture of supercoiled and closed relaxed circle substrates. L1 ENp preferred the supercoiled DNA substrate (FIG. 9, lane 10).

Supercoiled pBS DNA has Cleavage Hot Spots for L1 ENp

Figure 11A:
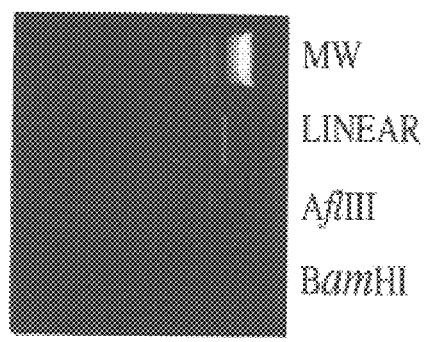

The ease with linear DNA was generated by L1 ENp cleavage suggests that L1 ENp cleavage is not random. L1 ENp double strand breaks presumable result from closely spaced nicks on opposite strands. To determine whether breaks generated by L1 ENp were randomly distributed, supercoiled pBS DNA was linearized with L1 ENp, and the linear DNAs were digested with seven different restriction enzymes which restrict the plasmid at either one or two sites. Discrete bands (2 or 3 bands, respectively) were observed instead of smears (FIG. 11A) and thus, linearization by L1 ENp occurs at a specific site in pBS DNA. The position of the preferred double-strand break made by L1 ENp was mapped to about position 1900 in pBS.

Figure 11D:
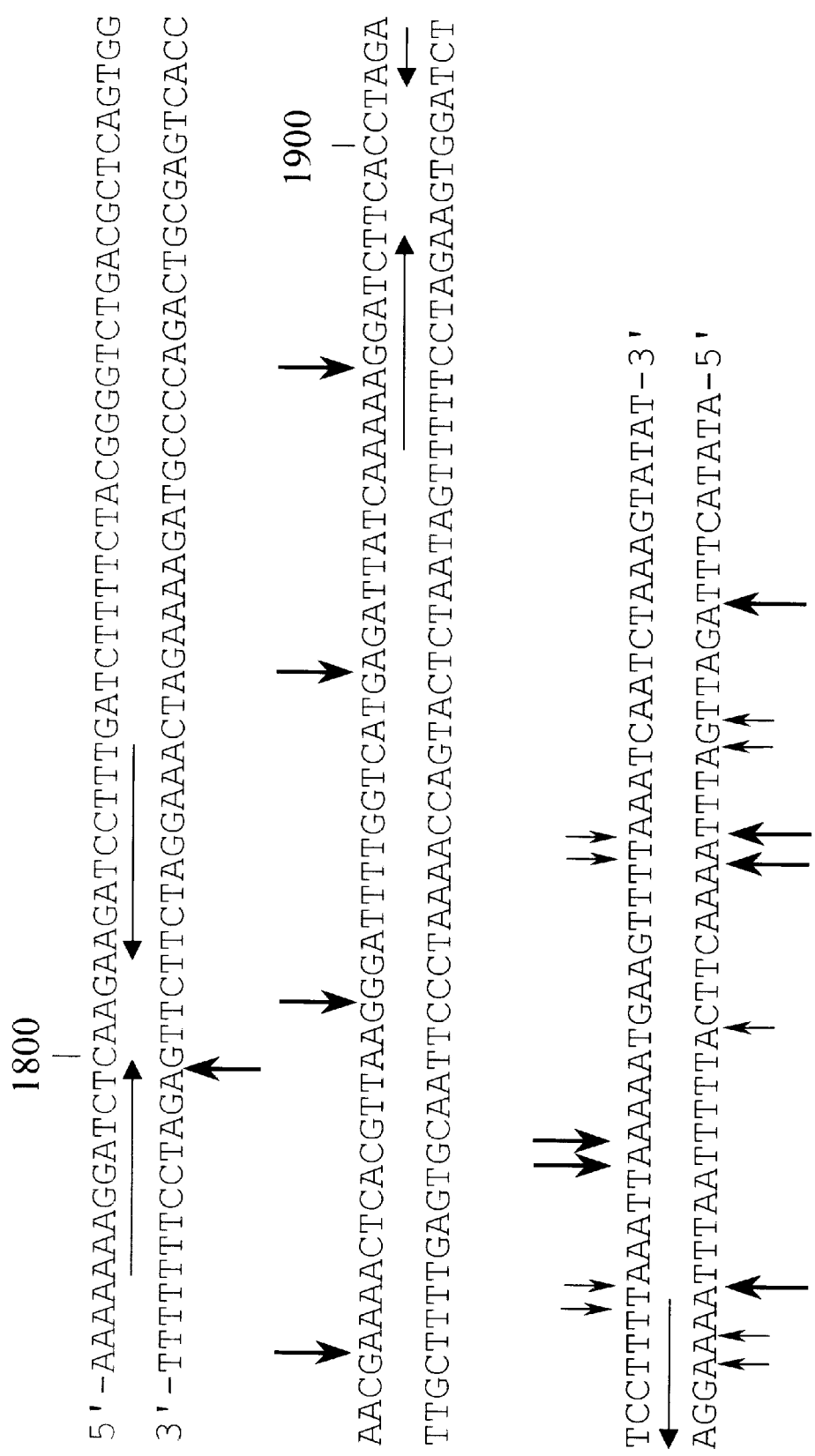

Primer extension was used to precisely define L1 ENp cleavage sites on each strand. Using $^{32}$P-labeled oligonucleotide primers flanking this region, the ends of linear pBS DNA generated by L1 ENp were mapped. Six major cleavage sites were mapped on each strand within this region (FIG. 11D). All major sites identified had a purine immediately 3' to the point of cleavage, usually an A, and most sites had several purines in a row. In addition, about half the sites had a run of pyrimidine residues just 5' to the point of cleavage, suggesting a consensus sequence of (Py)n↓(Pu)n for L1 ENp cleavage. All of the L1 ENp cleavages observed reside in a very A T-rich segment of pBS DNA. These regions are referred to herein as "hotspots" for L1 ENp cleavage.

Since a cluster of cleavage hots spots were mapped to this region, the kinetics of this cleavage were also examined. L1 ENp cleavage was titrated and ranged from approximately 40% conversion to open circles, to 90% conversion to open circles and 10% conversion to linears (FIG. 11B). Primer extension was performed on these DNAs with primers flanking the site (FIG. 11C, JB1132 and JB1133) and a control T7 primer. One highly preferred site on the arbitrarily defined "top" strand was cleaved first; and overall, sites on this strand were cleaved faster than bottom strand sites. Using the T7 primer, little cleavage was observed. Thus, cleavage of pBS DNA by L1 ENp is not random.

Cleavage Specificity of the L1 ENp is not Affected by Supercoiling

Experiments were performed to determine whether supercoiling was necessary for specific recognition and cleavage of hotspot sites, or whether it only affected cleavage rate. This determination aids in defining the enzyme specificity because it addresses whether specificity is intrinsic to DNA sequence or whether a higher order structure (such as a cruciform) is required. pBS DNA was nicked with HpaII in the presence of ethidium bromide and the DNA was ligated to form relaxed closed circular substrates. Four times more L1 ENp had to be added to the relaxed substrate as to supercoiled plasmid to achieve a similar extent of cleavage. However, the specificity of cleavage of supercoiled and relaxed DNAs was identical (FIG. 12).

L1 ENp Cleavage of Other Targets

Figure 13:
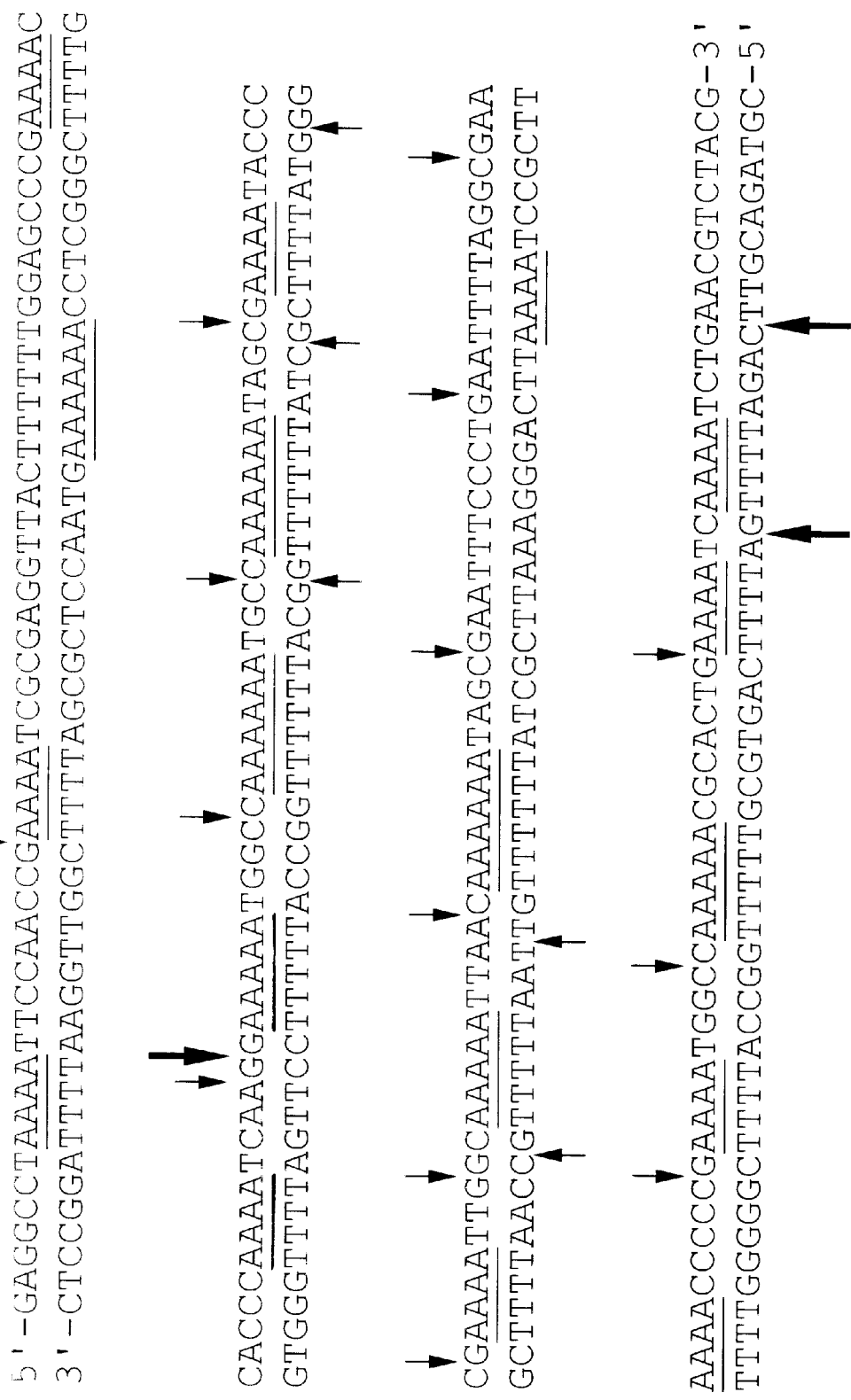
FIG. 13 is a sequence diagram depicting the fact that K-DNA contains a hotspot for L1 ENp cleavage (indicated by bold arrow) [SEQ ID NO:91]. The cleavage sites were determined as described in FIG. 11 except that the SP6 primer was used. Sites of enhanced cleavage by hydroxyl radical were determined using the method of Burkhoff et al. (1987, *Cell* 48:935–943) and are indicated by small vertical arrows. Bold letters indicate phased A-tracts.

Cruciform and bent DNAs were tested to determine which were preferred substrates for L1 ENp cleavage. Cruciform sequences tested included endogenous cruciforms mapping within the pBS hotspot region (Lilley, 1981, *Nucl. Acids Res.* 9:1271–1288). Cruciform sequences and their boundaries with normal DNA occasionally contained sites of preferred cleavage, but usually did not. In particular, the "major" pBR322 cruciform (Lilley, supra) lacked such sites. The bent DNA tested was from K-DNA, which contains a severely bent fragment (Kitchin et al., 1986, J. Biol. Chem. 261:11302–11309). Primer extension mapping of the preferred site(s) of nicking was performed using plasmid pPK201/CAT, which consists of the K-DNA fragment cloned into a pSP65 vector (Promega, Madison, Wis.), which contains the same hotspot region found in pBS. Two approximately equally utilized hotspots for double-strand cleavage were observed in pPK201/CAT. One of these was the previously mapped hotspot, the other was in a subset of the oligo A tracts of the K-DNA (FIG. 13). However, not all bent segments in the K-DNA were nicked. Thus it appears that certain, but not all, regions of bent DNA are hotspots for L1 ENp cleavage.

L1 in vivo Target Sites Resemble L1 ENp Cleavage Sites

Figure 14A:
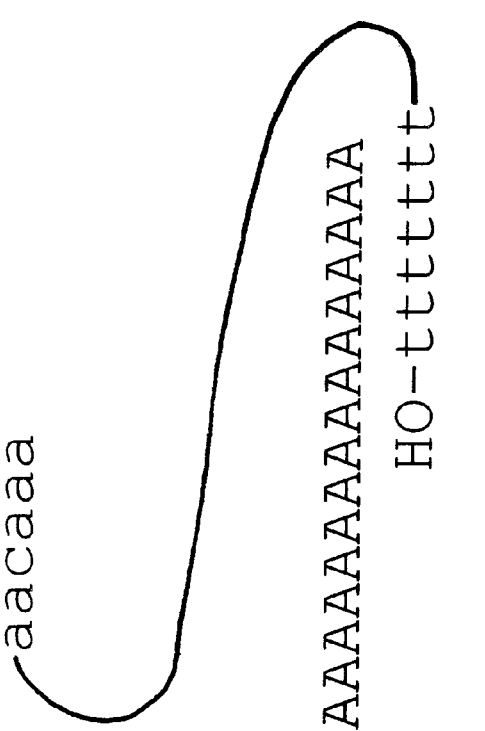

The sequences of new human mutations caused by L1 insertion were examined. In addition, the terminal sequences of full-length L1s, including several elements known to be active in transposition were examined. From the TSDs, the site of priming of minus strand reverse transcription was inferred, assuming that the reverse transcription of L1 3' end RNA had been primed by chromosomal nicks. Further, a number of TSD sequences from truncated human L1 element sequences present in GenBank were collected. These sequences indicate that like L1 ENp, the activity that cleaves the target for L1 insertion has one or more purines just 3' to the site of cleavage, and these often involve short runs of A's. These are usually symmetrically juxtaposed to a run of pyrimidines 5' to the site of cleavage (FIG. 14). All the sequences are very A-T-rich; this specificity is completely consistent with that observed for L1 ENp in vitro.

Mutations in L1 EN Domain Kill L1 Retrotransposition

Figure 15A:
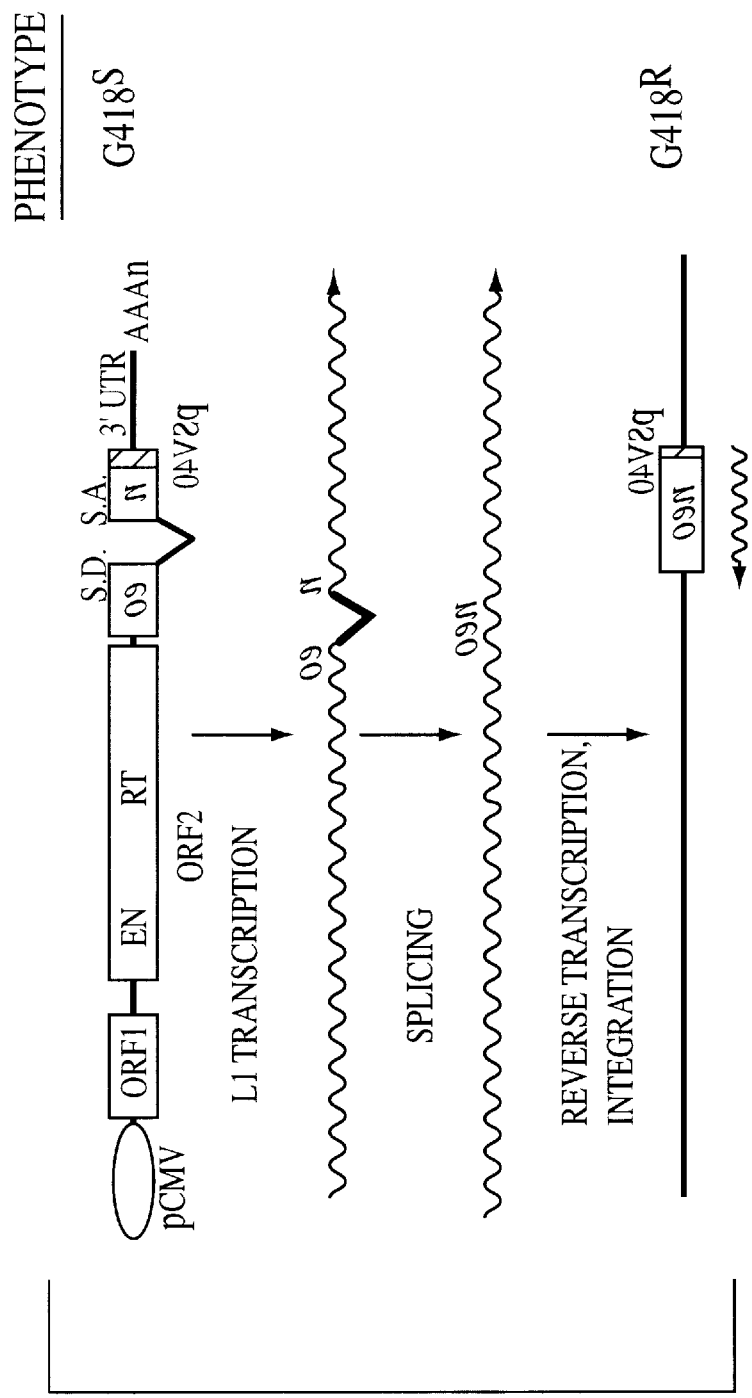

The transposition-competent L1 bearing a genetic marker (L1.2 mneoI) described herein was used to evaluate the importance of the EN domain in retrotransposition. As described herein, the construct consists of a functional L1 element, L1.2A, driven by the CMV early promoter/enhancer. The element is marked with the mneoI gene, driven by the SV40 early promoter and inserted downstream of L1 ORF2, within the L1 3' UTR and in the opposite transcriptional orientation relative to L1. The marker gene is also disrupted with an intron oriented such that it can only be spliced out of L1 RNA. G418-resistant cells arise only when the L1.2 mneoI retrotransposes, resulting in generation of a functional neo gene. The number of G418-resistant colonies gives a readout of transposition frequency. The wild-type L1-neo-I element gave rise to G418-resistant colonies at a frequency of $3.4 \times 10^{-4}$ per cell, but a control mutation in the L1 ORF2 RT domain (D702Y) reduced transposition frequency about 600-fold. Four conserved residue mutations in the L1 EN domain similarly reduced the G418-resistant colonies about 100- to 500-fold (FIG. 15) as do two additional mutations. These data demonstrate that the L1 EN domain is essential for L1 retrotransposition.

EXAMPLE 3

Characterization of Five Novel Active L1 Elements: An estimate of the Number of Active L1 Elements in the Human Genome.

It has been discovered in the present invention, and is exemplified in Example 3, that the human genome comprises a number of active L1 elements which are useful in the methods of the present invention. The data presented in Example 3 may be summarized as follows.

Using a selective screening strategy to enrich for active L1 elements, thirteen full-length elements have been isolated from a human genomic library. These elements were tested, in addition to the two previously isolated L1s, L1.3 and L1.4, for RT activity and for the ability to retrotranspose in HeLa cells. Of the thirteen newly isolated L1s, eight possess RT activity and three are capable of retrotransposition. L1.3 and L1.4 possessed RT activity and retrotranspose at remarkably high frequencies. These studies bring the number of characterized active human L1 elements to seven. Based on these and other data, it is estimated that 30–60 active L1 elements reside in the average diploid human genome.

The materials and methods used in Example 3 are now described.

Yeast Strains and Media

Experiments were performed in yeast strain AGY9 (MATα ura3-52 trp1Δ63 leu2Δl his4-539 lys2-801 spt3-101) unless otherwise indicated (Mathias et al., 1991, *Science* 254,1808–1810). The strain yDS50.1 was created by introducing plasmid pSM50 into strain YH50 (Matα his3Δ200 ura3-167 trp1Δ1 leu2Δ1 spt3-202) (Dombroski et al., 1994, *Mol. Cell. Biol.* 14:4485–92). Transformants were selected on SC -Trp medium. Yeast transformation and all media were prepared using standard protocols (Rose et al., 1990, *Methods in Yeast Genetics: A Laboratory Course Manual,* Cold Spring Harbor, N.Y.).

Library Screening and Phage Isolation

Figure 16:
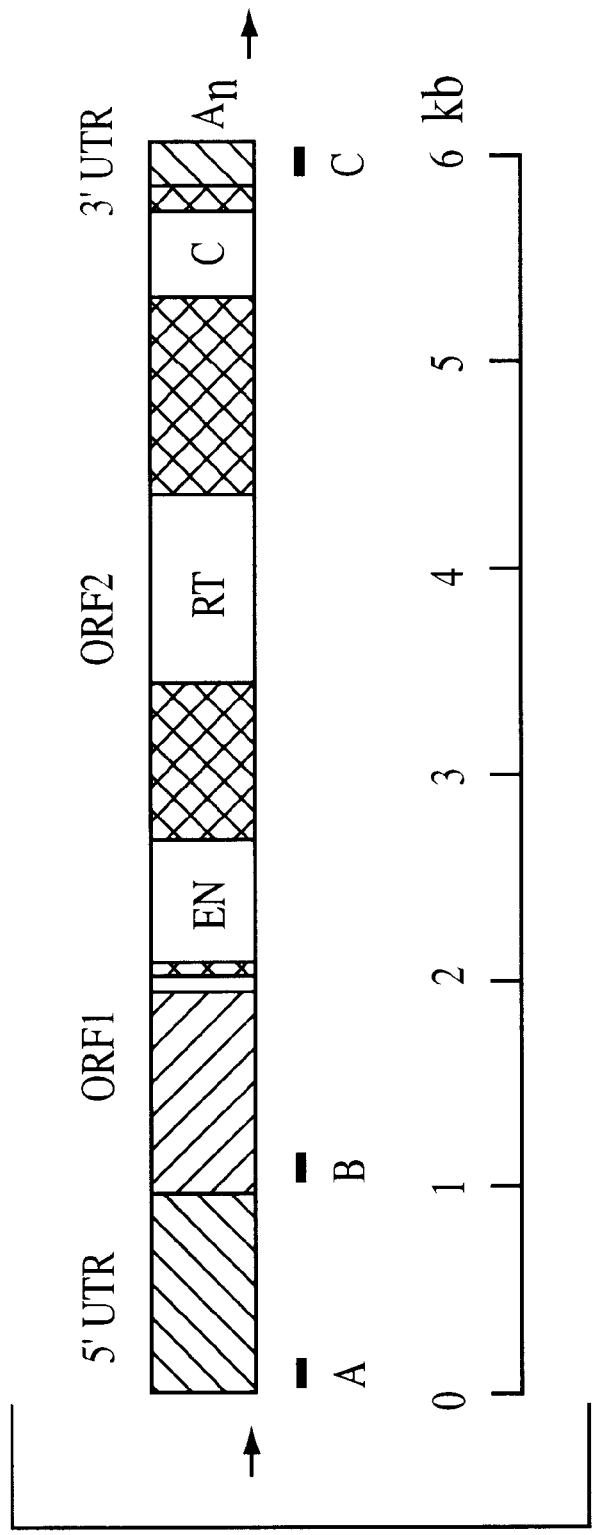
FIG. 16 is a diagram depicting the organization of a human L1 element and the location of oligomers A, B and C. ORF1 and ORF2 are indicated by a downwardly-hatched box and dark gray box, respectively. The 5' and 3' untranslated regions (UTRs) are indicated by upwardly-hatched boxes and the poly A tail by $A_n$. The approximate positions of the endonuclease (EN), reverse transcriptase (RT) and cysteine-rich motifs in ORF2 are indicated. Oligomer A is located at nucleotides 61–80, oligomer B at nucleotides 941–960, and oligomer C at nucleotides 5919–5938 of the L1.2 sequence (Dombroski, et al., 1991, *Science* 254:1805–1808).

Approximately $2 \times 10^6$ plaques were screened from a previously described human genomic DNA library in λ phage (Dombroski et al., 1991, *Science* 254:1805–1808) with the three oligomers listed in FIG. 16. Secondary and tertiary screens were used to purify positive clones to homogeneity (Sambrook et al., 1989, *Molecular Cloning: A Laboratory Manual,* Cold Spring Harbor, N.Y.).

Plasmid DNA preparation and sequencing

Phage λ DNA was prepared using a Qiagen λ kit. Plasmid DNAs were purified on Qiagen maxi or midi prep columns. DNAs for transfection experiments were checked for superhelicity by electrophoresis on 0.7% agarose-ethidium bromide gels and only highly supercoiled preparations (>90%) were used in transfection experiments. DNA sequencing was done on an Applied Biosystems DNA sequencer (ABI377).

Plasmids used in this study

A 5.9 kb AccI restriction fragment was gel purified from λ phage spanning bases 39 to 5964 in L1.2 (Dombroski et al., 1991, *Science* 254:1805–1808) from each of the thirteen newly isolated L1s, and L1.3 and L1.4 using the Gene Clean protocol (Bio 101 Inc.). The polylinker of pBluescript (Stratagene) was engineered to contain two AccI sites identical to those present in the 5' and 3' UTR of each L1 element. Each AccI fragment was subcloned into the modified pBluescript to create plasmids L1.X. The X indicates each different L1 element tested (e.g. L1.3, L1.4, L1.20).

For expression constructs used in the biochemical assay, site-directed mutagenesis (Kunkel et al., 1991, *Methods in Enzymology* 204:125–139) was used to destroy the BglII site present at nucleotide 2217 in TyB of pSM2 (Mathias et al., 1991, *Science* 254, 1808–1810). The resulting Ty1/L1 ORF2 expression plasmid (pSM2B) contained a unique BglII site near the beginning of L1 ORF2 (nt 2172 of L1.2). Next, the 3.8 kb BglII-SacI fragment (from nt 2172 of L1.2 to polylinker sequence located 3' of the element) in pSM2B was replaced with the corresponding 3.8 kb fragment from each of the pL1.X constructs to create plasmids pSM2B-L1.X. Note, each pSM2B-L1.X construct retains the first 182 nts of L1.2 ORF2.

For expression constructs used in the HIS3 pseudogene assay, an epitope tag was first introduced at the extreme N-terminus of L1.2 ORF2 in plasmid pSM42 (Dombroski et al., 1994, *Mol. Cell. Biol.* 14:4485–4492) to create pSM42 et. PCR amplification was used to isolate a DNA fragment from plasmid pSM2et (Mathias et al., 1991, *Science* 254:1808–1810 which contained the hemagglutinin tag, 12CA5, as well as flanking TyB and L1 sequences. The epitope-tag containing fragment was introduced into pSM42 by yeast recombination cloning. The epitope tag fragment was purified and 1.0 μg was transformed into the yeast strain yDS50.1 along with 1.0 μg of pSM42 which had been linearized at the SalI site that demarks the TyB/L1 ORF2 junction. Yeast transformants were isolated on SC-trp medium and the recombinant plasmids were recovered as previously described (Ward et al., 1990, *Nucl. Acids Res.* 18:5319). The presence of the epitope tag was confirmed by screening. The 3.8 kb BglII-SacI restriction fragment (see above) from pSM42et was then replaced with the corresponding fragment from pSM42-L1.X (Sassaman, 1996, *Characterization of five novel human L1 elements capable of retrotransposition,* Doctoral Dissertation, Johns Hopkins University, Baltimore, Md.) to create plasmids pSM42et-L1.X.

For expression constructs used in the HeLa cell retrotransposition assay, the 5.9 kb AccI restriction fragment from pJCC9 (nts 39 to 5964 of L1.2) described herein, was replaced with the corresponding fragment from each of the L1s tested, creating plasmids pneo-L1.X. The 8.1 kb NotI-ClaI fragment from each pneo-L1.X construct was then subcloned between the unique NotI and BamHI restriction sites in pCEP4 (In Vitrogen) to create pCEP4-L1.X. Note, that the ClaI and BamHI sites were blunt-ended prior to restriction with NotI. As such, the substrates in these ligations contained one blunt end and one end with a 5' overhang.

Isolation of Virus-Like Particles

Virus like particles (VLPs) were isolated using a protocol modified from Mathias et al. (Mathias et al., 1991, *Science* 254:1808–1810). Transformed AGY9 strains at a starting $OD_{600}$ of 0.3 were grown in 100 ml of YNB-trp containing 0.1% glucose at 30° C. for 24 hours. The cultures were added to 400 ml YNB-trp media containing 2% galactose and grown at 22° C. for 24 hours. Cells were pelleted at 5,000 rpm for 10 minutes in a Sorvall GSA rotor, washed once with $H_2O$, and resuspended in 5 ml ice-cold Buffer B/EDTA (15 mM KCl, 10 mM HEPES pH 7.8, 5 mM EDTA) containing 3 mM dithiothreitol, 2 mM phenylmethyl-sulfonyl fluoride (PMSF), and one Protease Inhibitor Cocktail Tablet (Boehringer Mannheim) per 50 ml of buffer. All subsequent steps were performed at 4° C. Yeast cells were broken by vortexing in the presence of glass beads (Sigma) for 5 minutes. That procedure was repeated 5 times with a 2 minute rest between breaking cycles. The initial extract and two 2 ml washes were combined and centrifuged for 10 minutes at 10,000 rpm in a Sorvall SS-34 rotor. The supernatant was layered on top of a 20%–70% linear sucrose gradient made in Buffer B/EDTA and was centrifuged in a Beckman SW28 rotor at 25,000 rpm for 16 hours at 4° C. VLPs were collected from the gradient using a BioComp Gradient Fractionator, diluted with 25 ml Buffer B/EDTA containing 3 mM DTT and one Protease Inhibitor Cocktail Tablet per 50 ml of extract. The mixture was centrifuged at 25,000 rpm for 2 hours at 4° C. and the pellet was resuspended in 100 µl Buffer B/EDTA, aliquoted, and stored at −80° C.

Reverse Transcriptase Assays

Protein concentrations of the VLP preparations were determined using the Bio-Rad Protein Assay (Bio-Rad). Unless otherwise indicated, 1 µg of total protein was added to 25 µl of standard reaction mix which contained: 10 µg/ml poly(rC), 0.7 µg/ml oligo(dG)12–18, 180 mM dGTP (Pharmacia), 10 mM $MgCl_2$, 50 mM Tris-HCl, pH 8.0, 2% β-mercaptoethanol and 60 µCi/ml α-$^{32}$P-dGTP (NEN Research Products). The reactions were incubated at 30° C. for one hour and 15 µl of each was spotted onto DE81 paper (Whatman) and air dried. The dried filters were washed with 2× SSC (three times for 20 minutes), rinsed with 95% ethanol, and air dried. Incorporation of radiolabeled nucleotides was determined by scintillation counting of the washed aliquots (Goff et al., 1981, *J. Virol.* 38:239–248) and the results are reported as femtomoles dGTP incorporated.

The HIS3 pseudogene assay

The HIS3 pseudogene assay was performed essentially as described (Dombroski et al., 1994, *Mol. Cell. Biol.* 14:4485–4492). AG9 transformed with the Ty1/L1 ORF2 expression constructs (pSM42-L1.X) and the indicator cassette (pSM50) were isolated on SC-Ura-Trp medium. The transformants were subcloned and four to six independent colonies were grown as patches on SC-Ura-Trp medium for three days at 30° C. To induce expression of the Ty/L1 constructs, the patches were replica plated to two different SC-Ura-Trp plates containing 2% galactose and incubated for five days at 22° C. After induction, one plate was replica plated to SC-His medium to provide a qualitative readout of RT activity. Patches from the other plate were diluted in $H_2O$, plated onto SC-His and YpD medium, and grown for four days at 30° C. The relative RT activity was reported as the number of His+ colonies/ number of colonies plated.

Retrotransposition assay

The HeLa cell retrotransposition assay was performed as described herein. HeLa cells were grown at 37° C. in an atmosphere containing 7% $CO_2$ in Dulbecco's modified Eagle's medium (DMEM) lacking pyruvate. DMEM was supplemented with 10% fetal bovine calf serum (FCS), 0.4 mM glutamine, and 20 U/ml penicillin-streptomycin. Cells were passaged by standard methods.

Somatic cell hybrid panel mapping

PCR reactions were performed on 50–100 ng of DNA from each somatic cell hybrid (Corriell Cell Repository). Generally, 30 µl reactions containing 10 mM Tris-HCl pH 8.3, 50 mM KCl, 1.5 mM $MgCl_2$, 0.2 mM DNTP, 1 unit AmpliTaq DNA polymerase (Perkin-Elmer), and 60 ng of each primer were amplified for 25–30 cycles. Denaturation, annealing, and extension steps were for 30 seconds each. In general annealing was carried out at 5° C. below the Tm of the primers. PCR products were separated on 1% agarose (Gibco-BRL), 1.5% Nusieve (FMC) gels and visualized by staining with ethidium bromide.

Determination of gene frequencies of active L1s

Southern blot analysis was carried out on the DNAs of 19–25 different individuals using probes flanking each of the newly-isolated active L1s. The 5' flank of each L1 was checked for repetitive sequences by use of the BLAST (Altschul et al., 1990, *J Mol. Biol.* 215:403–410) algorithm (BCM search launcher). Single copy probes were generated by PCR and ranged from 300–600 bp.

The results of the experiments presented in Example 3 are now described.

Isolation and chromosomal localization of potentially-active L1 elements

The vast majority of full-length L1s in the human genome are non-functional. A strategy has been developed herein to enrich for active L1s by screening a partial BamHI human genomic library in bacteriophage λ using three specific oligomers as probes (FIG. 16). Oligomer A contains a sequence from the 5' end of L1 to ensure that the selected L1s were full length; oligomer B contains a sequence in ORF1 that is a feature of expressed L1s (Skowronski et al., 1988, *Mol. Cell. Biol.* 8:1385–1397; Dombroski et al., 1991, *Science* 254:1805–1808), and oligomer C contains a sequence specific for the Ta subset (Skowronski et al., 1988, *Mol. Cell. Biol.* 8:1385–1397).

Of $2 \times 10^6$ plaques screened, thirty independent positive clones were isolated and purified. DNA sequence flanking these L1s revealed that seventeen of the thirty were unique. Eight elements were recovered more than once, indicating that the screening method was reproducible. Studies on thirteen of these seventeen new elements and L1.3 and L1.4 are now described.

L1s are dispersed throughout the human genome having no particular chromosomal preference (Hutchison et al., 1989, LINES and related retrotransposons: long interspersed sequences in the eukaryotic genome in Mobile DNA eds., Berg et al., pp.593–617, ASM Press, Washington, D.C.). To discover whether the novel elements were distributed on different chromosomes, the chromosomal location of each was mapped using a panel of human/rodent somatic cell hybrid DNAs. For each L1, a single PCR product of the predicted size was observed in only one of the hybrid DNAs (Sassaman, 1996, *Characterization of five novel human L1 elements capable of retrotransposition*, Doctoral Dissertation, Johns Hopkins University, Baltimore, Md.). The results obtained demonstrate that the thirteen elements reside on various chromosomes (Table 4).

Table 4: Summary of L1s tested.

Results of functional assays, state (open or closed) of each reading frame, and the chromosomal location of each element are presented. Chromosomal locations of L1.2 (Dombroski et al., 1991, *Science* 254:1805–1808), L1.3, L1.4 (Dombroski et al., 1993, *Proc. Natl. Acad. Sci. U.S.A.* 90:6513–6517) and LRE2 (Holmes et al., 1994, *Nature Genetics* 7:143–48) and the retrotransposition rates of LRE2 are previously reported herein, but are included in Table 4 for completeness. Results of the biochemical RT assay (column 2) are reported as fmoles of $\alpha^{32}$P-dGTP incorporated into a polyrC/oligodG template. Results of the HIS3 pseudogene assay (column 3) are reported as the number of histidine prototrophs divided by the total number of colonies plated. Results of the retrotransposition assay (column 4) are reported as the number of G418$^R$ foci divided by the number of hygromycin-resistant cells plated. The retrotransposition frequency for each element was determined in triplicate for at least two independent experiments. In column 5 open means that the reading frame of ORF1 lacks stop codons and can encode the predicted 338 amino acid protein. For prematurely truncated mutants, the amino acid position of the stop codon (X) is noted. In column 6 open means that the reading frame of ORF2 lacks stop codons and can encode the predicted 1245 amino acid protein. For prematurely truncated mutants the nt position of the frameshift (FS) mutation or stop codon (X) is noted. Column 7 indicates the chromosomal position of each of the L1 elements tested. N.D.=not done. [a] A frameshift located at the extreme 5' end of ORF2 closes this reading frame in the natural element, however, this region of L1.5 was not included in the test construct. With respect to the RT assays performed, the L11.5 reading frame was open. [b] A nonsense codon truncates the reading frame by 51 amino acids.

that over half of the newly-isolated elements contained intact ORFs demonstrates the power of our screening procedure in identifying potentially-active L1s.

Many novel L1s encode reverse transcriptase activity

Figure 17A:
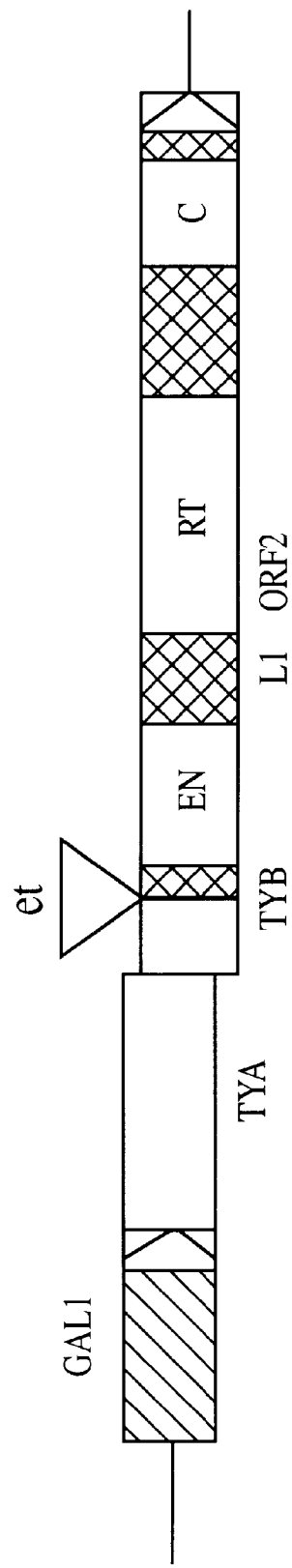
FIG. 17A is a diagram depicting the Ty1-based construct used to express the L1 RT in the biochemical assay shown in FIG. 17B. Ty1 contains two ORFs. The first, TyA, encodes a Gag-like protein. The second TyB, is expressed as a fusion protein that is post-translationally processed to generate proteins with protease, integrase, RT, and RNase H activity. When Ty1 is experimentally expressed from a promoter inducible by galactose (GAL1), the Ty1-encoded proteins and RNA co-assemble into cytoplasmic virus-like particles (VLPs) which can be partially purified and assayed for Ty1 RT activity (Garfinkel et al., 1985, Cell 42: 507–517). The integrase, RT and RNase H domains of TyB are replaced by L1 ORF2. The hemagglutinin epitope tag 12CA5 (et) was inserted at the Ty1/L1 ORF2 junction. Boxes with non-filled triangles are long terminal repeats (LTRs). Expression from the inducible GAL1 promoter results in virus-like particles (VLPs) that contain RT.

The thirteen new elements, L1.3, and L1.4 were next tested for RT activity using two previously-established assays based on the yeast retrotransposon, Ty1(Mathias et al., 1991, *Science* 254:1808–1810; Boeke et al., 1985, *Cell* 40:491–500). In the first assay, the integrase, RT, and RNASE H domains of TyB, the second ORF of Ty1, were replaced with the entire ORF2 of each element (See legend to FIG. 17A for a description of the assay). To detect the hybrid Ty1/L1 ORF2 proteins, a hemagglutinin (HA) epitope tag 12CA5 (et) was fused to the N-terminus of the ORF2 protein. The hybrid Ty1/L1 ORF2 constructs were placed under the control of the GAL1 promoter. After induction in medium containing galactose, VPLs were partially purified and tested for their RT activity.

Figure 17B:
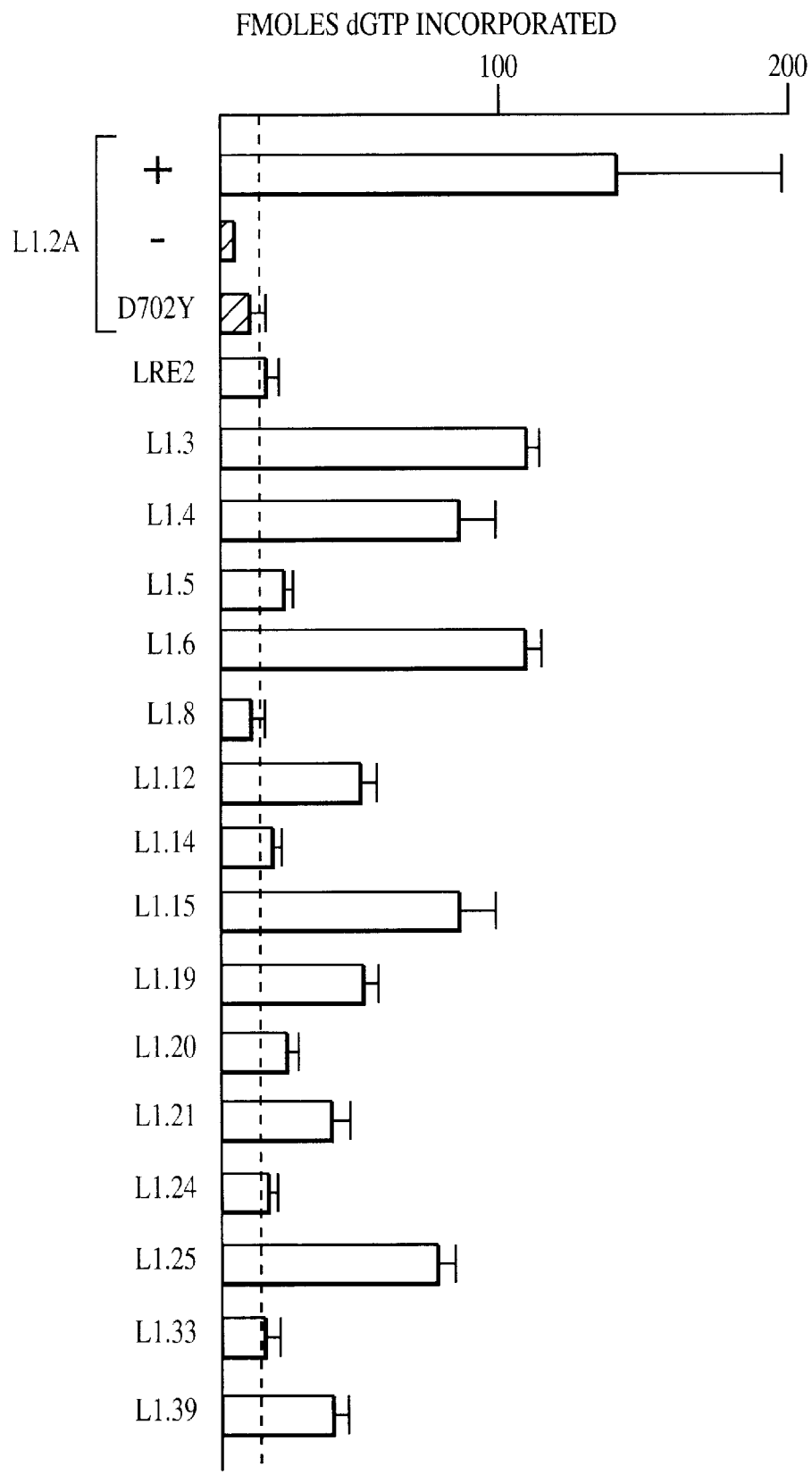
FIG. 17B is a graph depicting the RT activity of thirteen novel L1 elements and L1.3, L1.4, and LRE2. One μg of total VLP extract in a 30 μl reaction volume was assayed as described in the materials and methods section of Example 3. Relative RT activity is reported as fmoles of $\alpha^{32}$P-dGTP incorporated into a polyrC/oligodG template. Values are the averages of 5–8 independent assays of two separate VLP preparations and the error bars are shown. RT activity a levels significantly greater than that observed for the D702Y mutant was observed in the case of L1.3, L1.4, L1.6, L1.12, L1.15, L1.19, L1.21, L1.25, and L1.33.

Seven of the thirteen new elements, as well as L1.3 and L1.4, exhibited RT activity significantly greater than an RT-defective mutant D702Y (FIG. 17B). Extracts were subjected to Western blot analysis using an anti-TyA antibody (Braiterman, et al., 1994, *Gene* 139:19–26). It was found that VLPs were uniformly produced in all of these strains. An assay was conducted to detect Ty1/L1 ORF2

TABLE 4

COMPILED DATA ON THE L1 ELEMENTS STUDIED

| L1 | RT (fmoles) | RT (× 10$^{-7}$) | Rtpn (× 10$^{-6}$) | ORF1 | ORF2 | CHROM. |
|---|---|---|---|---|---|---|
| L1.2A | 140 +/− 53 | 1045 | 830 | open | open | 22 |
| D702Y | 12 +/− 5 | 0.1 | 2.7 | | | |
| LRE2 | 18 +/− 3 | 3.8 | 1140 | open | open | 1 |
| L1.3 | 105 +/− 32 | 575 | 6900 | open | open | 14 |
| L1.4 | 86 +/− 15 | 2114 | 4200 | open | open | 9 |
| L1.5 | 22 +/− 2 | 0.1 | N.D. | R49X | FS1998[a] | 11 |
| L1.6 | 107 +/− 8 | 776 | <1 | R130X | open | X |
| L1.8 | 12 +/− 5 | 0.1 | 13 | open | open | 14 |
| L1.12 | 47 +/− 6 | 2.8 | <1 | R130X | open | 18 |
| L1.14 | 18 +/− 3 | 0 | <1 | open | W1233x[b] | X |
| L1.15 | 84 +/− 13 | 748 | <1 | open | open | 5 |
| L1.19 | 49 +/− 5 | 781 | 720 | open | open | 7 |
| L1.20 | 22 +/− 4 | 60 | 1200 | open | open | 20 |
| L1.21 | 38 +/− 7 | 0 | <1 | open | open | N.D. |
| L1.24 | 16 +/− 2 | 0.5 | N.D. | open | FS2972 | 12 |
| L1.25 | 77 +/− 8 | 49 | <1 | open | open | N.D. |
| L1.33 | 15 +/− 3 | 0.5 | N.D. | open | FS2572 | 20 |
| L1.39 | 39 +/− 5 | 365 | 57 | open | open | 14 |

Sequence analysis of novel L1 elements

Each of the thirteen newly-isolated elements was sequenced in its entirety. Although randomly isolated human L1s differ from each other by roughly 5% (Scott et al., 1987, *Genomics* 1: 113–125), these selected elements differed on average by only 0.5% in nucleotide sequence and <1% in amino acid sequence. Unexpectedly, seven of the thirteen elements were found to possess two intact reading frames (Table 4). Previously, the only L1s known to have intact ORFs were the progenitors of the two de novo L1 insertions (L1.2 and LRE2), L1.3, and L1.4 (Scott et al., 1987, *Genomics* 1:113–25; Dombroski et al., 1991, *Science* 254:1805–1808; Dombroski et al., 1993, Proc. Natl. Acad. Sci. U.S.A. 90:6513–6517). No randomly cloned L1 element contained intact ORFs (Hutchison et al., 1989, LINES and related retrotransposons: long interspersed sequences in the eukaryotic genome in Mobile DNA, eds., Berg et al., pp.593–617, ASM Press, Washington, D.C.; Fanning et al., 1987, *Biochim. Biophys. Acta* 910:203–212). The finding fusion protein by Western blot using an anti-HA antibody. The predicted 200 kDa fusion protein (Mathias et al., 1991, *Science* 254:1808–1810) was expressed at comparable levels from most of the constructs. Those elements having frameshift mutations in ORF2 (L1.24 and L1.33) expressed fusion proteins that were truncated when compared with the expected sizes of the proteins. Reduced amounts of Ty1/L1 ORF2 fusion proteins were observed to be expressed by L1.8, L1.14 and L1.21 constructs.

RT activity expressed by each of the thirteen L1s and L1.3 and L1.4 was assessed in a yeast-based genetic assay, the HIS3 pseudogene assay. This assay relies upon L1 RT to reverse transcribe the mRNA of an indicator cassette (mhis3AI) when both the cassette plasmid and a Ty1/L1 ORF2 plasmid are co-expressed in yeast auxotrophic for histidine (His−) and deficient in endogenous Ty1 expression (spt3−) (Dombroski et al., 1994, *Mol. Cell. Biol.* 14:4485–4492; Derr et al., 1991, *Cell* 67:355–364). The resulting cDNA encodes a functional copy of the HIS3 gene;

re-integration and expression of this cDNA results in a His+ phenotype (prototroph). Relative RT activity is proportional to the number of histidine prototrophs.

Seven of the thirteen new L1s, and L1.3, and L1.4 were positive for RT activity in the HIS3 pseudogene assay (FIG. 17C), and the results of the two assays were concordant for eleven of the thirteen new elements as well as L1.3 and L1.4 (Table 4). L1.20 was positive in the genetic assay, but lacked RT activity in the relatively-insensitive biochemical assay. In contrast, L1.21 exhibited RT activity in the biochemical assay, but lacked activity in the genetic assay, suggesting that RT activity per se is insufficient to direct HIS3 pseudogene formation.

Three novel L1s and both L1.3 and L1.4 can retrotranspose in HeLa cells

Figure 18A:
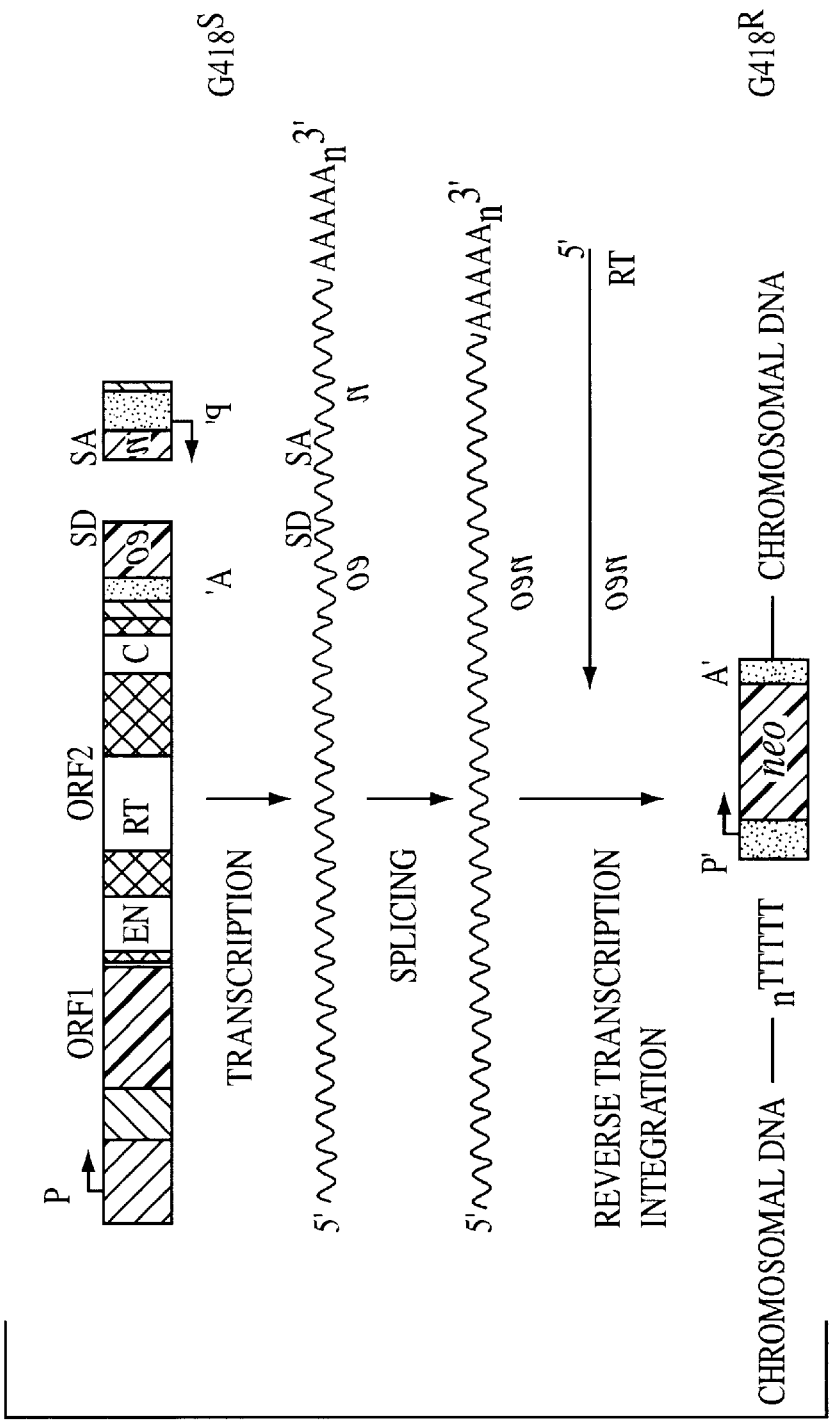
FIG. 18A is a diagram of an overview of the L1 retrotransposon system in Example 3. L1.2 was tagged with an indicator gene (mneoI) designed to detect retrotransposition events as described herein. The indicator gene contains an antisense copy of the neo gene disrupted by intron 2 of the γ-globin gene in the sense orientation (Freeman et al., 1994, BioTechniques 17: 47–52). The splice donor and acceptor sites of the intron are indicated. The neo gene is also flanked by heterologous polyadenylation (A') and promoter (P') sequences denoted by the stippled rectangles. Transcripts originating from the promoter driving L1 expression (P) are spliced, but contain a non-functional copy of the neo gene. G418 resistant (G418$^R$) cells arise only when the L1 mRNA is reverse transcribed, integrated into HeLa chromosomal DNA, and expressed from its own promoter (P').

To address the limitations of the RT assays for assessing retrotransposition potential, a recently developed retrotransposition assay was employed which analyzes the functions of both coding regions of L1 in HeLa cells (FIG. 18). In this assay, as described previously herein, an antisense neomycin resistance gene (neo) under the control of an SV40 promoter is interrupted by a sense γ-globin intron, and is cloned into the 3' UTR of the L1 element (FIG. 18A). G418 resistant (G418$^R$) cells result only when: 1) the antisense neo is transcribed from the promoter driving L1 transcription; 2) the γ-globin intron is spliced out; 3) the transcript is reverse transcribed and integrated into the genome (i.e. the L1 retrotransposes); and, 4) the neo gene is expressed from its adjacent promoter. G418$^R$ cells result from authentic retrotransposition of the neo sequence (FIG. 18A).

Figure 18B:
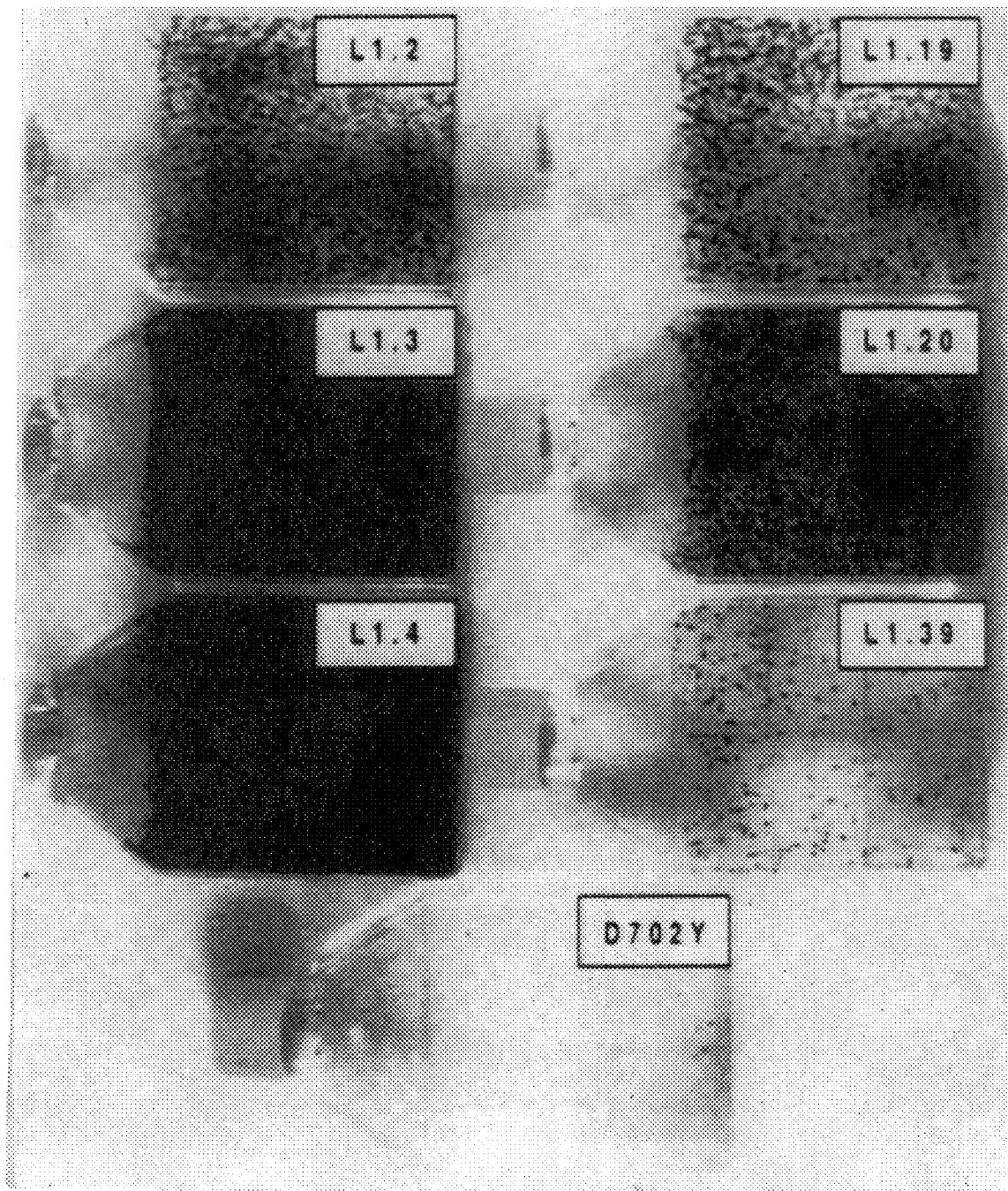
FIG. 18B is a series of images depicting the retrotransposition frequency of various L1 elements. A one hundred-fold variation in retrotransposition frequency among active L1 elements. The retrotransposition assay was performed as described herein. G418$^R$ cells were fixed to flasks and stained with Giemsa for visualization. Flasks containing cells transfected with L1.2, D702Y, L1.3, L1.4, L1.19, L1.20 and L1.39 are shown.

Of the thirteen new L1 elements, three contained frameshift mutations in ORF2 (L1.5, L1.24 and L1.33) and were not tested (Table 4). Of the remaining ten, two (L1.19 and L1.20) retrotransposed at frequencies comparable to that of L1.2 (FIG. 18B), and one (L1.39) retrotransposed at low frequency. Although L1.39 retrotransposed at only about one-fifteenth the frequency of L1.2, that frequency was still about 20 times the frequency of the D702Y mutant (FIG. 18B).

L1.3 and L1.4 were also tested in this assay. Remarkably, both of these elements retrotransposed at frequencies at least five-fold greater than L1.2A (FIG. 18B). Thus, a greater than one hundred-fold range in the frequency of retrotransposition among active L1 elements has been discovered.

LRE2 encodes minimal RT activity

To date, there is no information regarding the RT activity of LRE2, the second element known to have produced a natural insertional mutation via retrotransposition (Holmes et al., 1994, *Nature Genetics* 7:143–148). LRE2 contains a total of 43 nucleotide differences from L1.2, resulting in 17 substitutions in non-conserved amino acids. Despite these differences, LRE2 retrotransposes at 1.5 times the frequency of L1.2 in HeLa cells.

Figure 17C:
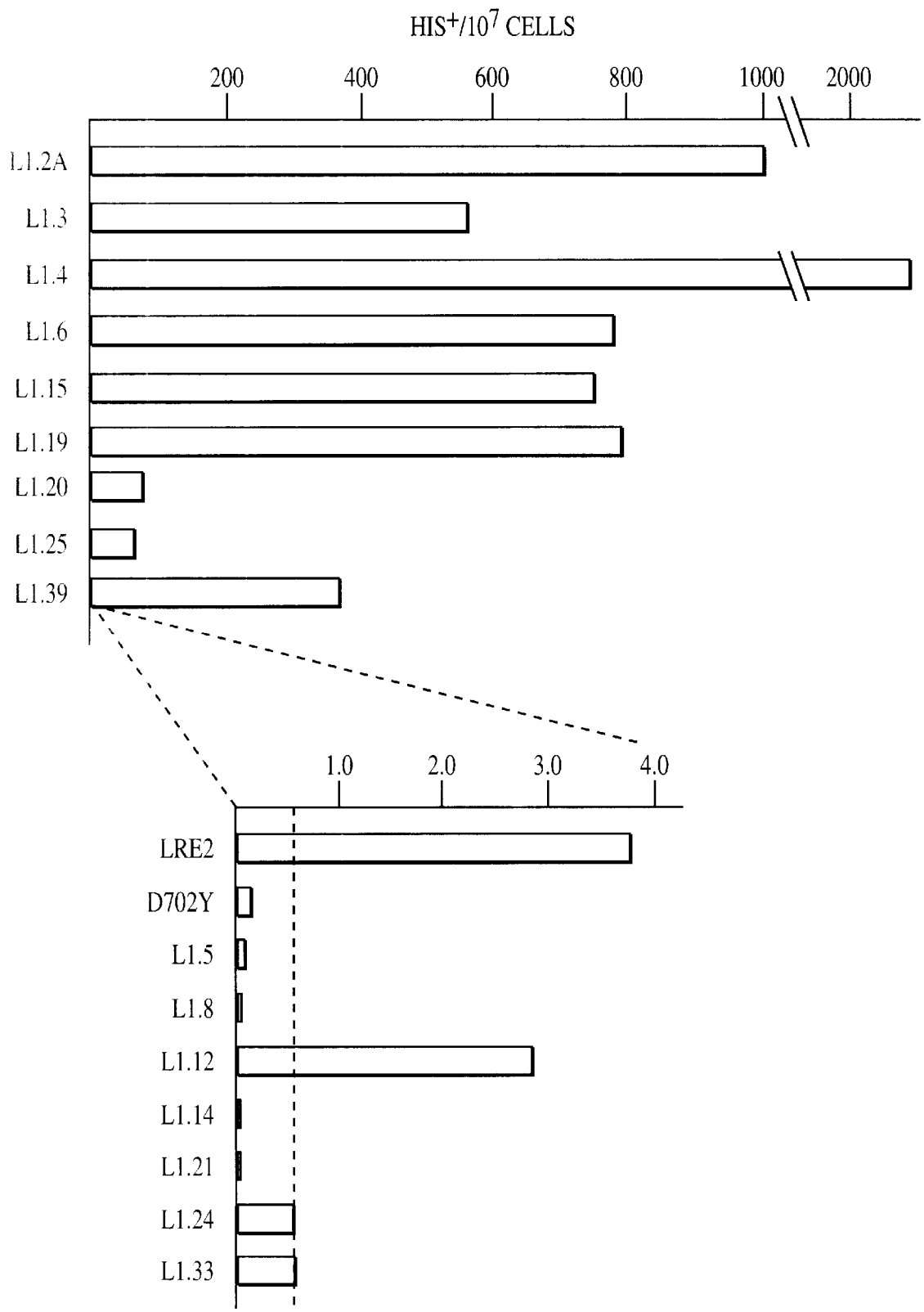
FIG. 17C is a graph depicting the results of the HIS3 pseudogene assay. Constructs containing the reverse transcriptase domain of each L1 element were transformed into yeast strain YDS50.1. His+ prototroph formation requires the presence of a functional reverse transcriptase. The frequency of positive events was determined for at least eight independent transformants derived from at least two separate experiments. The substantial range of frequencies observed necessitated the production of a high-range frequency graph, in which LRE1 serves as a positive control, as well as a low-range graph, in which LRE2 serves as a positive control.

In the experiments described herein, it is apparent that LRE2 possesses little RT activity. In the HIS3 pseudogene assay, LRE2 exhibited <1% of the activity of L1.2, yet the level of this activity clearly above that of background levels (FIG. 17C). In the biochemical assay, it was difficult to determine whether LRE2 contained any RT activity (FIG. 17B). Western blot demonstrated that this reduced activity was not due to low expression or instability of the LRE2 protein.

Gene frequencies of newly-isolated active L1 elements

To determine the gene frequencies of L1.19, L1.20, and L1.39, Southern blots were performed on genomic DNA obtained from a number of individuals to assess the presence (filled site) or absence (empty site) of these elements. Fragment sizes derived from filled and empty sites were determined by restriction mapping of bacteriophage λ containing the L1 elements. Analysis of DNA from individuals of Caucasian, Mediterranean, Southeast Asian, and African-American lineage demonstrated complete homozygosity for the presence of L1.19 (n=38 chromosomes) and L1.39 (n=50 chromosomes). In contrast, L1.20 was polymorphic as to presence in all groups with an overall gene frequency of 0.5 (n=46 chromosomes).

A screen to enrich for active L1s

Until the present invention, the only means of identifying retrotranspositionally-active L1s relied upon the isolation of the progenitor elements of de novo L1 insertions (Holmes et al., 1994, *Nature Genetics* 7:143–148). While this approach was successful in isolating L1.2 and LRE2, it is inefficient and time-consuming because it relies upon serendipity to detect a novel L1 insertion and then requires the arduous task of isolating the particular L1 that produced the insertion. To overcome these difficulties, the method provided herein involves the intentional targeting of a specific subset of full-length L1s for isolation and functional characterization.

Using this screening strategy, thirteen novel L1s were isolated from the Ta subset. Of these thirteen elements, seven contained intact ORFs and eight encoded RT activity in at least one yeast-based assay. Most importantly, three of these thirteen L1s retrotransposed in HeLa cells. In addition, the data demonstrate that two previously isolated L1.2 subfamily members (L1.3 and L1.4) encode RT and also retrotranspose in HeLa cells at remarkably high frequencies (about 1 in 150–200 cells containing the expression construct). Therefore, according to the present invention, new L1s have been identified which are candidates for retrotransposition into genes for the production of disease. Application of similar screening strategies should allow the isolation of most remaining active L1s in the human genome. By isolating and characterizing these elements, strategies may be employed which prevent their retrotransposition. Further, the mere identification of the elements in the present study provides a means of diagnosing individuals who are at risk for disease mediated by retrotransposition.

The data presented herein establish that the two L1.2 subfamily members (L1.3 and L1.4) retrotranspose in HeLa cells at remarkably high frequencies. Interestingly, the encoded proteins of L1.3 and L1.4 differ from L1.2 by only four and six amino acids in ORF2, respectively. As discussed herein, engineered L1 elements are useful in transposon mutagenesis of mammalian genomes. Because L1.3 and L1.4 have elevated retrotransposition rates, they are currently the best candidates to use in such an experiment.

Three L1s (L1.15, L1.21 and L1.25) contained intact ORFs and encoded RT activity, yet were unable to retrotranspose (Table 4). These results support the notion that RT activity is necessary, but not sufficient, for retrotransposition. These elements likely contain another mutation(s) that affects some as yet unknown domain required for retrotransposition. The more comprehensive retrotransposition assay has now complemented the RT assays and has facilitated characterization of seven active L1s. Notably, two active L1s (L 1.20 and LRE2) encode very low RT activity, yet they retrotranspose at frequencies greater than that of L1.2, suggesting that RT activity may not be rate-limiting for retrotransposition.

Active L1s are dispersed in the genome and are present at high gene frequencies

The three novel active elements, L1.19, L1.20, and L1.39, were mapped to chromosomes 7, 20, and 14, respectively. In previous studies, LRE1 mapped to chromosome 22 (Dombroski et al., 1991, *Science* 254:1805–1808), L1.3 to chromosome 14, L1.4 to chromosome 9 (Dombrowski et al., 1993, *Proc. Natl. Acad. Sci. U.S.A.* 90:6513–6517), and LRE2 to chromosome 1 (Holmes et al., 1994, *Nature Genetics* 7:143–148). Thus, the seven active elements are located on six different human chromosomes. From gene frequency data presented herein, the number of copies of these active L1s in the average human genome can be determined. L1.2, L1.19, and L1.39 have gene frequencies of 1.0; thus, the diploid genome contains two copies of each of these elements. Gene frequencies of LRE2 (0.65), L1.20 (0.50), L1.4 (0.30), and L1.3 (0.15) suggest that the average genome contains about 3 L1s from this set of elements. Thus, the average genome contains nine copies of these seven elements. Since four of the seven L1s are polymorphic, it is likely that both full-length and truncated L1s may represent a rich source of diallelic polymorphisms for use in genome analysis. The finding that seven L1s have attained high gene frequencies suggests positive selection and a possible function for these elements. Along these lines, it has recently been shown that L1s may act as molecular band-aids to repair double-strand breaks in chromosomal DNA (Teng et al., 1996, *Nature* 383:641–644).

An estimate of the number of active L1s in the genome

In a haploid human genome, there are roughly 3,000 to 4,000 full-length L1 elements (Adams et al., 1980, *Nucl. Acids Res.* 8:6113–6128). The number of full-length L1s that belong to the Ta subset were estimated using two different methods. First, successive plaque hybridization experiments were performed which demonstrated that approximately 1.5–2.5% of full-length L1s belong to the Ta subset. This limits the number of fill-length, Ta subset elements to between 45 (3,000×0.015) and 100 (4,000×0.025) per haploid genome. Second, human genomic DNA was digested with AccI and Southern analysis was performed on digested DNA. Since most full-length L1 elements contain AccI sites only at each end of the element, the great majority of full-length L1s produce a 6 kb fragment on Southern blots. Quantitative analysis with a probe specific for Ta-subset L1s (oligomer C, FIG. 16) demonstrated that a haploid genome contains about 80 full-length Ta subset L1s.

The data presented herein establish that three of thirteen randomly-isolated Ta subset elements can retrotranspose. Multiplying this fraction (3/13) by the number of full-length, Ta subset elements (about 80) provides an estimate of 18 active Ta subset L1s. However, one of seven known human L1 insertions was not derived from a Ta subset element. To include active non-Ta subset elements, 18 is multiplied by 7/6 to arrive at an estimate of 22 active L1 elements in a haploid human genome and 44 in the diploid genome. It is obviously difficult to place precise confidence limits on this estimate, since it was derived by several steps, each with an unknown error, and the effect of cumulating these errors is very uncertain. However, it is believed that a reasonable range for the number of active L1s in the diploid genome is 30–60. The precursors of five naturally occurring L1 insertions are not represented among the 7 active L1s identified herein. In the average diploid genome, these five precursors may be represented by 5–10 copies which when added to the 9 copies of the active L1s isolated herein, brings the number of active L1s already accounted for to 14–19.

Endogenous reverse transcriptases have had a profound effect on the human genome (Temin et al., 1985, *Mol. Biol. Evol.* 2:455–468; Weiner et al., 1986, *Ann. Rev. Biochem.* 55:631–661). The structures of Alu elements and processed pseudogenes, sequences important for genome diversity, suggest that they were dispersed using the L1 RT. The extent to which the retrotransposition of these repetitive elements currently influences the genome remains unknown, but the data presented herein suggest that a substantial number of L1s are available as a source of reverse transcriptase for this process.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. An isolated DNAc molecule comprising a promoter P and an L1 cassette sequence;
   wherein said L1 cassette sequence comprises a core retrotransposon element;
   wherein said core L1 retrotransposon element comprises a 5' UTR, ORF1, ORF2 comprising EN and RT domains, a 3' UTR, a poly A signal, and a vector sequence comprising at least one origin of DNA replication and a DNA sequence encoding at least one selectable marker protein;
   wherein said isolated DNAc molecule further comprises a fragment of non-L1 DNA and a promoter P' for expression of the non-L1 DNA, wherein said non-L1 DNA and promoter P' are positioned within said 3' UTR or between said 3' UTR and said poly A signal.

2. The isolated DNAc molecule of claim 1, wherein said non-L1 DNA encodes a protein selected from the group consisting of cystic fibrosis transmembrane conductance regulator, β-globin, an enzyme, a tumor suppressor protein and a cytokine.

3. The isolated DNAc molecule of claim 1, wherein said non-L1 DNA is a marker gene.

* * * * *